US009527823B2

(12) United States Patent
Carroll et al.

(10) Patent No.: US 9,527,823 B2
(45) Date of Patent: *Dec. 27, 2016

(54) HYDROXYBUPROPION ANALOGUES FOR TREATING DRUG DEPENDENCE

(71) Applicants: Research Triangle Institute, Research Triangle Park, NC (US); Dignity Health, Phoenix, AZ (US); Virginia Commonwealth University, Richmond, VA (US)

(72) Inventors: Frank Ivy Carroll, Durham, NC (US); Bruce E. Blough, Raleigh, NC (US); Hernan A. Navarro, Chapel Hill, NC (US); S. Wayne Mascarella, Hillsborough, NC (US); Ana Zamfira Muresan, Raleigh, NC (US); M. Imad Damaj, Richmond, VA (US); Ronald J. Lukas, Phoenix, AZ (US)

(73) Assignees: Research Triangle Institute, Research Triangle Park, NC (US); Dignity Health, Phoenix, AZ (US); Virginia Commonwealth University, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/537,124

(22) Filed: Nov. 10, 2014

(65) Prior Publication Data

US 2015/0141416 A1    May 21, 2015

Related U.S. Application Data

(63) Continuation of application No. 13/680,710, filed on Nov. 19, 2012, now Pat. No. 8,906,908, which is a continuation of application No. PCT/US2011/037312, filed on May 20, 2011.

(60) Provisional application No. 61/347,241, filed on May 21, 2010.

(51) Int. Cl.
  *C07D 265/32*   (2006.01)
  *A61K 31/5375*  (2006.01)

(52) U.S. Cl.
  CPC ......... *C07D 265/32* (2013.01); *A61K 31/5375* (2013.01)

(58) Field of Classification Search
  CPC .................... A61K 31/5375; C07D 265/32
  See application file for complete search history.

(56) References Cited

U.S. PATENT DOCUMENTS

| | | |
|---|---|---|
| 1,867,982 A | 7/1932 | Naunton et al. |
| 2,364,347 A | 12/1944 | Dickey et al. |
| 2,832,777 A | 4/1958 | Kalm |
| 2,997,469 A | 8/1961 | Heel et al. |
| 3,018,222 A | 1/1962 | Siemer et al. |
| 3,117,967 A | 1/1964 | Anderson et al. |
| 3,125,572 A | 3/1964 | Siemer et al. |
| 3,225,042 A | 12/1965 | Dillard et al. |
| 3,555,019 A | 1/1971 | Fouche et al. |
| 3,642,789 A | 2/1972 | Faith et al. |
| 3,714,161 A | 1/1973 | Mallion et al. |
| 3,959,273 A | 5/1976 | Mallion et al. |
| 4,044,131 A | 8/1977 | Asselin et al. |
| 4,360,519 A | 11/1982 | White et al. |
| 4,576,944 A | 3/1986 | Lafon |
| 4,766,212 A | 8/1988 | Freedman et al. |
| 5,104,870 A | 4/1992 | Kelley et al. |
| 5,648,347 A | 7/1997 | Mehta et al. |
| 6,693,192 B1 | 2/2004 | Chrysselis et al. |
| 8,906,908 B2 * | 12/2014 | Carroll ............... A61K 31/5375 514/231.2 |
| 2005/0267096 A1 | 12/2005 | Allerton et al. |
| 2010/0016312 A1 | 1/2010 | Lee et al. |
| 2012/0071560 A1 | 3/2012 | Carroll et al. |
| 2013/0203752 A1 | 8/2013 | Blough et al. |

FOREIGN PATENT DOCUMENTS

| | | |
|---|---|---|
| DE | 11 35 464 | 8/1962 |
| DE | 11 43 201 | 2/1963 |
| DE | 2152686 | 5/1972 |
| EP | 0 116 373 | 8/1984 |
| EP | 0 170 430 | 2/1986 |
| EP | 0 174 242 | 3/1986 |

(Continued)

OTHER PUBLICATIONS

Boswell et al, "Synthesis and Anti-tetrabenazine Activity of C-3 Analogues of Dimethyl-2-phenylmorpholines," *J. Heterocyclic Chemistry*, 1996, vol. 33 (1), p. 33-39.

Carroll et al., "Synthesis and Biological Evaluation of Bupropion Analogues as Potential Pharmacotherapies for Smoking Cessation," *J. Medicinal Chem.*, 2010, vol. 53 (5) pp. 2204-2214.

Hu et al., "Synthesis of 2-Aryl-3,5,5-trimethyl-2-morpholinols Hydrochloride," *Chinese Journal of Applied Chemistry*, 2005, vol. 22, No. 3, pp. 343-345.

(Continued)

*Primary Examiner* — Rebecca Anderson

(74) *Attorney, Agent, or Firm* — Womble Carlyle Sandridge & Rice, LLP

(57) ABSTRACT

The invention provides hydroxybupropion analogs capable of inhibiting the reuptake of one or more monoamines and/or acting as antagonists at nicotinic acetylcholine receptors. The compounds may selectively bind to one or more monoamine transporters, including those for dopamine, norepinephrine, and serotonin and/or may selectively bind to one or more nicotinic acetylcholine receptor subtypes. Such compounds may be used to treat conditions that are responsive to modification of monoamine levels and/or antagonism of nicotinic acetylcholine receptors, including drug dependency, depression, and obesity.

20 Claims, 2 Drawing Sheets

(56) References Cited

FOREIGN PATENT DOCUMENTS

| EP | 0 426 416 | 2/1994 |
|---|---|---|
| FI | 852 657 | 1/1986 |
| FR | 1 397 563 | 4/1965 |
| FR | 2285886 | 9/1974 |
| FR | 2553411 | 10/1983 |
| GB | 773780 | 5/1957 |
| GB | 817932 | 8/1959 |
| GB | 851311 | 10/1960 |
| GB | 862198 | 3/1961 |
| GB | 883220 | 11/1961 |
| GB | 899386 | 6/1962 |
| GB | 1 298 771 | 12/1972 |
| GB | 1 336 732 | 11/1993 |
| WO | WO 92/18489 | 10/1992 |
| WO | WO 93/15052 | 8/1993 |
| WO | WO 99/37305 | 7/1999 |
| WO | WO 00/42030 | 7/2000 |
| WO | WO 01/62257 | 8/2001 |
| WO | WO 2004/052372 | 6/2004 |
| WO | WO 2008/026046 | 3/2008 |
| WO | WO 2008/087512 | 7/2008 |

OTHER PUBLICATIONS

Avramova et al., "Derivatives of 2-and 2,3-Disubstituted Tetrahydrooxazines," *Bulgarian Chemical Communications*, 1992, pp. 387-390, vol. 25, No. 3.
Balsamo et al., "Synthesis and Pharmacological Properties of cis-2-(2,5-dimethoxyphenyl)-3-Methylmorpholine and its N-isopropyl Derivative," *Eur. J. Med. Chem.—Chimica Therapeutica*, 1978, pp. 321-326, vol. 13, No. 4.
Bettoni et al., "Synthesis of Rigid Dopamine Congeners: CIS and TRANS 2-(p-Methoxyphenyl)-3-Methylmorpholine," *Tetrahedron*, 1986, pp. 2117-2120, vol. 42, No. 7.
Blagg et al., "Design and Synthesis of a Functionally Selective D3 Agonist and its in Vivo Delivery Via the Intranasal Route," *Bioorganic & Medicinal Chemistry Letters*, 2007, pp. 6691-6696, vol. 17.
Boswell et al., "Synthesis and Anti-Tetrabenazine Activity of C-3 Analogues of Dimethyl-2-phenylmorpholines," *J. Heterocyclic Chem.*, 1996, pp. 33-39, vol. 33, No. 33.
Carroll et al., "Synthesis and Biological Evaluation of Bupropion analogues as Potential Pharmacotherapies for Cocaine Addiction," *J. Med. Chem.*, 2009, pp. 6768-6781, vol. 52.
Carroll et al., "Synthesis of 2-(Substituted Phenyl)-3,5,5-trimethylmorpholine Analogues and Their Effects on Monoamine Uptake, Nicotinic Acetylcholine Receptor Function, and Behavioral Effects of Nicotine," *Journal of Medicinal Chemistiy*, 2011, pp. 1441-1448, vol. 54, No. 5.
Dijkstra et al., "Synthesis and Pharmacology of *trans*-4-n-Propyl-3,4,4a,10b-tetrahydro-2*H*,5*H*-1-Benzopyrano[4,3,-*b*-]-1,4-Oxazin-7- and -9ols: The Significance of Nitrogen p$K_a$Values for Central Dopamine Receptor Activation," *J. Med. Chem.*, 1988, pp. 2178-2182, vol. 31.
Franklin et al., "The Metabolism of Phenmetrazine in Man and Laboratory Animals," *Drug Metabolism and Disposition*, 1977, pp. 223-233, vol. 5, No. 3.

Glennon et al., β-Oxygenated Analogues of the 5-HT$_{2A}$ Serotonin Receptor Agonist 1-(4-Bromo-2,5-dimethoxyphenyl)-2-aminopropane, *J. Med. Chem.*, 2004, pp. 6034-6041, vol. 47.
Hu et al., Yingyong Huaxue (2005), 22(3), 343-345.
Kafka el al., Syntheses of 3-aminoquinoline-2,4(1H,3H)-diones, Heterocycles, 2002, vol. 57, No. 9, pp. 1659-1682.
Kalm et al., "4-Aminomorpholines," *J. Med. Chem.*, 1964, pp. 427-433.
Ludwig et al., "Electrophilic Asymmetric Syntheses of α-Hydroxy Carboxylic Acids," *Tetrahedron Letters*, 1986, pp. 2731-2734, vol. 27, No. 24.
Lukas et al., "Synthesis and Characterization of In Vitro and In Vivo Profiles of Hydroxybupropion analogues: Aids to Smoking Cessation," *Journal of Medicinal Chemistry*, 2010, pp. 4731-4748, vol. 53.
Manera et al., "X-Ray analysis, Theoretical Studies and α-Adrenergic Biophamacological Properties of 1-(2,4-Dimethoxyphenyl)-2-Aminoethanol and its Morpholine Analogue," *Eur. J. Med Chem.*, 1994, pp. 519-525, vol. 29.
Negus et al., "Selective Suppression of Cocaine-Versus Food-Maintained responding by Monoamine Releasers in Rhesus Monkeys: Benzylpiperazine, (+) Phenmetrazine, and 4-Benzylpiperidine," *The Journal of Pharmacology and Experimental Therapeutics*, 2009, pp. 272-281, vol. 329, vol. 1.
Rothman et al., "Amphetamine-Type Central Nervous System Stimulants Release Norepinephrine More Potently Than They Release Dopamine and Serotonin," *Synapse*, 2000, 39:32-41 (2001).
Rothman et al., "Interaction of the Anorectic Medication, Phendimetrazine, and its Metabolites with Monoamine Transporters in Rat Brain," *Eur J Pharmacol*, 2002, 447(1):51-7.
Sheradsky et al., "The Reaction of Phenylglyoxal with 2-Aminoalcohols. Rearrangement of 2-Acyloxazolidines to 2-Hydroxy-5,6-Dihydro-1,4-Oxazines," *J. Heterocyclic Chem*, 1996, pp. 1271-1274, vol. 33.
Stevens et al., "Epoxy Ethers, XX. Synthesis of Diamines, Morpholines, and Piperazines," Department of Chemistry, Wayne State University, Detroit 1, Michigan, *Journal of Organic Chemistry*, 1964, pp. 3146-3151, vol. 29.
Swist et al., "Determination of Synthesis Route of 1-(3,4-Methylenedioxphenyl)-2-Propanone (MDP-2-P) Based on Impurity Profiles of MDMA," *Forensic Science International*, 2005, pp. 181-192, vol. 149.
Talaty el al., The reaction of β—lactams with Grignard reagents: A correction of the literature, Tetrahedron Letters, 1976, vol. 52, pp. 4797-4800.
Tiecco et al., "Selenium-Promoted Synthesis of Enantiomerically Pure Substituted Morpholines Starting From Alkenes and chiral Aminoalcohols," *Tetrahedron: Asymmetry*, 2003, pp. 2651-2657, vol. 14.
Van Vliet et al., "Synthesis and Pharmacological Evaluation of Thiopyran Analogues of the Dopamine D$_3$ Receptor-Selective Agonist (4a*R*,10b*R*)-(+)-*trans*-3,4,4a,10b-Tetrallydro-4-*n-propyl*-2*H*,5*H*-[1]Benzopyrano[4,3-*b*]-1,4-Oxazin-9-ol (PD 128907)," *J. Med. Chem.*, 2000, pp. 2871-2882, vol. 43.
Wee et al., "Relationship Between the Serotonergic Actifity and Reinforcing Effects of a Series of Amphetamine Analogs," *The Journal of Pharmacology and Experimental Therapeutics*, 2005, pp. 848-854, vol. 313, No. 2.

* cited by examiner

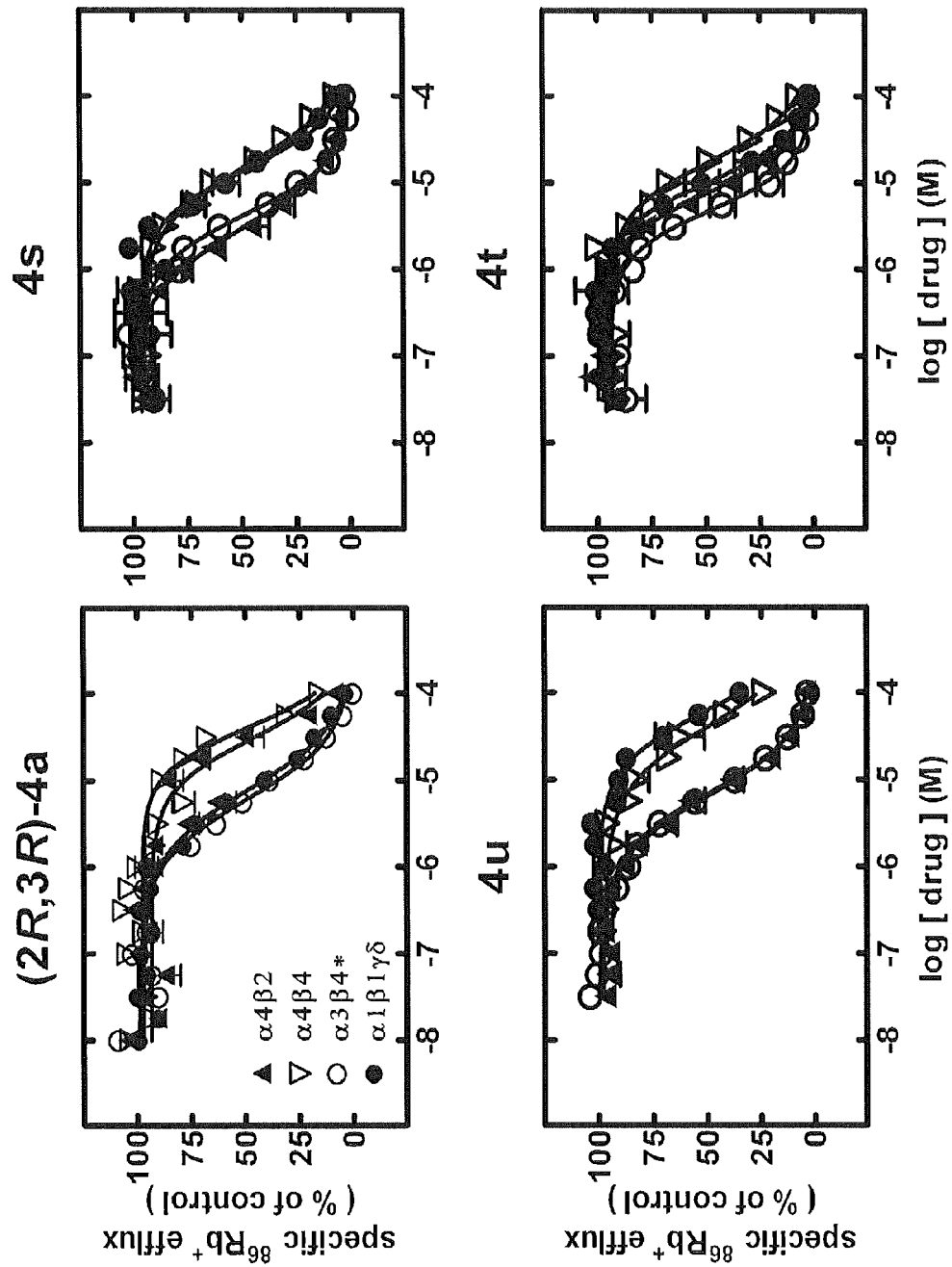

ively few chemical analogues have been prepared and evaluated. Since only about one-fifth of smokers are able to maintain long-term (12 months) abstinence with any of the present pharmacotherapies, there is a need in the art for new and improved pharmaceutical compositions for treating drug addiction.

HYDROXYBUPROPION ANALOGUES FOR TREATING DRUG DEPENDENCE

CROSS-REFERENCE TO RELATED APPLICATIONS

The present application is a continuation of U.S. application Ser. No. 13/680,710, which is a continuation of PCT International Application No. PCT/US2011/037312, filed May 20, 2011, which claims the benefit of U.S. Provisional Application No. 61/347,241, filed May 21, 2010. All of these applications are incorporated by reference herein in their entireties.

FEDERALLY SPONSORED RESEARCH OR DEVELOPMENT

This invention was made with United States Government support under grant U19 DA019377, awarded by the National Institutes of Health National Cooperative Drug Discovery Group. The United States Government has certain rights in the invention.

FIELD OF THE INVENTION

The present application is directed to various compounds and methods of preparation of compounds that are capable of functioning as monoamine reuptake inhibitors and/or as antagonists of nicotinic acetylcholine receptors. The application is also directed to pharmaceutical compositions containing one or more of these compounds, which may also contain one or more additional therapeutic agents. It is also directed to methods of treatment of various conditions, such as drug dependency, depression, and obesity, which may be responsive to inhibition of monoamine reuptake and/or antagonism of nicotinic acetylcholine receptors.

BACKGROUND OF THE INVENTION

Tobacco use is the leading preventable cause of disease, disability, and death in the United States. Cigarette smoking results in more than 400,000 premature deaths in the United States each year, accounting for about 1 in every 5 deaths according to the Centers for Disease Control 2008 Smoking and Tobacco Use Fact Sheet. Statistics from the U.S. Department of Health and Human Services show that, on average, adults who smoke die 14 years earlier than nonsmokers.

Cigarette smoking accounts for about one-third of all cancers, including 90% of lung cancer cases. Smoking also causes lung diseases such as chronic bronchitis and emphysema and increases the risk of stroke, heart attack, vascular disease, and aneurysm. In spite of these documented connections between tobacco use and disease, a large number of people continue to use tobacco products. In 2008, 28.6% of the U.S. population 12 years of age and older (70.9 million people) had used a tobacco product at least once in the month prior to being interviewed. This figure includes 3.1 million young people aged 12-17 (12.4% of this age group).

Nicotine is considered the main psychoactive component in tobacco smoke that causes people to use and continue to use tobacco products. The pharmacological and behavioral effects result from the activation of different nicotinic acetylcholine receptor (nAChR) subtypes. The subtypes are either homo or hetero pentameric ion channels, consisting of different combinations of genetically distinct subunits, ($\alpha$1, $\alpha$2-$\alpha$10, $\beta$1-$\beta$4, $\gamma$, $\delta$, $\epsilon$). The predominant nAChR subtypes found in the brain are thought to be heteromeric $\alpha$4$\beta$2 nAChR or homomeric $\alpha$7-nAChR; however, appreciable amounts of $\alpha$3$\beta$4* and $\alpha$6$\beta$2* nAChRs (where the * indicates that other subunits are known or are possible assembly partners with those specified) are also in the brain regions implicated in reward and drug dependence.

Nicotine exposure can stimulate activity of somatodendritic nAChRs to alter neuronal electrical activity and neurotransmitter release as a consequence of neuronal activation. However, by acting at nAChRs positioned on nerve terminals, nicotine can also increase neurotransmitter release as a consequence of local depolarization of the nerve terminal membrane potential and/or calcium ion mobilization in terminals. The integration of these effects is likely to contribute to nicotine's actions, including those that are presumably involved in its reinforcement of tobacco product use, such as effects in monoaminergic reward pathways.

Even though nicotine dependence has a huge impact on global health, pharmacotherapies for treating tobacco use are limited. Current treatments include nicotine-replacement therapies (NRTs), bupropion, and varenicline. Bupropion [($\pm$)-2-tert-butylamino-3'-chloropropiophenone] is used clinically for the treatment of nicotine addiction as a racemic mixture of its (R)- and (S)-isomers (formulated in a sustained release formulation and currently marketed for this purpose as Zyban®). Bupropion is extensively metabolized with less than 1% recovered intact in urine. Major metabolites result from hydroxylation of the N-tert-butyl group by the P450-(CYP)2B6 isoenzyme. The resulting hydroxylated metabolites cyclize to give (2R,3R)- and (2S,3S)-hydroxybupropion. Several studies suggest that (2S,3S)-hydroxybupropion contributes to the antidepressant and smoking cessation efficacy of bupropion. Peak plasma and cerebrospinal fluid concentrations of (2S,3S)-hydroxybupropion exceed those of bupropion by 4- to 7-fold and have a longer elimination half-life than the parent drug.

The compound (2S,3S)-hydroxybupropion has previously been shown to act as an inhibitor of both dopamine (DA) and norepinephrine (NE) uptake. Furthermore, it has been determined to be a noncompetitive functional antagonist at $\alpha$4$\beta$2-nAChRs with an $IC_{50}$ value of 3.3 $\mu$M, a concentration that is comparable to those needed to inhibit DA and NE uptake. In addition, (2S,3S)-hydroxybupropion was demonstrated to be 3-10 times more potent than bupropion after acute administration in mice in antagonizing nicotine-induced hypomobility and hypothermia and nicotine-induced analgesia in tail-flick and hot-plate tests. It was also equally potent with bupropion in the antidepressant mouse forced-swimming test.

Although bupropion is a successful treatment for nicotine addiction, relatively few chemical analogues have been prepared and evaluated. Since only about one-fifth of smokers are able to maintain long-term (12 months) abstinence with any of the present pharmacotherapies, there is a need in the art for new and improved pharmaceutical compositions for treating drug addiction.

SUMMARY OF THE INVENTION

The present invention provides compounds useful as monoamine reuptake inhibitors and methods of synthesis of such compounds. It also provides pharmaceutical compositions containing the compounds, which may be useful in the treatment of various conditions or disorders responsive to the inhibition of monoamine reuptake by cells and/or the antagonism of nicotinic acetylcholine receptors. The invention further provides methods of treating such conditions and disorders, including but not limited to, addiction, depression, and obesity. For example, in one aspect, the invention is directed to a method of treating a condition comprising administering to a subject in need of treatment of the condition a pharmaceutical composition comprising a therapeutically effective amount of a compound of the present invention or a pharmaceutically acceptable ester, amide, salt, solvate, prodrug, or isomer thereof.

Accordingly, in one aspect, the present invention provides a compound that inhibits the reuptake of one or more monoamines and/or acts as an antagonist at α4β2 nAChRs. In some embodiments, the invention provides a compound according to the following structure:

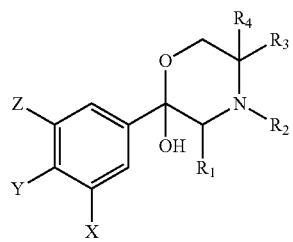

wherein:

$R_1$ is optionally substituted C1-10 alkyl;

$R_2$ is H or optionally substituted C1-10 alkyl;

$R_3$ and $R_4$ are each independently selected from optionally substituted C1-10 alkyl;

X, Y, and Z are each independently selected from H; optionally substituted C1-10 alkyl; optionally substituted C1-10 alkoxy; optionally substituted C2-10 alkenyl; optionally substituted C2-10 alkynyl; optionally substituted C6-C12 aryl; alkaryl; arylalkyl; aryloxy; optionally substituted heteroaryl; optionally substituted heterocycle; halo; hydroxyl; halogenated alkyl; an amino group of formula $NH_2$, $NR_{12}H$, or $NR_{12}R_{13}$; alkylamino; arylamino; acyl; CN; $NO_2$; $N_3$; $CH_2OH$; $CONH_2$; $CONR_{12}R_{13}$; $CO_2R_{12}$; $CH_2OR_{12}$; $NHCOR_{12}$; $NHCO_2R_{12}$; C1-3 alkylthio; sulfate; sulfonic acid; sulfonate ester; phosphonic acid; phosphate; phosphonate; mono-, di-, or triphosphate ester; trityl or monomethoxytrityl; $R_{12}SO$; $R_{12}SO_2$; $CF_3S$; $CF_3SO_2$; trialkylsilyl; and diphenylmethylsilyl; or wherein X and Y or Y and Z form a fused aryl ring together with the phenyl ring to which X, Y, and Z are attached; and $R_{12}$ and $R_{13}$ are each independently selected from H or optionally substituted C1-10 alkyl;

with the proviso that either (a) X is a halo substituent other than chloro; (b) two or more of X, Y, and Z are halo substituents; (c) one or more of X, Y, and Z are optionally substituted C6-C12 aryl; (d) X and Y or Y and Z form a fused aryl ring together with the phenyl ring to which X, Y, and Z are attached; (e) $R_1$ is an optionally substituted C2-C10 alkyl; or any combination of two or more of (a) through (e), or a pharmaceutically acceptable ester, amide, salt, solvate, prodrug, or isomer thereof.

In certain specific embodiments, the invention provides a compound having the structure:

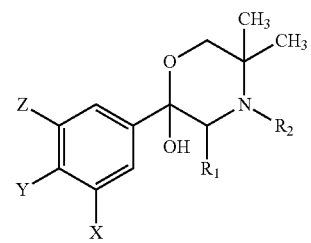

wherein all substituents are as noted above, or a pharmaceutically acceptable ester, amide, salt, solvate, prodrug, or isomer thereof.

In another specific embodiment, the invention provides a compound having the structure:

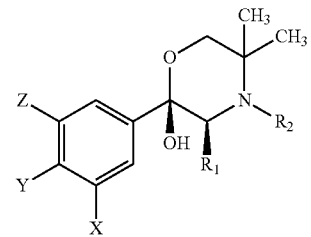

wherein all substituents are as noted above, or a pharmaceutical acceptable ester, amide, salt, solvate, prodrug, or isomer thereof.

In certain embodiments, a compound is provided according to the above structures, wherein $R_1$ is selected from the group consisting of $CH_3$, $CH_2CH_3$, and $C_3H_7$. In some embodiments, a compound is provided according to the above structures, wherein X, Y, and Z are independently selected from the group consisting of H, Cl, Br, F, optionally substituted C1-10 alkyl, and phenyl. In some embodiments, a compound is provided according to the above structures, wherein X and Y or Y and Z form a fused aryl ring together with the phenyl ring to which X, Y, and Z are attached.

In further embodiments of the invention, a compound is provided according to the above structures, wherein $R_1$ is optionally substituted methyl, ethyl, propyl, or butyl, and at least one of X, Y, and Z is optionally substituted C6-C12 aryl or X and Y or Y and Z form a, fused aryl ring together with the phenyl ring to which X, Y, and Z are attached. In some embodiments, $R_1$ is optionally substituted C2-C10alkyl, and at least one of X, Y, and Z is optionally substituted C6-C12 aryl or halo, or X and Y or Y and Z form a fused aryl ring together with the phenyl ring to which X, Y, and Z are attached.

Certain compounds that are provided herein include, but are not limited to, 2-(3-Fluorophenyl)-3,5,5-trimethylmorpholin-2-ol; 2-(3-Bromophenyl)-3,5,5-trimethylmorpholin-2-ol; 2-Biphenyl-4-yl-3,5,5-trimethylmorpholin-2-ol; 2-(3,4-Dichlorophenyl)-3,5,5-trimethylmorpholin-2-ol; 2-(Naphthalen-2-yl)-3,5,5-trimethylmorpholin-2-ol; 2-(3-Chlorophenyl)-3-ethyl-5,5-dimethylmorpholin-2-ol; 2-(3-Chlorophenyl)-5,5-dimethyl-3-propyl-morpholin-2-ol, and pharmaceutically acceptable esters, amides, salts, solvates, prodrugs, or isomers thereof.

Other exemplary compounds that are provided herein include, but are not limited to, 2-(m-Tolyl)-3,5,5-trimethylmorpholin-2-ol; 2-(3-Methoxyphenyl)-3,5,5-trimethylmorpholin-2-ol; 2-(4-Fluorophenyl)-3,5,5-trimethylmorpholin- 2-ol; 2-(4-Chlorophenyl)-3,5,5-trimethylmorpholin-2-ol; 3,5,5-Trimethyl-2-(4-methylphenyl)morpholin-2-ol; 2-(4-Methoxyphenyl)-3,5,5-trimethylmorpholin-2-ol; 2-(3,4-Difluorophenyl)-3,5,5-trimethylmorpholin-2-ol; (2S,3S)-2-(3,5-Difluorophenyl)-3,5,5-trimethylmorpholin-2-ol; 2-(3,5-Dichlorophenyl)-3,5,5-trimethylmorpholin-2-ol; 2-(Naphthalen-1-yl)-3,5,5-trimethylmorpholin-2-ol; 2-(3-Chlorophenyl)-3,4,5,5-tetramethylmorpholin-2-ol; 2-(4-Chlorophenyl)-3,4,5,5-tetramethylmorpholin-2-ol, and pharmaceutically acceptable esters, amides, salts, solvates, prodrugs, or isomers thereof.

In certain embodiments a compound according to the foregoing structures is provided, wherein the compound comprises an enantiomeric excess of at least 95% of the (2S-3S) enantiomer.

In another aspect of the present invention is provided a pharmaceutical composition comprising a compound according to any of the foregoing structures and one or more pharmaceutically acceptable carriers.

In still another aspect is provided a method for treating or delaying the progression of disorders that are alleviated by inhibiting monoamine reuptake in a patient or antagonizing the nicotinic acetylcholine receptors, the method comprising administering a therapeutically effective amount of at least one compound according to any one of the foregoing structures. In some embodiments, the disorder is selected from the group consisting of addiction, depression, obesity, bipolar disorder, attention deficit disorder (ADD), attention deficit/hyperactivity disorder (ADHD), hypoactive sexual desire disorder, antidepressant-induced sexual dysfunction, orgasmic dysfunction, seasonal affective disorder/winter depression, mania, bulimia and other eating disorders, panic disorders, obsessive compulsive disorder, schizophrenia, schizo-affective disorder, Parkinson's disease, narcolepsy, anxiety disorders, insomnia, chronic pain, migraine headaches, and restless legs syndrome. In certain embodiments, addiction comprises nicotine addiction.

BRIEF DESCRIPTION OF THE DRAWINGS

FIG. 2 shows the effect of alkyl extensions on specific $^{86}Rb^+$ efflux on various nAChR sub-types in the presence of a receptor subtype-specific, $EC_{80}$-$EC_{90}$ concentration of the full agonist, carbamylcholine, either alone or in the presence of the indicated concentrations of compound.

DETAILED DESCRIPTION OF THE INVENTION

Figure 1:
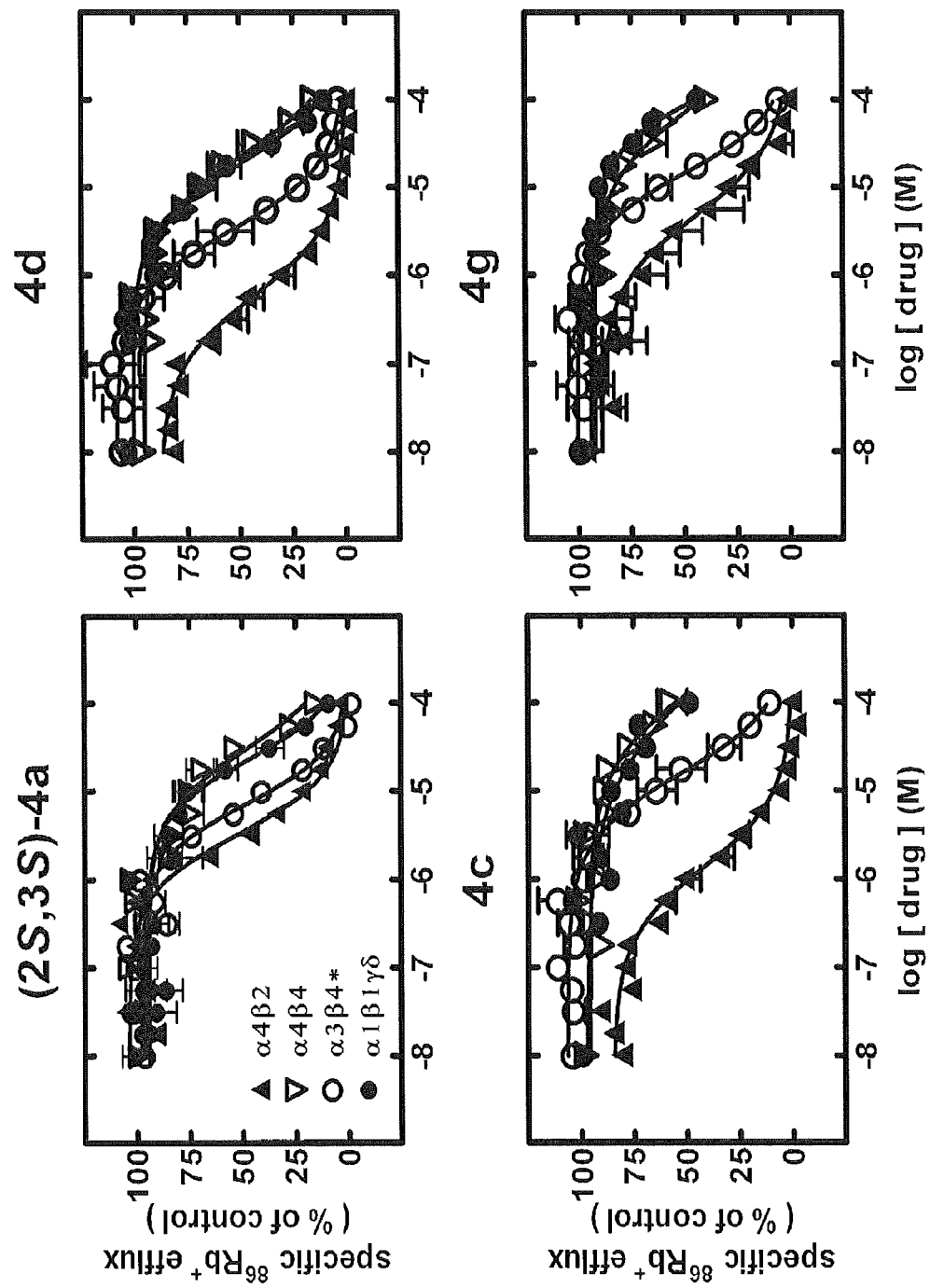
FIG. 1 shows the effect of phenyl substitution on specific $^{86}Rb^+$ efflux on various nAChR sub-types in the presence of a receptor subtype-specific, $EC_{80}$-$EC_{90}$ concentration of the full agonist, carbamylcholine, either alone or in the presence of the indicated concentrations of compound.

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", and "the" include plural referents unless the context clearly dictates otherwise.

The present invention provides compounds that may function as monoamine reuptake inhibitors or as antagonists of nicotinic acetylcholine receptors, as well as methods of preparation and pharmaceutical compositions thereof. It also provides methods for using such compounds to treat a variety of disorders that may be responsive to the inhibition of monoamine reuptake or antagonism of nicotinic acetylcholine receptors. In particular, the compositions and methods can be used in the treatment of nicotine addiction and depression. Treatment can comprise the use of a compound of the present invention as a single active agent. In other embodiments, treatment can comprise the use of a compound of the present invention in combination with one or more further active agents. The specific pharmaceutical composition (or compositions) used in the invention, and the methods of treatment provided by the invention, are further described below.

DEFINITIONS

The term "alkyl" as used herein means saturated straight, branched, or cyclic hydrocarbon groups (i.e., cycloalkyl groups). In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), or 1 to 4 carbon atoms ("C1-4 alkyl"). In other embodiments, alkyl refers to groups comprising 3-10 carbon atoms ("C3-10 alkyl"), 3-8 carbon atoms ("C3-8 alkyl"), or 3-6 carbon atoms ("C3-6 alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

"Optionally substituted" in reference to a substitutent group refers to substituent groups optionally substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "alkenyl" as used herein means alkyl moieties wherein at least one saturated C—C bond is replaced by a double bond. In particular embodiments, alkenyl refers to groups comprising 2 to 10 carbon atoms ("C2-10 alkenyl"). In further embodiments, alkenyl refers to groups comprising 2 to 8 carbon atoms ("C2-8 alkenyl"), 2 to 6 carbon atoms ("C2-6 alkenyl"), or 2 to 4 carbon atoms ("C2-4 alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C—C bond is replaced by a triple bond. In particular embodiments, alkynyl refers to groups comprising 2 to 10 carbon atoms ("C2-10 alkynyl"). In further embodiments, alkynyl refers to groups comprising 2 to 8 carbon atoms ("C2-8 alkynyl"), 2 to 6 carbon atoms ("C2-6 alkynyl"), or 2 to 4 carbon atoms ("C2-4 alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The term "halo" or "halogen" as used herein means fluorine, chlorine, bromine, or iodine.

The term "alkylthio" as used herein means a thio group with one or more alkyl substituents, where alkyl is defined as above.

The term "acylamido" refers to an amide group with one or more acyl substituents, where acyl is as defined below.

The term "acyl" as used herein means a group that can be represented by C(=O)R, in which R is selected from H, alkyl; alkoxy; alkoxyalkyl including methoxymethyl; aralkyl including optionally substituted benzyl; aryloxyalkyl such as phenoxymethyl; aryl including phenyl optionally substituted with halogen, C1-C6 alkyl or C1-C6 alkoxy; sulfonate esters such as alkyl or aralkyl sulfonyl including methanesulfonyl; amino, mono-, di-, or triphosphate ester; trityl or monomethoxytrityl; trialkylsilyl such as dimethyl-t-butylsilyl or diphenylmethylsilyl.

The terms "aralkyl" and "arylalkyl" as used herein mean an aryl group as defined above linked to the molecule through an alkyl group as defined above.

The terms "alkaryl" and "alkylaryl" as used herein mean an alkyl group as defined above linked to the molecule through an aryl group as defined above.

The term "amino" as used herein means a moiety represented by the structure $NR_2$, and includes primary amines, and secondary and tertiary amines substituted by alkyl or aryl (i.e., alkylamino or arylamino, respectively). Thus, $R_2$ may represent two hydrogen atoms, two alkyl moieties, two aryl moieties, one aryl moiety and one alkyl moiety, one hydrogen atom and one alkyl moiety, or one hydrogen atom and one aryl moiety.

The term "cycloalkyl" means a non-aromatic, monocyclic or polycyclic ring comprising carbon and hydrogen atoms.

The term "aryl" as used herein means a stable monocyclic, bicyclic, or tricyclic carbon ring of up to 8 members in each ring, wherein at least one ring is aromatic as defined by the Mickel 4n+2 rule. Exemplary aryl groups according to the invention include phenyl, naphthyl, tetrahydronaphthyl, and biphenyl.

The term "heteroaryl" as used herein means an aryl group containing from one or more (particularly one to four) non-carbon atom(s) (particularly N, O, or S) or a combination thereof, which heteroaryl group is optionally substituted at one or more carbon or nitrogen atom(s) with alkyl, —$CF_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. "Substituted heteroaryl" means a heteroaryl having one or more non-interfering groups as substituents.

The term "heterocycle" or "heterocyclic" as used herein means one or more rings of at least 5 atoms, preferably 5, 6, 7, 8, 9, 10, or 11 atoms, with or without unsaturation or aromatic character and having at least one ring atom which is not carbon. Preferred heteroatoms include sulfur, oxygen, and nitrogen. Multiple rings may be fused, as in quinoline or benzofuran. "Substituted heterocycle" means a heterocycle having one or more side chains formed from non-interfering substituents.

The term "derivative" as used herein means a compound that is formed from a similar, beginning compound by attaching another molecule or atom to the beginning compound. Furthermore, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention.

The term "active metabolite" as used herein means a physiologically active compound which results from the metabolism of a compound of the invention, or a prodrug thereof, when such compound or prodrug is administered to a mammal.

The terms "therapeutically effective amount" or "therapeutically effective dose" as used herein are interchangeable and mean a concentration of a compound according to the invention, or a biologically active variant thereof, sufficient to elicit the desired therapeutic effect according to the methods of treatment described herein.

The term "pharmaceutically acceptable carrier" as used herein means a carrier that is conventionally used in the art to facilitate the storage, administration, and/or the healing effect of a biologically active agent.

The term "intermittent administration" as used herein means administration of a therapeutically effective dose of a composition according to the invention, followed by a time period of discontinuance, which is then followed by another administration of a therapeutically effective dose, and so forth.

The term "monoamine" as used herein encompasses monoamine neurotransmitters and neuromodulators. In particular, it is used to refer to dopamine, norepinephrine, and serotonin. Monoamine transporters facilitate the reuptake or reabsorption of these monoamines into the presynapses of an individual.

Active Agents

The present invention provides compounds, methods of preparation of the compounds, pharmaceutical compositions, and methods of treatment of various conditions using such compounds and pharmaceutical compositions.

In some embodiments, compounds according to the following structure are provided,

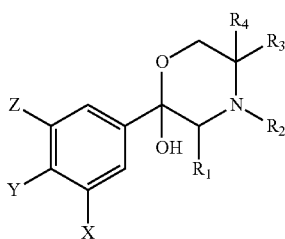

Formula I wherein:
R$_1$ is optionally substituted C1-10 alkyl;
R$_2$ is H or optionally substituted C1-10 alkyl;
R$_3$ and R$_4$ are each independently selected from optionally substituted C1-10 alkyl;
X, Y, and Z are each independently selected from H; optionally substituted C1-10 alkyl; optionally substituted C1-10 alkoxy; optionally substituted C2-10 alkenyl; optionally substituted C2-10 alkynyl; optionally substituted C6-C12 aryl including, but not limited to, phenyl and naphthyl; alkaryl; arylalkyl (including optionally substituted benzyl); aryloxy; optionally substituted heteroaryl; optionally substituted heterocycle; halo (e.g., Cl, F, Br, and I); hydroxyl; halogenated alkyl (e.g., CF$_3$, 2-Br-ethyl, CH$_2$F, CH$_2$CF$_3$, and CF$_2$CF$_3$); amino (e.g., NH$_2$, NR$_{12}$H, and NR$_{12}$R$_{13}$); alkylamino; arylamino; acyl; CN; NO$_2$; N$_3$; CH$_2$OH; CONH$_2$; CONR$_{12}$R$_{13}$; CO$_2$R$_{12}$; CH$_2$OR$_{12}$; NHCOR$_{12}$; NHCO$_2$R$_{12}$; C1-3 alkylthio; sulfate; sulfonic acid; sulfonate esters such as alkyl or aralkyl sulfonyl, including methanesulfonyl; phosphonic acid; phosphate; phosphonate; mono-, di-, or triphosphate esters; trityl or monomethoxytrityl; R$_{12}$SO; R$_{12}$SO$_2$; CF$_3$S; and CF$_3$SO$_2$; trialkylsilyl such as dimethyl-t-butylsilyl or diphenylmethylsilyl; or wherein X and Y or Y and Z form a fused aryl ring together with the phenyl ring to which X, Y, and Z are attached; and
R$_{12}$ and R$_{13}$ are each independently selected from H or optionally substituted C1-10 alkyl;
with the proviso that either (a) X is a halo substituent other than chloro (e.g., fluoro or bromo); (b) two or more of X, Y, and Z are halo substituents; (c) one or more of X, Y, and Z are optionally substituted C6-C12 aryl (e.g., phenyl); (d) X and Y or Y and Z form a fused aryl ring together with the phenyl ring to which X, Y, and Z are attached; (e) R$_1$ is an optionally substituted C2-C10 alkyl (e.g., optionally substituted ethyl, propyl, or butyl); or any combination of two or more of (a) through (e),
or a pharmaceutically acceptable ester, amide, salt, solvate, prodrug, or isomer thereof.

In certain embodiments, the invention provides a compound comprising two or more of provisos (a) through (e). For example, in some aspects, the invention provides a compound wherein X is a halo substituent other than chloro and one or both of Y and Z are halo substituents (combining (a) and (b)). In other aspects, the invention provides a compound wherein X is a halo substituent other than chloro and one or both of Y and Z is optionally substituted C6-C12 aryl (combining (a) and (c)). In other aspects, the invention provides a compound wherein X is a halo substituent other than chloro and Y and Z form a fused aryl ring together with the phenyl ring to which X, Y, and Z are attached (combining (a) and (d)). In other aspects, the invention provides a compound wherein X is a halo substituent other than chloro and R$_1$ is an optionally substituted C2-C10 alkyl (combining (a) and (e)). In still further aspects, the invention provides a compound wherein two or more of X, Y, and Z are halo substituents and one or more of X, Y, and Z are optionally substituted C6-C12 aryl (combining (b) and (c)). In other aspects, the invention provides a compound wherein two or more of X, Y, and Z are halo substituents and R$_1$ is an optionally substituted C2-C10 alkyl (combining (b) and (e)). In still further aspects, the invention provides a compound wherein one of X and Z is optionally substituted C6-C12 aryl and Y and the other of X and Z form a fused aryl ring together with the phenyl ring to which X, Y, and Z are attached (combining (c) and (d)). In other aspects, the invention provides a compound wherein one or more of X, Y, and Z are optionally substituted C6-C12 aryl and R$_1$ is an optionally substituted C2-C10 alkyl (combining (c) and (e)). In other aspects, the invention provides a compound wherein one or more of X, Y, and Z are optionally substituted C6-C12 aryl and R$_1$ is an optionally substituted C2-C10 alkyl (combining (d) and (e)).

Such compounds of the present invention may be capable of affecting monoamine uptake efficacy. In particular, in some embodiments, compounds of the present invention may be capable of inhibiting dopamine and/or norepinephrine reuptake. In some embodiments, the compounds of the present invention may be capable of acting as antagonists of one or more nicotinic acetylcholine receptors such as α4β2 nAChRs. Some compounds may act as noncompetitive functional antagonists at the α4β2 nAChRs. In certain embodiments, the compounds of the present invention may act both as inhibitors of monoamine reuptake and antagonists of the α4β2 nAChRs.

In some preferred embodiments, a compound of Formula I is provided, wherein R$_3$ and R$_4$ are each CH$_3$. In some preferred embodiments, a compound of Formula I is provided, wherein X is a halo substituent other than chloro. For example, in some preferred embodiments, a compound of Formula I is provided, wherein X is fluoro or bromo. In some preferred embodiments, a compound of Formula I is provided, wherein Y is a halo substituent. For example, in some preferred embodiments, a compound of Formula I is provided, wherein Y is chloro. In some preferred embodiments, a compound of Formula I is provided, wherein Y is optionally substituted aryl. For example, in some preferred embodiments, a compound of Formula I is provided, wherein Y is phenyl. In some preferred embodiments, a compound of Formula I is provided, wherein X and Y or Y and Z are each halo substituents. For example, in some preferred embodiments, a compound of Formula I is provided, wherein X and Y or Y and Z are both chloro. In some preferred embodiments, a compound of Formula I is provided, wherein X and Z are each halo substituents. For example, in some preferred embodiments, a compound of Formula I is provided, wherein X and Z are both fluoro. In some preferred embodiments, a compound of Formula I is provided, wherein X and Y or Y and Z form a fused aryl ring together with the phenyl ring to which X, Y, and Z are attached. For example, in some preferred embodiments, a compound of Formula I is provided, wherein X and Y or Y and Z form a 2-naphthyl ring together with the phenyl ring to which X, Y, and Z are attached. In some preferred embodiments, a compound of Formula I is provided, wherein R$_1$ is C1-10 alkyl. For example, in some preferred embodiments, a compound of Formula I is provided wherein R$_1$ is CH$_3$, C$_2$H$_5$, or C$_3$H$_7$. In other preferred embodiments, a compound of Formula I is provided wherein R$_1$ is C$_4$H$_9$, C$_5$H$_{11}$, C$_6$H$_{13}$, C$_7$H$_{15}$, C$_8$H$_{17}$, C$_9$H$_{19}$, or C$_{10}$H$_{21}$.

In some preferred embodiments, the compounds of Formula I are racemic. In some preferred embodiments, the compounds of Formula I are specific stereoisomers, with particular stereochemistries at both the carbon to which the OH and phenyl are attached and the carbon to which $R_1$ is attached. In particularly preferred embodiments, the compounds of Formula I are of the (2S-3S) configuration, although as one of skill in the art is aware, the denotation depends on the identity of the substituent represented by $R_1$. Thus, although such compounds are typically of the (2S-3S) configuration, it is possible that, depending on the identity of $R_1$, a compound may be of the (2S-3R) configuration. In some embodiments therefore, the compound of Formula I may be provided in a composition that is enantiomerically enriched, such as a mixture of enantiomers in which one enantiomer is present in excess, in particular to the extent of 95% or more, or 98% or more, including 100%. In preferred embodiments, a compound of Formula I is provided with the (2S-3S) configuration, with an enantiomeric excess of 95% or more, 96% or more, 97% or more, 98% or more, 99% or more, 99.5% or more, 99.9% or more, or 100%.

In particular embodiments, compounds according to the following structure are provided:

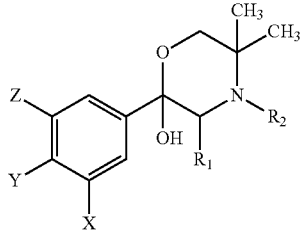

Formula Ia wherein:
$R_1$ is optionally substituted C1-10 alkyl;
$R_2$ is H or optionally substituted C1-10 alkyl;
X, Y, and Z are each independently selected from H; optionally substituted C1-10 alkyl; optionally substituted C1-10 alkoxy; optionally substituted C2-10 alkenyl; optionally substituted C2-10 alkynyl; optionally substituted C6-C12 aryl including, but not limited to, phenyl and naphthyl; alkaryl; arylalkyl (including optionally substituted benzyl); aryloxy; optionally substituted heteroaryl; optionally substituted heterocycle; halo (e.g., Cl, F, Br, and I); hydroxyl; halogenated alkyl (e.g., $CF_3$, 2-Br-ethyl, $CH_2F$, $CH_2CF_3$, and $CF_2CF_3$); amino (e.g., $NH_2$, $NR_{12}H$, and $NR_{12}R_{13}$); alkylamino; arylamino; acyl; CN; $NO_2$; $N_3$; $CH_2OH$; $CONH_2$; $CONR_{12}R_{13}$; $CO_2R_{12}$; $CH_2OR_{12}$; $NHCOR_{12}$; $NHCO_2R_{12}$; C1-3 alkylthio; sulfate; sulfonic acid; sulfonate esters such as alkyl or aralkyl sulfonyl, including methanesulfonyl; phosphonic acid; phosphate; phosphonate; mono-, di-, or triphosphate esters; trityl or monomethoxytrityl; $R_{12}SO$; $R_{12}SO_2$; $CF_3S$; and $CF_3SO_2$; trialkylsilyl such as dimethyl-t-butylsilyl or diphenylmethylsilyl; or wherein X and Y or Y and Z form a fused aryl ring together with the phenyl ring to which X, Y, and Z are attached; and
$R_{12}$ and $R_{13}$ are each independently selected from H or optionally substituted C1-10 alkyl;
with the proviso that either (a) X is a halo substituent other than chloro (e.g., fluoro or bromo); (b) two or more of X, Y, and Z are halo substituents; (c) one or more of X, Y, and Z are optionally substituted C6-C12 aryl (e.g., phenyl); (d) X and Y or Y and Z form a fused aryl ring together with the phenyl ring to which X, Y, and Z are attached; (e) $R_1$ is an optionally substituted C2-C10 alkyl (e.g., optionally substituted ethyl, propyl, or butyl); or any combination of two or more of (a) through (e),
or a pharmaceutically acceptable ester, amide, salt, solvate, prodrug, or isomer thereof.

In certain embodiments, the invention provides a compound comprising two or more of provisos (a) through (e). For example, in some aspects, the invention provides a compound wherein X is a halo substituent other than chloro and one or both of Y and Z are halo substituents (combining (a) and (b)). In other aspects, the invention provides a compound wherein X is a halo substituent other than chloro and one or both of Y and Z is optionally substituted C6-C12 aryl (combining (a) and (c)). In other aspects, the invention provides a compound wherein X is a halo substituent other than chloro and Y and Z form a fused aryl ring together with the phenyl ring to which X, Y, and Z are attached (combining (a) and (d)). In other aspects, the invention provides a compound wherein X is a halo substituent other than chloro and $R_1$ is an optionally substituted C2-C10 alkyl (combining (a) and (e)). In still further aspects, the invention provides a compound wherein two or more of X, Y, and Z are halo substituents and one or more of X, Y, and Z are optionally substituted C6-C12 aryl (combining (b) and (c)). In other aspects, the invention provides a compound wherein two or more of X, Y, and Z are halo substituents and $R_1$ is an optionally substituted C2-C10 alkyl (combining (b) and (e)). In still further aspects, the invention provides a compound wherein one of X and Z is optionally substituted C6-C12 aryl and Y and the other of X and Z form a fused aryl ring together with the phenyl ring to which X, Y, and Z are attached (combining (c) and (d)). In other aspects, the invention provides a compound wherein one or more of X, Y, and Z are optionally substituted C6-C12 aryl and $R_1$ is an optionally substituted C2-C10 alkyl (combining (c) and (e)). In other aspects, the invention provides a compound wherein one or more of X, Y, and Z are optionally substituted C6-C12 aryl and $R_1$ is an optionally substituted C2-C10 alkyl (combining (d) and (e)).

In some embodiments, compounds with one or more chiral centers are provided. While racemic mixtures of compounds of the invention can be active, selective, and bioavailable, isolated isomers may be of interest as well.

Although racemic mixtures and all possible stereoisomers are encompassed by this disclosure, in some preferred embodiments, compounds of the following formula are provided:

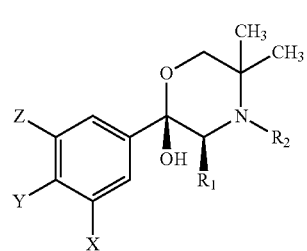

Formula Ib wherein:
$R_1$ is optionally substituted C1-10 alkyl;
$R_2$ is H or optionally substituted C1-10 alkyl;
X, Y, and Z are each independently selected from H; optionally substituted C1-10 alkyl; optionally substituted C1-10 alkoxy; optionally substituted C2-10 alkenyl; optionally substituted C2-10 alkynyl; optionally substituted C6-C12 aryl including, but not limited to, phenyl and naphthyl; alkaryl; arylalkyl (including optionally substituted benzyl); aryloxy; optionally substituted heteroaryl; optionally substituted heterocycle; halo (e.g., Cl, F, Br, and I); hydroxyl; halogenated alkyl (e.g., $CF_3$, 2-Br-ethyl, $CH_2F$, $CH_2CF_3$, and $CF_2CF_3$); amino (e.g., $NH_2$, $NR_{12}H$, and $NR_{12}R_{13}$); alkylamino; arylamino; acyl; CN; $NO_2$; $N_3$; $CH_2OH$; $CONH_2$; $CONR_{12}R_{13}$; $CO_2R_{12}$; $CH_2OR_{12}$; $NHCOR_{12}$; $NHCO_2R_{12}$; C1-3 alkylthio; sulfate; sulfonic acid; sulfonate esters such as alkyl or aralkyl sulfonyl, including methanesulfonyl; phosphonic acid; phosphate; phosphonate; mono-, di-, or triphosphate esters; trityl or monomethoxytrityl; $R_{12}SO$; $R_{12}SO_2$; $CF_3S$; and $CF_3SO_2$; trialkylsilyl such as dimethyl-t-butylsilyl or diphenylmethylsilyl; or wherein X and Y or Y and Z form a fused aryl ring together with the phenyl ring to which X, Y, and Z are attached; and $R_{12}$ and $R_{13}$ are each independently selected from H or optionally substituted C1-10 alkyl;

with the proviso that either (a) X is a halo substituent other than chloro (e.g., fluoro or bromo); (b) two or more of X, Y, and Z are halo substituents; (c) one or more of X, Y, and Z are optionally substituted C6-C12 aryl (e.g., phenyl); (d) X and Y or Y and Z form a fused aryl ring together with the phenyl ring to which X, Y, and Z are attached; (e) $R_1$ is an optionally substituted C2-C10 alkyl (e.g., optionally substituted ethyl, propyl, or butyl), or any combination of two or more of (a) through (e), or a pharmaceutically acceptable ester, amide, salt, solvate, prodrug, or isomer thereof.

In certain embodiments, the invention provides a compound comprising two or more of provisos (a) through (e). For example, in some aspects, the invention provides a compound wherein X is a halo substituent other than chloro and one or both of Y and Z are halo substituents (combining (a) and (b)). In other aspects, the invention provides a compound wherein X is a halo substituent other than chloro and one or both of Y and Z is optionally substituted C6-C12 aryl (combining (a) and (c)). In other aspects, the invention provides a compound wherein X is a halo substituent other than chloro and Y and Z form a fused aryl ring together with the phenyl ring to which X, Y, and Z are attached (combining (a) and (d)). In other aspects, the invention provides a compound wherein X is a halo substituent other than chloro and $R_1$ is an optionally substituted C2-C10 alkyl (combining (a) and (e)). In still further aspects, the invention provides a compound wherein two or more of X, Y, and Z are halo substituents and one or more of X, Y, and Z are optionally substituted C6-C12 aryl (combining (b) and (c)). In other aspects, the invention provides a compound wherein two or more of X, Y, and Z are halo substituents and $R_1$ is an optionally substituted C2-C10 alkyl (combining (b) and (e)). In still further aspects, the invention provides a compound wherein one of X and Z is optionally substituted C6-C12 aryl and Y and the other of X and Z form a fused aryl ring together with the phenyl ring to which X, Y, and Z are attached (combining (c) and (d)). In other aspects, the invention provides a compound wherein one or more of X, Y, and Z are optionally substituted C6-C12 aryl and $R_1$ is an optionally substituted C2-C10 alkyl (combining (c) and (e)). In other aspects, the invention provides a compound wherein one or more of X, Y, and Z are optionally substituted C6-C12 aryl and $R_1$ is an optionally substituted C2-C10 alkyl (combining (d) and (e)).

Compounds of Formula Ib are typically denoted as being of the (2S-3S) configuration, although as one of skill in the art is aware, the denotation depends on the identity of the substituent represented by $R_1$. Thus, although such compounds are typically of the (2S-3S) configuration, it is possible that, depending on the identity of $R_1$, a compound may be of the (2S-3R) configuration.

As indicated, the compounds disclosed herein as active agents may contain chiral centers, which may be either of the (R) or (S) configuration, or may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein and other similar tests which are well known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, such as a mixture of enantiomers in which one enantiomer is present in excess, in particular to the extent of 95% or more, or 98% or more, including 100%.

The terms (R), (S), (2R-3R), (2S-3S), (2R-3S) and (2S-3R) as used herein mean that the composition contains a greater proportion of the named isomer of the compound in relation to other isomers. In a preferred embodiment these terms indicate that the composition contains at least 90% by weight of the named isomer and 10% by weight or less of the one or more other isomers; or more preferably about 95% by weight of the named isomer and 5% or less of the one or more other isomers. These percentages are based on the total amount of the compound of the invention that is present in the composition.

The compounds of the present invention may be utilized per se or in the form of a pharmaceutically acceptable ester, amide, salt, solvate, prodrug, or isomer. For example, the compound may be provided as a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature. Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a pharmaceutically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine. The invention also includes active metabolites and other derivatives of the compounds of the invention.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound useful as an active agent according to the invention is a base, then the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound described herein as an active agent is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The present invention further includes prodrugs and active metabolites of the active agent compounds described herein. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on the free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine and/or carboxylic acid moiety. Any of these can be used in combination with the disclosed active agents to achieve a desired effect.

Particularly preferred compounds of the present invention include the following:

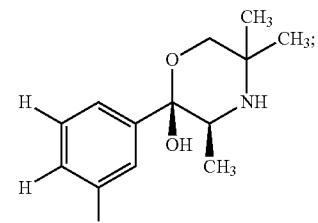

(2S,3S)-2-(3-Fluorophenyl)-3,5,5-trimethylmorpholin-2-ol

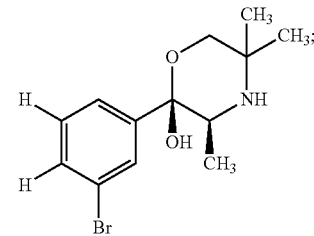

(2S,3S)-2-(3-Bromophenyl)-3,5,5-trimethylmorpholin-2-ol

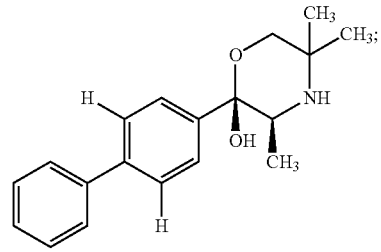

(2S,3S)-2-Biphenyl-4-yl-3,5,5-trimethylmorpholin-2-ol

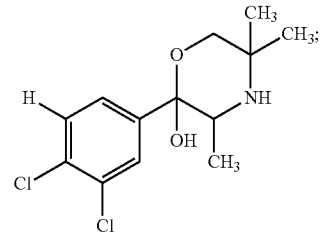

2-(3-Dichlorophenyl)-3,5,5-trimethylmorpholin-2-ol

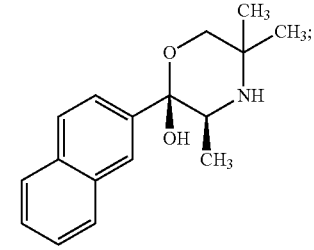

(2S,3S)-2-(Naphthalen-2-yl)-3,5,5-trimethylmorpholin-2-ol

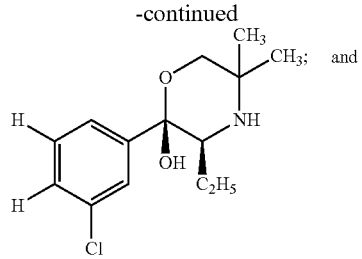

(2S,3S)-2-(3-Chlorophenyl)-3,ethyl-5,5-dimethylmorpholin-2-ol

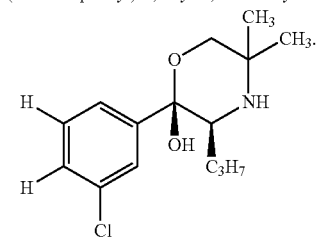

(2S,3S)-2-(3-Chlorophenyl)-5,5-dimethyl-3-propyl-morpholin-2-ol

Additional representative, non-limiting compounds of Formula I of the present invention, wherein $R_1$ is $CH_3$ and the X, Y, and Z substituents are varied are indicated below in Table 1.

TABLE 1

Representative compounds of Formula I

| X | Y | Z | $R_1$ | $R_2$ | $R_3$ | $R_4$ |
|---|---|---|---|---|---|---|
| H | H | H | $CH_3$ | H | $CH_3$ | $CH_3$ |
| Cl | H | H | $CH_3$ | H | $CH_3$ | $CH_3$ |
| H | Cl | H | $CH_3$ | H | $CH_3$ | $CH_3$ |
| Cl | Cl | H | $CH_3$ | H | $CH_3$ | $CH_3$ |
| Cl | H | Cl | $CH_3$ | H | $CH_3$ | $CH_3$ |
| Cl | Cl | Cl | $CH_3$ | H | $CH_3$ | $CH_3$ |
| F | H | H | $CH_3$ | H | $CH_3$ | $CH_3$ |
| H | F | H | $CH_3$ | H | $CH_3$ | $CH_3$ |
| F | F | H | $CH_3$ | H | $CH_3$ | $CH_3$ |
| F | H | F | $CH_3$ | H | $CH_3$ | $CH_3$ |
| F | F | F | $CH_3$ | H | $CH_3$ | $CH_3$ |
| Br | H | H | $CH_3$ | H | $CH_3$ | $CH_3$ |
| H | Br | H | $CH_3$ | H | $CH_3$ | $CH_3$ |
| Br | Br | H | $CH_3$ | H | $CH_3$ | $CH_3$ |
| Br | H | Br | $CH_3$ | H | $CH_3$ | $CH_3$ |
| Br | Br | Br | $CH_3$ | H | $CH_3$ | $CH_3$ |
| $CH_3$ | H | H | $CH_3$ | H | $CH_3$ | $CH_3$ |
| H | $CH_3$ | H | $CH_3$ | H | $CH_3$ | $CH_3$ |
| $CH_3$ | $CH_3$ | H | $CH_3$ | H | $CH_3$ | $CH_3$ |
| $CH_3$ | H | $CH_3$ | $CH_3$ | H | $CH_3$ | $CH_3$ |
| $CH_3$ | $CH_3$ | $CH_3$ | $CH_3$ | H | $CH_3$ | $CH_3$ |
| $CH_2CH_3$ | H | H | $CH_3$ | H | $CH_3$ | $CH_3$ |
| H | $CH_2CH_3$ | H | $CH_3$ | H | $CH_3$ | $CH_3$ |
| $CH_2CH_3$ | $CH_2CH_3$ | H | $CH_3$ | H | $CH_3$ | $CH_3$ |
| $CH_2CH_3$ | H | $CH_2CH_3$ | $CH_3$ | H | $CH_3$ | $CH_3$ |
| $CH_2CH_3$ | $CH_2CH_3$ | $CH_2CH_3$ | $CH_3$ | H | $CH_3$ | $CH_3$ |
| $C_3H_7$ | H | H | $CH_3$ | H | $CH_3$ | $CH_3$ |
| H | $C_3H_7$ | H | $CH_3$ | H | $CH_3$ | $CH_3$ |

TABLE 1-continued

Representative compounds of Formula I

| X | Y | Z | $R_1$ | $R_2$ | $R_3$ | $R_4$ |
|---|---|---|---|---|---|---|
| $C_3H_7$ | $C_3H_7$ | H | $CH_3$ | H | $CH_3$ | $CH_3$ |
| $C_3H_7$ | H | $C_3H_7$ | $CH_3$ | H | $CH_3$ | $CH_3$ |
| $C_3H_7$ | $C_3H_7$ | $C_3H_7$ | $CH_3$ | H | $CH_3$ | $CH_3$ |
| Cl | $CH_3$ | H | $CH_3$ | H | $CH_3$ | $CH_3$ |
| $CH_3$ | Cl | H | $CH_3$ | H | $CH_3$ | $CH_3$ |
| Cl | H | $CH_3$ | $CH_3$ | H | $CH_3$ | $CH_3$ |
| $CH_3$ | Cl | $CH_3$ | $CH_3$ | H | $CH_3$ | $CH_3$ |
| $CH_3$ | $CH_3$ | Cl | $CH_3$ | H | $CH_3$ | $CH_3$ |
| Cl | $CH_3$ | Cl | $CH_3$ | H | $CH_3$ | $CH_3$ |
| Cl | Cl | $CH_3$ | $CH_3$ | H | $CH_3$ | $CH_3$ |
| F | $CH_3$ | H | $CH_3$ | H | $CH_3$ | $CH_3$ |
| $CH_3$ | F | H | $CH_3$ | H | $CH_3$ | $CH_3$ |
| F | H | $CH_3$ | $CH_3$ | H | $CH_3$ | $CH_3$ |
| $CH_3$ | F | $CH_3$ | $CH_3$ | H | $CH_3$ | $CH_3$ |
| $CH_3$ | $CH_3$ | F | $CH_3$ | H | $CH_3$ | $CH_3$ |
| F | $CH_3$ | F | $CH_3$ | H | $CH_3$ | $CH_3$ |
| F | F | $CH_3$ | $CH_3$ | H | $CH_3$ | $CH_3$ |
| Br | $CH_3$ | H | $CH_3$ | H | $CH_3$ | $CH_3$ |
| $CH_3$ | Br | H | $CH_3$ | H | $CH_3$ | $CH_3$ |
| Br | H | $CH_3$ | $CH_3$ | H | $CH_3$ | $CH_3$ |
| $CH_3$ | Br | $CH_3$ | $CH_3$ | H | $CH_3$ | $CH_3$ |
| $CH_3$ | $CH_3$ | Br | $CH_3$ | H | $CH_3$ | $CH_3$ |
| Br | $CH_3$ | Br | $CH_3$ | H | $CH_3$ | $CH_3$ |
| Br | Br | $CH_3$ | $CH_3$ | H | $CH_3$ | $CH_3$ |
| $NO_2$ | H | H | $CH_3$ | H | $CH_3$ | $CH_3$ |
| H | $NO_2$ | H | $CH_3$ | H | $CH_3$ | $CH_3$ |
| $NO_2$ | $NO_2$ | H | $CH_3$ | H | $CH_3$ | $CH_3$ |
| $NO_2$ | H | $NO_2$ | $CH_3$ | H | $CH_3$ | $CH_3$ |
| $NO_2$ | $NO_2$ | $NO_2$ | $CH_3$ | H | $CH_3$ | $CH_3$ |
| $OCH_3$ | H | H | $CH_3$ | H | $CH_3$ | $CH_3$ |
| H | $OCH_3$ | H | $CH_3$ | H | $CH_3$ | $CH_3$ |
| $CH_3$ | $OCH_3$ | H | $CH_3$ | H | $CH_3$ | $CH_3$ |
| $OCH_3$ | H | $OCH_3$ | $CH_3$ | H | $CH_3$ | $CH_3$ |
| $OCH_3$ | $OCH_3$ | $OCH_3$ | $CH_3$ | H | $CH_3$ | $CH_3$ |
| phenyl | H | H | $CH_3$ | H | $CH_3$ | $CH_3$ |
| H | phenyl | H | $CH_3$ | H | $CH_3$ | $CH_3$ |
| phenyl | H | phenyl | $CH_3$ | H | $CH_3$ | $CH_3$ |
| phenyl | phenyl | H | $CH_3$ | H | $CH_3$ | $CH_3$ |
| phenyl | phenyl | phenyl | $CH_3$ | H | $CH_3$ | $CH_3$ |
| Cl | $CH_2CH_3$ | H | $CH_3$ | H | $CH_3$ | $CH_3$ |
| $CH_2CH_3$ | Cl | H | $CH_3$ | H | $CH_3$ | $CH_3$ |
| Cl | H | $CH_2CH_3$ | $CH_3$ | H | $CH_3$ | $CH_3$ |
| $CH_2CH_3$ | Cl | $CH_2CH_3$ | $CH_3$ | H | $CH_3$ | $CH_3$ |
| $CH_2CH_3$ | $CH_2CH_3$ | Cl | $CH_3$ | H | $CH_3$ | $CH_3$ |
| Cl | $CH_2CH_3$ | Cl | $CH_3$ | H | $CH_3$ | $CH_3$ |
| Cl | Cl | $CH_2CH_3$ | $CH_3$ | H | $CH_3$ | $CH_3$ |
| F | $CH_2CH_3$ | H | $CH_3$ | H | $CH_3$ | $CH_3$ |
| $CH_2CH_3$ | F | H | $CH_3$ | H | $CH_3$ | $CH_3$ |
| F | H | $CH_2CH_3$ | $CH_3$ | H | $CH_3$ | $CH_3$ |
| $CH_2CH_3$ | F | $CH_2CH_3$ | $CH_3$ | H | $CH_3$ | $CH_3$ |
| $CH_2CH_3$ | $CH_2CH_3$ | F | $CH_3$ | H | $CH_3$ | $CH_3$ |
| F | $CH_2CH_3$ | F | $CH_3$ | H | $CH_3$ | $CH_3$ |
| F | F | $CH_2CH_3$ | $CH_3$ | H | $CH_3$ | $CH_3$ |
| Br | $CH_2CH_3$ | H | $CH_3$ | H | $CH_3$ | $CH_3$ |
| $CH_2CH_3$ | Br | H | $CH_3$ | H | $CH_3$ | $CH_3$ |
| Br | H | $CH_2CH_3$ | $CH_3$ | H | $CH_3$ | $CH_3$ |
| $CH_2CH_3$ | Br | $CH_2CH_3$ | $CH_3$ | H | $CH_3$ | $CH_3$ |
| $CH_2CH_3$ | $CH_2CH_3$ | Br | $CH_3$ | H | $CH_3$ | $CH_3$ |
| Br | $CH_2CH_3$ | Br | $CH_3$ | H | $CH_3$ | $CH_3$ |
| Br | Br | $CH_2CH_3$ | $CH_3$ | H | $CH_3$ | $CH_3$ |
| Cl | $C_3H_7$ | H | $CH_3$ | H | $CH_3$ | $CH_3$ |
| $C_3H_7$ | Cl | H | $CH_3$ | H | $CH_3$ | $CH_3$ |
| Cl | H | $C_3H_7$ | $CH_3$ | H | $CH_3$ | $CH_3$ |
| $C_3H_7$ | Cl | $C_3H_7$ | $CH_3$ | H | $CH_3$ | $CH_3$ |

TABLE 1-continued

Representative compounds of Formula I

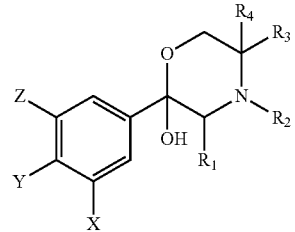

| X | Y | Z | R₁ | R₂ | R₃ | R₄ |
|---|---|---|---|---|---|---|
| C₃H₇ | C₃H₇ | Cl | CH₃ | H | CH₃ | CH₃ |
| Cl | C₃H₇ | Cl | CH₃ | H | CH₃ | CH₃ |
| Cl | Cl | C₃H₇ | CH₃ | H | CH₃ | CH₃ |
| F | C₃H₇ | H | CH₃ | H | CH₃ | CH₃ |
| C₃H₇ | F | H | CH₃ | H | CH₃ | CH₃ |
| F | H | C₃H₇ | CH₃ | H | CH₃ | CH₃ |
| C₃H₇ | F | C₃H₇ | CH₃ | H | CH₃ | CH₃ |
| C₃H₇ | C₃H₇ | F | CH₃ | H | CH₃ | CH₃ |
| F | C₃H₇ | F | CH₃ | H | CH₃ | CH₃ |
| F | F | C₃H₇ | CH₃ | H | CH₃ | CH₃ |
| Br | C₃H₇ | H | CH₃ | H | CH₃ | CH₃ |
| C₃H₇ | Br | H | CH₃ | H | CH₃ | CH₃ |
| Br | H | C₃H₇ | CH₃ | H | CH₃ | CH₃ |
| C₃H₇ | Br | C₃H₇ | CH₃ | H | CH₃ | CH₃ |
| C₃H₇ | C₃H₇ | Br | CH₃ | H | CH₃ | CH₃ |
| Br | C₃H₇ | Br | CH₃ | H | CH₃ | CH₃ |
| Br | Br | C₃H₇ | CH₃ | H | CH₃ | CH₃ |
| CH₂Cl₃ | CH₃ | H | CH₃ | H | CH₃ | CH₃ |
| CH₃ | CH₂CH₃ | H | CH₃ | H | CH₃ | CH₃ |
| CH₃ | H | CH₂CH₃ | CH₃ | H | CH₃ | CH₃ |
| CH₂CH₃ | CH₃ | CH₂CH₃ | CH₃ | H | CH₃ | CH₃ |
| CH₂CH₃ | CH₂CH₃ | CH₃ | CH₃ | H | CH₃ | CH₃ |
| CH₃ | CH₂CH₃ | CH₃ | CH₃ | H | CH₃ | CH₃ |
| CH₃ | CH₃ | CH₂CH₃ | CH₃ | H | CH₃ | CH₃ |
| CH₃ | C₃H₇ | H | CH₃ | H | CH₃ | CH₃ |
| C₃H₇ | CH₃ | H | CH₃ | H | CH₃ | CH₃ |
| CH₃ | H | C₃H₇ | CH₃ | H | CH₃ | CH₃ |
| C₃H₇ | CH₃ | C₃H₇ | CH₃ | H | CH₃ | CH₃ |
| C₃H₇ | C₃H₇ | CH₃ | CH₃ | H | CH₃ | CH₃ |
| CH₃ | C₃H₇ | CH₃ | CH₃ | H | CH₃ | CH₃ |
| CH₃ | CH₃ | C₃H₇ | CH₃ | H | CH₃ | CH₃ |
| CH₂CH₃ | C₃H₇ | H | CH₃ | H | CH₃ | CH₃ |
| C₃H₇ | CH₂CH₃ | H | CH₃ | H | CH₃ | CH₃ |
| CH₂CH₃ | H | C₃H₇ | CH₃ | H | CH₃ | CH₃ |
| C₃H₇ | CH₂CH₃ | C₃H₇ | CH₃ | H | CH₃ | CH₃ |
| C₃H₇ | C₃H₇ | CH₂CH₃ | CH₃ | H | CH₃ | CH₃ |
| CH₂CH₃ | C₃H₇ | CH₂CH₃ | CH₃ | H | CH₃ | CH₃ |
| CH₂CH₃ | CH₂CH₃ | C₃H₇ | CH₃ | H | CH₃ | CH₃ |
| CH₃ | CH₂CH₃ | C₃H₇ | CH₃ | H | CH₃ | CH₃ |
| CH₃ | C₃H₇ | CH₂CH₃ | CH₃ | H | CH₃ | CH₃ |
| CH₂CH₃ | CH₃ | C₃H₇ | CH₃ | H | CH₃ | CH₃ |
| 2-napthyl | | H | CH₃ | H | CH₃ | CH₃ |
| 2-napthyl | | Cl | CH₃ | H | CH₃ | CH₃ |
| 2-napthyl | | F | CH₃ | H | CH₃ | CH₃ |
| 2-napthyl | | Br | CH₃ | H | CH₃ | CH₃ |
| 2-napthyl | | CH₃ | CH₃ | H | CH₃ | CH₃ |
| 2-napthyl | | CH₂CH₃ | CH₃ | H | CH₃ | CH₃ |
| 2-napthyl | | C₃H₇ | CH₃ | H | CH₃ | CH₃ |
| 2-napthyl | | OCH₃ | CH₃ | H | CH₃ | CH₃ |
| 2-napthyl | | NO₂ | CH₃ | H | CH₃ | CH₃ |

Additional representative, non-limiting compounds of Formula I of the present invention, wherein $R_1$ is $CH_2CH_3$ and the X, Y, and Z substituents are varied are indicated below in Table 2.

TABLE 2

Representative compounds of Formula I

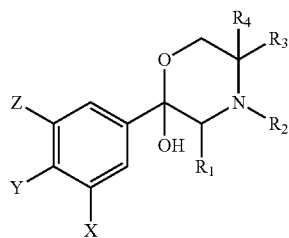

| X | Y | Z | R₁ | R₂ | R₃ | R₄ |
|---|---|---|---|---|---|---|
| H | H | H | CH₂CH₃ | H | CH₃ | CH₃ |
| Cl | H | H | CH₂CH₃ | H | CH₃ | CH₃ |
| H | Cl | H | CH₂CH₃ | H | CH₃ | CH₃ |
| Cl | Cl | H | CH₂CH₃ | H | CH₃ | CH₃ |
| Cl | H | Cl | CH₂CH₃ | H | CH₃ | CH₃ |
| Cl | Cl | Cl | CH₂CH₃ | H | CH₃ | CH₃ |
| F | H | H | CH₂CH₃ | H | CH₃ | CH₃ |
| H | F | H | CH₂CH₃ | H | CH₃ | CH₃ |
| F | F | H | CH₂CH₃ | H | CH₃ | CH₃ |
| F | H | F | CH₂CH₃ | H | CH₃ | CH₃ |
| F | F | F | CH₂CH₃ | H | CH₃ | CH₃ |
| Br | H | H | CH₂CH₃ | H | CH₃ | CH₃ |
| H | Br | H | CH₂CH₃ | H | CH₃ | CH₃ |
| Br | Br | H | CH₂CH₃ | H | CH₃ | CH₃ |
| Br | H | Br | CH₂CH₃ | H | CH₃ | CH₃ |
| Br | Br | Br | CH₂CH₃ | H | CH₃ | CH₃ |
| CH₃ | H | H | CH₂CH₃ | H | CH₃ | CH₃ |
| H | CH₃ | H | CH₂CH₃ | H | CH₃ | CH₃ |
| CH₃ | CH₃ | H | CH₂CH₃ | H | CH₃ | CH₃ |
| CH₃ | H | CH₃ | CH₂CH₃ | H | CH₃ | CH₃ |
| CH₃ | CH₃ | CH₃ | CH₂CH₃ | H | CH₃ | CH₃ |
| CH₂CH₃ | H | H | CH₂CH₃ | H | CH₃ | CH₃ |
| H | CH₂CH₃ | H | CH₂CH₃ | H | CH₃ | CH₃ |
| CH₂CH₃ | CH₂CH₃ | H | CH₂CH₃ | H | CH₃ | CH₃ |
| CH₂CH₃ | H | CH₂CH₃ | CH₂CH₃ | H | CH₃ | CH₃ |
| CH₂CH₃ | CH₂CH₃ | CH₂CH₃ | CH₂CH₃ | H | CH₃ | CH₃ |
| C₃H₇ | H | H | CH₂CH₃ | H | CH₃ | CH₃ |
| H | C₃H₇ | H | CH₂CH₃ | H | CH₃ | CH₃ |
| C₃H₇ | C₃H₇ | H | CH₂CH₃ | H | CH₃ | CH₃ |
| C₃H₇ | H | C₃H₇ | CH₂CH₃ | H | CH₃ | CH₃ |
| C₃H₇ | C₃H₇ | C₃H₇ | CH₂CH₃ | H | CH₃ | CH₃ |
| Cl | CH₃ | H | CH₂CH₃ | H | CH₃ | CH₃ |
| CH₃ | Cl | H | CH₂CH₃ | H | CH₃ | CH₃ |
| Cl | H | CH₃ | CH₂CH₃ | H | CH₃ | CH₃ |
| CH₃ | Cl | CH₃ | CH₂CH₃ | H | CH₃ | CH₃ |
| CH₃ | CH₃ | Cl | CH₂CH₃ | H | CH₃ | CH₃ |
| Cl | CH₃ | Cl | CH₂CH₃ | H | CH₃ | CH₃ |
| Cl | Cl | CH₃ | CH₂CH₃ | H | CH₃ | CH₃ |
| F | CH₃ | H | CH₂CH₃ | H | CH₃ | CH₃ |
| CH₃ | F | H | CH₂CH₃ | H | CH₃ | CH₃ |
| F | H | CH₃ | CH₂CH₃ | H | CH₃ | CH₃ |
| CH₃ | F | CH₃ | CH₂CH₃ | H | CH₃ | CH₃ |
| CH₃ | CH₃ | F | CH₂CH₃ | H | CH₃ | CH₃ |
| F | CH₃ | F | CH₂CH₃ | H | CH₃ | CH₃ |
| F | F | CH₃ | CH₂CH₃ | H | CH₃ | CH₃ |
| Br | CH₃ | H | CH₂CH₃ | H | CH₃ | CH₃ |
| CH₃ | Br | H | CH₂CH₃ | H | CH₃ | CH₃ |
| Br | H | CH₃ | CH₂CH₃ | H | CH₃ | CH₃ |
| CH₃ | Br | CH₃ | CH₂CH₃ | H | CH₃ | CH₃ |
| CH₃ | CH₃ | Br | CH₂CH₃ | H | CH₃ | CH₃ |
| Br | CH₃ | Br | CH₂CH₃ | H | CH₃ | CH₃ |
| Br | Br | CH₃ | CH₂CH₃ | H | CH₃ | CH₃ |
| NO₂ | H | H | CH₂CH₃ | H | CH₃ | CH₃ |
| H | NO₂ | H | CH₂CH₃ | H | CH₃ | CH₃ |
| NO₂ | NO₂ | H | CH₂CH₃ | H | CH₃ | CH₃ |
| NO₂ | H | NO₂ | CH₂CH₃ | H | CH₃ | CH₃ |
| NO₂ | NO₂ | NO₂ | CH₂CH₃ | H | CH₃ | CH₃ |
| OCH₃ | H | H | CH₂CH₃ | H | CH₃ | CH₃ |
| H | OCH₃ | H | CH₂CH₃ | H | CH₃ | CH₃ |
| CH₃ | OCH₃ | H | CH₂CH₃ | H | CH₃ | CH₃ |
| OCH₃ | H | OCH₃ | CH₂CH₃ | H | CH₃ | CH₃ |
| OCH₃ | OCH₃ | OCH₃ | CH₂CH₃ | H | CH₃ | CH₃ |
| phenyl | H | H | CH₂CH₃ | H | CH₃ | CH₃ |
| H | phenyl | H | CH₂CH₃ | H | CH₃ | CH₃ |

TABLE 2-continued

Representative compounds of Formula I

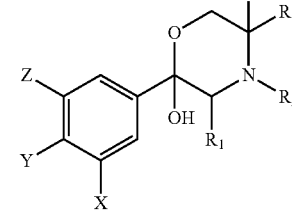

| X | Y | Z | R₁ | R₂ | R₃ | R₄ |
|---|---|---|----|----|----|----|
| phenyl | H | phenyl | CH₂CH₃ | H | CH₃ | CH₃ |
| phenyl | phenyl | H | CH₂CH₃ | H | CH₃ | CH₃ |
| phenyl | phenyl | phenyl | CH₂CH₃ | H | CH₃ | CH₃ |
| Cl | CH₂CH₃ | H | CH₂CH₃ | H | CH₃ | CH₃ |
| CH₂CH₃ | Cl | H | CH₂CH₃ | H | CH₃ | CH₃ |
| Cl | H | CH₂CH₃ | CH₂CH₃ | H | CH₃ | CH₃ |
| CH₂CH₃ | Cl | CH₂CH₃ | CH₂CH₃ | H | CH₃ | CH₃ |
| CH₂CH₃ | CH₂CH₃ | Cl | CH₂CH₃ | H | CH₃ | CH₃ |
| Cl | CH₂CH₃ | Cl | CH₂CH₃ | H | CH₃ | CH₃ |
| Cl | Cl | CH₂CH₃ | CH₂CH₃ | H | CH₃ | CH₃ |
| F | CH₂CH₃ | H | CH₂CH₃ | H | CH₃ | CH₃ |
| CH₂CH₃ | F | H | CH₂CH₃ | H | CH₃ | CH₃ |
| F | H | CH₂CH₃ | CH₂CH₃ | H | CH₃ | CH₃ |
| CH₂CH₃ | F | CH₂CH₃ | CH₂CH₃ | H | CH₃ | CH₃ |
| CH₂CH₃ | CH₂CH₃ | F | CH₂CH₃ | H | CH₃ | CH₃ |
| F | CH₂CH₃ | F | CH₂CH₃ | H | CH₃ | CH₃ |
| F | F | CH₂CH₃ | CH₂CH₃ | H | CH₃ | CH₃ |
| Br | CH₂CH₃ | H | CH₂CH₃ | H | CH₃ | CH₃ |
| CH₂CH₃ | Br | H | CH₂CH₃ | H | CH₃ | CH₃ |
| Br | H | CH₂CH₃ | CH₂CH₃ | H | CH₃ | CH₃ |
| CH₂CH₃ | Br | CH₂CH₃ | CH₂CH₃ | H | CH₃ | CH₃ |
| CH₂CH₃ | CH₂CH₃ | Br | CH₂CH₃ | H | CH₃ | CH₃ |
| Br | CH₂CH₃ | Br | CH₂CH₃ | H | CH₃ | CH₃ |
| Br | Br | CH₂CH₃ | CH₂CH₃ | H | CH₃ | CH₃ |
| Cl | C₃H₇ | H | CH₂CH₃ | H | CH₃ | CH₃ |
| C₃H₇ | Cl | H | CH₂CH₃ | H | CH₃ | CH₃ |
| Cl | H | C₃H₇ | CH₂CH₃ | H | CH₃ | CH₃ |
| C₃H₇ | Cl | C₃H₇ | CH₂CH₃ | H | CH₃ | CH₃ |
| C₃H₇ | C₃H₇ | Cl | CH₂CH₃ | H | CH₃ | CH₃ |
| Cl | C₃H₇ | Cl | CH₂CH₃ | H | CH₃ | CH₃ |
| Cl | Cl | C₃H₇ | CH₂CH₃ | H | CH₃ | CH₃ |
| F | C₃H₇ | H | CH₂CH₃ | H | CH₃ | CH₃ |
| C₃H₇ | F | H | CH₂CH₃ | H | CH₃ | CH₃ |
| F | H | C₃H₇ | CH₂CH₃ | H | CH₃ | CH₃ |
| C₃H₇ | F | C₃H₇ | CH₂CH₃ | H | CH₃ | CH₃ |
| C₃H₇ | C₃H₇ | F | CH₂CH₃ | H | CH₃ | CH₃ |
| F | C₃H₇ | F | CH₂CH₃ | H | CH₃ | CH₃ |
| F | F | C₃H₇ | CH₂CH₃ | H | CH₃ | CH₃ |
| Br | C₃H₇ | H | CH₂CH₃ | H | CH₃ | CH₃ |
| C₃H₇ | Br | H | CH₂CH₃ | H | CH₃ | CH₃ |
| Br | H | C₃H₇ | CH₂CH₃ | H | CH₃ | CH₃ |
| C₃H₇ | Br | C₃H₇ | CH₂CH₃ | H | CH₃ | CH₃ |
| C₃H₇ | C₃H₇ | Br | CH₂CH₃ | H | CH₃ | CH₃ |
| Br | C₃H₇ | Br | CH₂CH₃ | H | CH₃ | CH₃ |
| Br | Br | C₃H₇ | CH₂CH₃ | H | CH₃ | CH₃ |
| CH₂Cl₃ | CH₃ | H | CH₂CH₃ | H | CH₃ | CH₃ |
| CH₃ | CH₂CH₃ | H | CH₂CH₃ | H | CH₃ | CH₃ |
| CH₃ | H | CH₂CH₃ | CH₂CH₃ | H | CH₃ | CH₃ |
| CH₂CH₃ | CH₃ | CH₂CH₃ | CH₂CH₃ | H | CH₃ | CH₃ |
| CH₂CH₃ | CH₂CH₃ | CH₃ | CH₂CH₃ | H | CH₃ | CH₃ |
| CH₃ | CH₂CH₃ | CH₃ | CH₂CH₃ | H | CH₃ | CH₃ |
| CH₃ | CH₃ | CH₂CH₃ | CH₂CH₃ | H | CH₃ | CH₃ |
| CH₃ | C₃H₇ | H | CH₂CH₃ | H | CH₃ | CH₃ |
| C₃H₇ | CH₃ | H | CH₂CH₃ | H | CH₃ | CH₃ |
| CH₃ | H | C₃H₇ | CH₂CH₃ | H | CH₃ | CH₃ |
| C₃H₇ | CH₃ | C₃H₇ | CH₂CH₃ | H | CH₃ | CH₃ |
| C₃H₇ | C₃H₇ | CH₃ | CH₂CH₃ | H | CH₃ | CH₃ |
| CH₃ | C₃H₇ | CH₃ | CH₂CH₃ | H | CH₃ | CH₃ |
| CH₃ | CH₃ | C₃H₇ | CH₂CH₃ | H | CH₃ | CH₃ |
| CH₂CH₃ | C₃H₇ | H | CH₂CH₃ | H | CH₃ | CH₃ |
| C₃H₇ | CH₂CH₃ | H | CH₂CH₃ | H | CH₃ | CH₃ |
| CH₂CH₃ | H | C₃H₇ | CH₂CH₃ | H | CH₃ | CH₃ |
| C₃H₇ | CH₂CH₃ | C₃H₇ | CH₂CH₃ | H | CH₃ | CH₃ |
| C₃H₇ | C₃H₇ | CH₂CH₃ | CH₂CH₃ | H | CH₃ | CH₃ |
| CH₂CH₃ | C₃H₇ | CH₂CH₃ | CH₂CH₃ | H | CH₃ | CH₃ |
| CH₂CH₃ | CH₂CH₃ | C₃H₇ | CH₂CH₃ | H | CH₃ | CH₃ |
| CH₃ | CH₂CH₃ | C₃H₇ | CH₂CH₃ | H | CH₃ | CH₃ |
| CH₃ | C₃H₇ | CH₂CH₃ | CH₂CH₃ | H | CH₃ | CH₃ |
| CH₂CH₃ | CH₃ | C₃H₇ | CH₂CH₃ | H | CH₃ | CH₃ |
| 2-napthyl | | H | CH₂CH₃ | CH₂CH₃ | CH₃ | CH₃ |
| 2-napthyl | | Cl | CH₂CH₃ | H | CH₃ | CH₃ |
| 2-napthyl | | F | CH₂CH₃ | H | CH₃ | CH₃ |
| 2-napthyl | | Br | CH₂CH₃ | H | CH₃ | CH₃ |
| 2-napthyl | | CH₃ | CH₂CH₃ | H | CH₃ | CH₃ |
| 2-napthyl | | CH₂CH₃ | CH₂CH₃ | H | CH₃ | CH₃ |
| 2-napthyl | | C₃H₇ | CH₂CH₃ | H | CH₃ | CH₃ |
| 2-napthyl | | OCH₃ | CH₂CH₃ | H | CH₃ | CH₃ |
| 2-napthyl | | NO₂ | CH₂CH₃ | H | CH₃ | CH₃ |

Additional representative, non-limiting compounds of Formula I of the present invention, wherein R₁ is C₃H₇ and the X, Y, and Z substituents are varied are indicated below in Table 3.

TABLE 3

Representative compounds of Formula I

| X | Y | Z | R₁ | R₂ | R₃ | R₄ |
|---|---|---|----|----|----|----|
| H | H | H | C₃H₇ | H | CH₃ | CH₃ |
| Cl | H | H | C₃H₇ | H | CH₃ | CH₃ |
| H | Cl | H | C₃H₇ | H | CH₃ | CH₃ |
| Cl | Cl | H | C₃H₇ | H | CH₃ | CH₃ |
| Cl | H | Cl | C₃H₇ | H | CH₃ | CH₃ |
| Cl | Cl | Cl | C₃H₇ | H | CH₃ | CH₃ |
| F | H | H | C₃H₇ | H | CH₃ | CH₃ |
| H | F | H | C₃H₇ | H | CH₃ | CH₃ |
| F | F | H | C₃H₇ | H | CH₃ | CH₃ |
| F | H | F | C₃H₇ | H | CH₃ | CH₃ |
| F | F | F | C₃H₇ | H | CH₃ | CH₃ |
| Br | H | H | C₃H₇ | H | CH₃ | CH₃ |
| H | Br | H | C₃H₇ | H | CH₃ | CH₃ |
| Br | Br | H | C₃H₇ | H | CH₃ | CH₃ |
| Br | H | Br | C₃H₇ | H | CH₃ | CH₃ |
| Br | Br | Br | C₃H₇ | H | CH₃ | CH₃ |
| CH₃ | H | H | C₃H₇ | H | CH₃ | CH₃ |
| H | CH₃ | H | C₃H₇ | H | CH₃ | CH₃ |
| CH₃ | CH₃ | H | C₃H₇ | H | CH₃ | CH₃ |
| CH₃ | H | CH₃ | C₃H₇ | H | CH₃ | CH₃ |
| CH₃ | CH₃ | CH₃ | C₃H₇ | H | CH₃ | CH₃ |
| CH₂CH₃ | H | H | C₃H₇ | H | CH₃ | CH₃ |
| H | CH₂CH₃ | H | C₃H₇ | H | CH₃ | CH₃ |
| CH₂CH₃ | CH₂CH₃ | H | C₃H₇ | H | CH₃ | CH₃ |

TABLE 3-continued

Representative compounds of Formula I

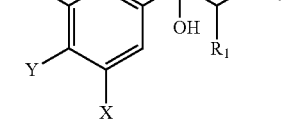

| X | Y | Z | R₁ | R₂ | R₃ | R₄ |
|---|---|---|---|---|---|---|
| CH₂CH₃ | H | CH₂CH₃ | C₃H₇ | H | CH₃ | CH₃ |
| CH₂CH₃ | CH₂CH₃ | CH₂CH₃ | C₃H₇ | H | CH₃ | CH₃ |
| C₃H₇ | H | H | C₃H₇ | H | CH₃ | CH₃ |
| H | C₃H₇ | H | C₃H₇ | H | CH₃ | CH₃ |
| C₃H₇ | C₃H₇ | H | C₃H₇ | H | CH₃ | CH₃ |
| C₃H₇ | H | C₃H₇ | C₃H₇ | H | CH₃ | CH₃ |
| C₃H₇ | C₃H₇ | C₃H₇ | C₃H₇ | H | CH₃ | CH₃ |
| Cl | CH₃ | H | C₃H₇ | H | CH₃ | CH₃ |
| CH₃ | Cl | H | C₃H₇ | H | CH₃ | CH₃ |
| Cl | H | CH₃ | C₃H₇ | H | CH₃ | CH₃ |
| CH₃ | Cl | CH₃ | C₃H₇ | H | CH₃ | CH₃ |
| CH₃ | CH₃ | Cl | C₃H₇ | H | CH₃ | CH₃ |
| Cl | CH₃ | Cl | C₃H₇ | H | CH₃ | CH₃ |
| Cl | Cl | CH₃ | C₃H₇ | H | CH₃ | CH₃ |
| F | CH₃ | H | C₃H₇ | H | CH₃ | CH₃ |
| CH₃ | F | H | C₃H₇ | H | CH₃ | CH₃ |
| F | H | CH₃ | C₃H₇ | H | CH₃ | CH₃ |
| CH₃ | F | CH₃ | C₃H₇ | H | CH₃ | CH₃ |
| CH₃ | CH₃ | F | C₃H₇ | H | CH₃ | CH₃ |
| F | CH₃ | F | C₃H₇ | H | CH₃ | CH₃ |
| F | F | CH₃ | C₃H₇ | H | CH₃ | CH₃ |
| Br | CH₃ | H | C₃H₇ | H | CH₃ | CH₃ |
| CH₃ | Br | H | C₃H₇ | H | CH₃ | CH₃ |
| Br | H | CH₃ | C₃H₇ | H | CH₃ | CH₃ |
| CH₃ | Br | CH₃ | C₃H₇ | H | CH₃ | CH₃ |
| CH₃ | CH₃ | Br | C₃H₇ | H | CH₃ | CH₃ |
| Br | CH₃ | Br | C₃H₇ | H | CH₃ | CH₃ |
| Br | Br | CH₃ | C₃H₇ | H | CH₃ | CH₃ |
| NO₂ | H | H | C₃H₇ | H | CH₃ | CH₃ |
| H | NO₂ | H | C₃H₇ | H | CH₃ | CH₃ |
| NO₂ | NO₂ | H | C₃H₇ | H | CH₃ | CH₃ |
| NO₂ | H | NO₂ | C₃H₇ | H | CH₃ | CH₃ |
| NO₂ | NO₂ | NO₂ | C₃H₇ | H | CH₃ | CH₃ |
| OCH₃ | H | H | C₃H₇ | H | CH₃ | CH₃ |
| H | OCH₃ | H | C₃H₇ | H | CH₃ | CH₃ |
| CH₃ | OCH₃ | H | C₃H₇ | H | CH₃ | CH₃ |
| OCH₃ | H | OCH₃ | C₃H₇ | H | CH₃ | CH₃ |
| OCH₃ | OCH₃ | OCH₃ | C₃H₇ | H | CH₃ | CH₃ |
| phenyl | H | H | C₃H₇ | H | CH₃ | CH₃ |
| H | phenyl | H | C₃H₇ | H | CH₃ | CH₃ |
| phenyl | H | phenyl | C₃H₇ | H | CH₃ | CH₃ |
| phenyl | phenyl | H | C₃H₇ | H | CH₃ | CH₃ |
| phenyl | phenyl | phenyl | C₃H₇ | H | CH₃ | CH₃ |
| Cl | CH₂CH₃ | H | C₃H₇ | H | CH₃ | CH₃ |
| CH₂CH₃ | Cl | H | C₃H₇ | H | CH₃ | CH₃ |
| Cl | H | CH₂CH₃ | C₃H₇ | H | CH₃ | CH₃ |
| CH₂CH₃ | Cl | CH₂CH₃ | C₃H₇ | H | CH₃ | CH₃ |
| CH₂CH₃ | CH₂CH₃ | Cl | C₃H₇ | H | CH₃ | CH₃ |
| Cl | CH₂CH₃ | Cl | C₃H₇ | H | CH₃ | CH₃ |
| Cl | Cl | CH₂CH₃ | C₃H₇ | H | CH₃ | CH₃ |
| F | CH₂CH₃ | H | C₃H₇ | H | CH₃ | CH₃ |
| CH₂CH₃ | F | H | C₃H₇ | H | CH₃ | CH₃ |
| F | H | CH₂CH₃ | C₃H₇ | H | CH₃ | CH₃ |
| CH₂CH₃ | F | CH₂CH₃ | C₃H₇ | H | CH₃ | CH₃ |
| CH₂CH₃ | CH₂CH₃ | F | C₃H₇ | H | CH₃ | CH₃ |
| F | CH₂CH₃ | F | C₃H₇ | H | CH₃ | CH₃ |
| F | F | CH₂CH₃ | C₃H₇ | H | CH₃ | CH₃ |
| Br | CH₂CH₃ | H | C₃H₇ | H | CH₃ | CH₃ |
| CH₂CH₃ | Br | H | C₃H₇ | H | CH₃ | CH₃ |
| Br | H | CH₂CH₃ | C₃H₇ | H | CH₃ | CH₃ |
| CH₂CH₃ | Br | CH₂CH₃ | C₃H₇ | H | CH₃ | CH₃ |
| CH₂CH₃ | CH₂CH₃ | Br | C₃H₇ | H | CH₃ | CH₃ |
| Br | CH₂CH₃ | Br | C₃H₇ | H | CH₃ | CH₃ |
| Br | Br | CH₂CH₃ | C₃H₇ | H | CH₃ | CH₃ |
| Cl | C₃H₇ | H | C₃H₇ | H | CH₃ | CH₃ |
| C₃H₇ | Cl | H | C₃H₇ | H | CH₃ | CH₃ |
| Cl | H | C₃H₇ | C₃H₇ | H | CH₃ | CH₃ |
| C₃H₇ | Cl | C₃H₇ | C₃H₇ | H | CH₃ | CH₃ |
| C₃H₇ | C₃H₇ | Cl | C₃H₇ | H | CH₃ | CH₃ |
| Cl | C₃H₇ | Cl | C₃H₇ | H | CH₃ | CH₃ |
| Cl | Cl | C₃H₇ | C₃H₇ | H | CH₃ | CH₃ |
| F | C₃H₇ | H | C₃H₇ | H | CH₃ | CH₃ |
| C₃H₇ | F | H | C₃H₇ | H | CH₃ | CH₃ |
| F | H | C₃H₇ | C₃H₇ | H | CH₃ | CH₃ |
| C₃H₇ | F | C₃H₇ | C₃H₇ | H | CH₃ | CH₃ |
| C₃H₇ | C₃H₇ | F | C₃H₇ | H | CH₃ | CH₃ |
| F | C₃H₇ | F | C₃H₇ | H | CH₃ | CH₃ |
| F | F | C₃H₇ | C₃H₇ | H | CH₃ | CH₃ |
| Br | C₃H₇ | H | C₃H₇ | H | CH₃ | CH₃ |
| C₃H₇ | Br | H | C₃H₇ | H | CH₃ | CH₃ |
| Br | H | C₃H₇ | C₃H₇ | H | CH₃ | CH₃ |
| C₃H₇ | Br | C₃H₇ | C₃H₇ | H | CH₃ | CH₃ |
| C₃H₇ | C₃H₇ | Br | C₃H₇ | H | CH₃ | CH₃ |
| Br | C₃H₇ | Br | C₃H₇ | H | CH₃ | CH₃ |
| Br | Br | C₃H₇ | C₃H₇ | H | CH₃ | CH₃ |
| CH₂Cl₃ | CH₃ | H | C₃H₇ | H | CH₃ | CH₃ |
| CH₃ | CH₂CH₃ | H | C₃H₇ | H | CH₃ | CH₃ |
| CH₃ | H | CH₂CH₃ | C₃H₇ | H | CH₃ | CH₃ |
| CH₂CH₃ | CH₃ | CH₂CH₃ | C₃H₇ | H | CH₃ | CH₃ |
| CH₂CH₃ | CH₂CH₃ | CH₃ | C₃H₇ | H | CH₃ | CH₃ |
| CH₃ | CH₂CH₃ | CH₃ | C₃H₇ | H | CH₃ | CH₃ |
| CH₃ | CH₃ | CH₂CH₃ | C₃H₇ | H | CH₃ | CH₃ |
| CH₃ | C₃H₇ | H | C₃H₇ | H | CH₃ | CH₃ |
| C₃H₇ | CH₃ | H | C₃H₇ | H | CH₃ | CH₃ |
| CH₃ | H | C₃H₇ | C₃H₇ | H | CH₃ | CH₃ |
| C₃H₇ | CH₃ | C₃H₇ | C₃H₇ | H | CH₃ | CH₃ |
| CH₃ | C₃H₇ | C₃H₇ | C₃H₇ | H | CH₃ | CH₃ |
| CH₃ | C₃H₇ | CH₃ | C₃H₇ | H | CH₃ | CH₃ |
| CH₃ | CH₃ | C₃H₇ | C₃H₇ | H | CH₃ | CH₃ |
| CH₂CH₃ | C₃H₇ | H | C₃H₇ | H | CH₃ | CH₃ |
| C₃H₇ | CH₂CH₃ | H | C₃H₇ | H | CH₃ | CH₃ |
| CH₂CH₃ | H | C₃H₇ | C₃H₇ | H | CH₃ | CH₃ |
| C₃H₇ | CH2CH₃ | C₃H₇ | C₃H₇ | H | CH₃ | CH₃ |
| C₃H₇ | C₃H₇ | CH₂CH₃ | C₃H₇ | H | CH₃ | CH₃ |
| CH₂CH₃ | C₃H₇ | CH₂CH₃ | C₃H₇ | H | CH₃ | CH₃ |
| CH₂CH₃ | CH₂CH₃ | C₃H₇ | C₃H₇ | H | CH₃ | CH₃ |
| CH₃ | CH₂CH₃ | C₃H₇ | C₃H₇ | H | CH₃ | CH₃ |
| CH₃ | C₃H₇ | CH₂CH₃ | C₃H₇ | H | CH₃ | CH₃ |
| CH₂CH₃ | CH₃ | C₃H₇ | C₃H₇ | H | CH₃ | CH₃ |
| 2-napthyl | | H | C₃H₇ | H | CH₃ | CH₃ |
| 2-napthyl | | Cl | C₃H₇ | H | CH₃ | CH₃ |
| 2-napthyl | | F | C₃H₇ | H | CH₃ | CH₃ |
| 2-napthyl | | Br | C₃H₇ | H | CH₃ | CH₃ |
| 2-napthyl | | CH₃ | C₃H₇ | H | CH₃ | CH₃ |
| 2-napthyl | | CH₂CH₃ | C₃H₇ | H | CH₃ | CH₃ |
| 2-napthyl | | C₃H₇ | C₃H₇ | H | CH₃ | CH₃ |
| 2-napthyl | | OCH₃ | C₃H₇ | H | CH₃ | CH₃ |
| 2-napthyl | | NO₂ | C₃H₇ | H | CH₃ | CH₃ |

In particular embodiments, the compounds of the present invention are compounds of Formula I, which include one or more of the following: R₃ and R₄ are each CH₃; X is a halo substituent other than chloro (e.g., fluoro or bromo); Y is a halo substituent (e.g., chloro); Y is optionally substituted aryl (e.g., phenyl); X and Y or Y and Z are each halo substituents (e.g., both chloro); X and Z are each halo substituents (e.g., both fluoro); X and Y or Y and Z form a fused aryl ring together with the phenyl ring to which X, Y, and Z are attached (e.g., a 2-naphthyl ring together with the phenyl ring to which X, Y, and Z are attached); $R_1$ is C1-10 alkyl (e.g., $CH_3$, $C_2H_5$, $C_3H_7$, $C_4H_9$, $C_5H_{11}$, $C_6H_{13}$, $C_7H_{15}$, $C_8H_{17}$, $C_9H_{19}$, or $C_{10}H_{21}$).

Such compounds may show enhanced monoamine transporter binding properties and may effectively inhibit monoamine uptake and/or may show enhanced activity for nAChR inhibition. In certain embodiments, the compounds of the present invention display enhanced activity in comparison to bupropion for either or both monoamine uptake inhibition and/or nAChR inhibition. In some embodiments, the compounds of the present invention show enhanced selectivity for one or more monoamine transporters (dopamine, norepinephrine, and/or serotonin transporters) and/or enhanced selectivity for one or more nAChR subtypes (e.g., α4β2). In certain embodiments, these selectivities may be enhanced in comparison to bupropion for either or both monoamine uptake inhibition and/or nAChR inhibition.

Methods of Preparation

The present invention also encompasses methods of preparing compounds with structures encompassed by Formula I, Formula Ia, and/or Formula Ib. One of skill in the art would be able to adapt these methods as required to accommodate various functional groups that may affect the chemistry of the synthesis.

Scheme 1 shows a general synthesis used for some compounds represented by Formula I of the present invention, starting with an aryl ketone. Commercially unavailable propiophenones (8) may be synthesized by Grignard additions to commercially available aryl nitriles (7). (Z)-tert-Butyldimethylsilylenol ether formation from these propiophenones, using t-butyldimethylsilyl triflate in methylene chloride yields (Z)-enol ethers. The key transformation in this sequence is a chiral Sharpless hydroxylation reaction of these enol ethers, which when using AD-mix-β, provides (R)-α-hydroxy ketones.

Scheme 2 shows a general synthesis used for some racemic compounds represented by Formula I of the present invention. The appropriate propiophenones are first synthesized by the addition of ethylmagnesium bromide to nitriles (7). Simple bromination to form the alpha-bromo ketones followed by amination with 2-amino-2-methyl-1-propanol provides the desired analogues.

In some embodiments, various compounds of the present invention may be prepared by a novel convergent synthetic approach for the preparation of 2-substituted morpholinols as outlined in Scheme 3. This approach utilizes a nucleophilic addition of Grignard reagents to (3S)-3,5,5-trimethyl-morpholin-2-one (15). Treatment of methyl (R)-(+)-lactate (13) with trifluoromethanesulfonic anhydride and 2,6-lutidine at 0° C., gives methyl (2R)-2-{[(trifluoromethyl)sulfonyl]oxy}propionate (14) in 77% yield. The alkylation of 2-amino-2-methyl-1-propanol with triflate 14 at −40° C. for 2 h and overnight at room temperature, and subsequent cyclization affords 15. The addition of the appropriate arylmagnesium bromide to 15 provides the desired compounds. The C-3 stereocenter of these compounds is derived from the lactate, rather than created by a synthetic transformation such as the Sharpless hydroxylation used in Scheme 1. In some embodiments, this center was then leveraged to create the second C-2 stereocenter. The resulting stereochemistry at C-2 was a result of either facial selectivity during the Grignard addition anti to the C-3 methyl group and/or a thermodynamic equilibrium of the final product to the S,S-configuration since the resulting product can ring open and close. The ring opened form loses its C-2 stereochemistry, forming a ketone. This route is more convergent than the Sharpless hydroxylation route, and in some embodiments, may be more reliable, requiring far less analytical work.

Scheme 4 shows a general synthesis used for some N-methylated compounds of the present invention. These may be synthesized from their non-alkylated analogues by reaction with methyl iodide in the presence of potassium carbonate.

Scheme 1[a]

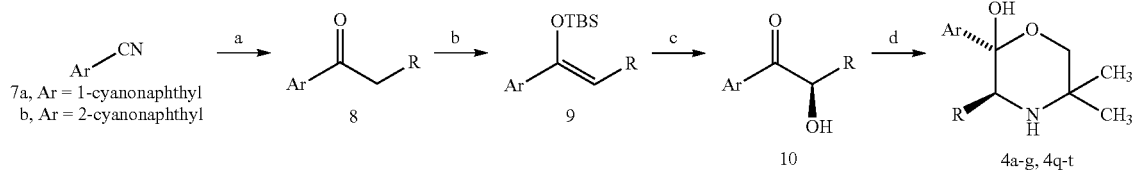

8, 9, 10a, Ar = 3-chlorophenyl, R = $CH_3$
b, Ar = 3-phenyl, R = $CH_3$
c, Ar = 3-fluorophenyl, R = $CH_3$
d, Ar = 3-bromophenyl, R = $CH_3$
e, Ar = 3-methylphenyl, R = $CH_3$
f, Ar = 3-methoxyphenyl, R = $CH_3$
g, Ar = 3-nitrophenyl, R = $CH_3$
h, Ar = 1-naphthyl, R = $CH_3$
i, Ar = 2-naphthyl, R = $CH_3$
j, Ar = 3-chlorophenyl, R = $C_2H_5$
k, Ar = 3-chlorophenyl, R = $C_2H_7$

[a]Reagents: (a) $RCH_2MgBr$; (b) TBSOTf, $CH_2Cl_2$, $Et_3N$; (c) AD-mix-β, t-BuOH/$H_2O$;
(d) $Tf_2O$, proton sponge; 2-amino-2-methyl-1-propanol, $CH_3CN$.

Scheme 2[a]

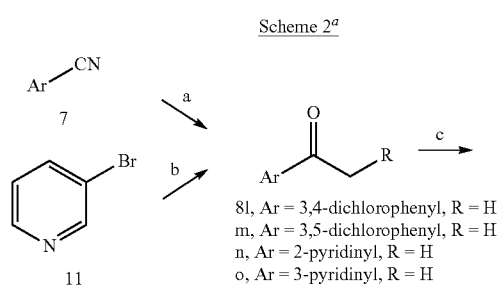

8l, Ar = 3,4-dichlorophenyl, R = H
m, Ar = 3,5-dichlorophenyl, R = H
n, Ar = 2-pyridinyl, R = H
o, Ar = 3-pyridinyl, R = H 12a, Ar = 3,4-dichlorophenyl
b, Ar = 3,5-dichlorophenyl
c, Ar = 2-pyridinyl
d, Ar = 3-pyridinyl 4n, 4p, 5, 6

[a]Reagents: (a) EtMgBr; (b) nBuLi, CH$_3$CH$_2$CN; (c) Br$_2$;
(d) 2-amino-2-methyl-1-propanol, CH$_3$CN.

Scheme 3[a]

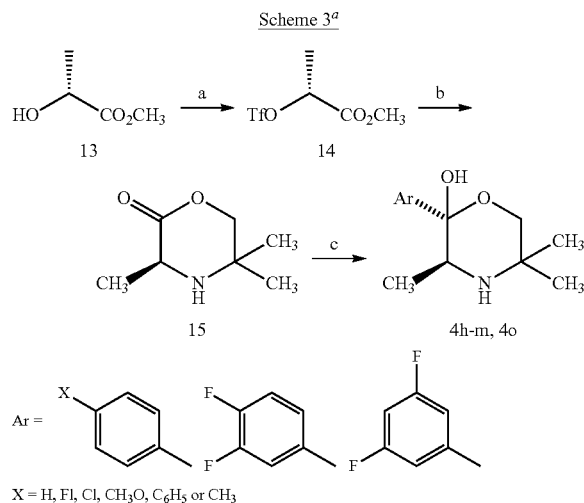

X = H, Fl, Cl, CH$_3$O, C$_6$H$_5$ or CH$_3$

[a]Reagents: (a) Tf$_2$O, 2,6-lutidine; (b) 2-amino-2-methyl-1-propanol,
CH$_2$Cl$_2$, -40 °C. to RT; (c) arylmagnesium bromide.

Scheme 4[a]

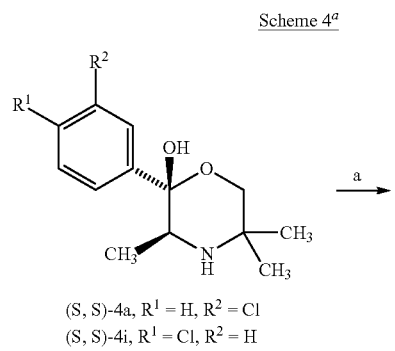

(S, S)-4a, R$^1$ = H, R$^2$ = Cl
(S, S)-4i, R$^1$ = Cl, R$^2$ = H

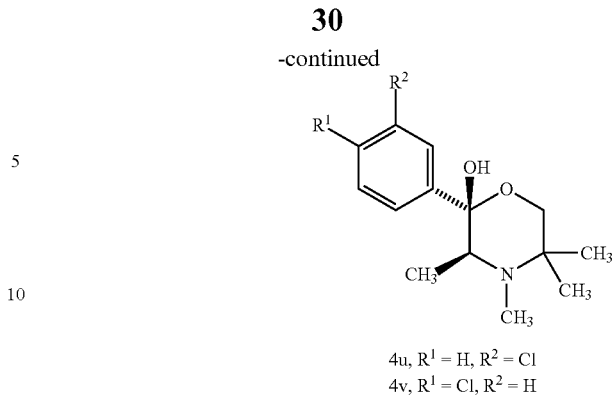

4u, R$^1$ = H, R$^2$ = Cl
4v, R$^1$ = Cl, R$^2$ = H

[a]Reagents: (a) CH$_3$I, K$_2$CO$_3$.

Compositions

While it is possible for the compounds of the present invention to be administered in the raw chemical form, it is preferred for the compounds to be delivered as a pharmaceutical formulation. Accordingly, there are provided by the present invention pharmaceutical compositions comprising at least one compound capable of inhibiting the reuptake of one or more monoamines. As such, the formulations of the present invention comprise a compound of Formula I, as described above, or a pharmaceutically acceptable ester, amide, salt, or solvate thereof, together with one or more pharmaceutically acceptable carriers therefore, and optionally, other therapeutic ingredients.

"Pharmaceutically acceptable carrier" denotes a carrier that is conventionally used in the art to facilitate the storage, administration, and/or the healing effect of the agent. The carrier(s) must be pharmaceutically acceptable in the sense of being compatible with the other ingredients of the formulation and not unduly deleterious to the recipient thereof. A carrier may also reduce any undesirable side effects of the agent. Such carriers are known in the art. See, Wang et al. (1980) *J. Parent. Drug Assn.* 34(6):452-462, herein incorporated by reference in its entirety.

Adjuvants or accessory ingredients for use in the formulations of the present invention can include any pharmaceutical ingredient commonly deemed acceptable in the art, such as binders, fillers, lubricants, disintegrants, diluents, surfactants, stabilizers, preservatives, flavoring and coloring agents, and the like. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations).

Exemplary pharmaceutical excipients and/or additives suitable for use in the compositions according to the invention are listed in Remington: The Science & Practice of Pharmacy," 21$^{st}$ ed. Lippincott Williams & Wilkins (2006); in the Physician's Desk Reference, 64$^{th}$ ed., Thomson P D R (2010); and in Handbook of Pharmaceutical Excipients, 6$^{th}$ ed., Eds. Raymond C. Rowe et al., Pharmaceutical Press (2009), which are incorporated herein by reference.

Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluloses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the formulation according to the present invention may be anionic, cationic, amphoteric, or nonionic surface active agents. Stabilizers may be included in the formulations to inhibit or lessen reactions leading to decomposition of the active agent, such as oxidative reactions.

Formulations of the present invention may include short-term, rapid-onset, rapid-offset, controlled release, sustained release, delayed release, and pulsatile release formulations, providing the formulations achieve administration of a compound as described herein. See *Remington's Pharmaceutical Sciences* (18$^{th}$ ed.; Mack Publishing Company, Eaton, Pa., 1990), herein incorporated by reference in its entirety.

Pharmaceutical formulations according to the present invention are suitable for various modes of delivery, including oral, parenteral (including intravenous, intramuscular, subcutaneous, intradermal, and transdermal), topical (including dermal, buccal, and sublingual), and rectal administration. The most useful and/or beneficial mode of administration can vary, especially depending upon the condition of the recipient and the disorder being treated.

The pharmaceutical formulations may be conveniently made available in a unit dosage form, whereby such formulations may be prepared by any of the methods generally known in the pharmaceutical arts. Generally speaking, such methods of preparation comprise combining (by various methods) an active agent, such as the compounds of Formula I according to the present invention (or a pharmaceutically acceptable ester, amide, salt, or solvate thereof) with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

Pharmaceutical formulations according to the present invention suitable as oral dosage may take various forms, such as tablets, capsules, caplets, and wafers (including rapidly dissolving or effervescing), each containing a predetermined amount of the active agent. The formulations may also be in the form of a powder or granules, a solution or suspension in an aqueous or non-aqueous liquid, and as a liquid emulsion (oil-in-water and water-in-oil). The active agent may also be delivered as a bolus, electuary, or paste. It is generally understood that methods of preparations of the above dosage forms are generally known in the art, and any such method would be suitable for the preparation of the respective dosage forms for use in delivery of the compounds according to the present invention.

A tablet containing a compound according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agent.

Solid dosage forms may be formulated so as to provide a delayed release of the active agent, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agent over a prolonged period of time), and may or may not also be delayed release. Sustained release formulations are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents. Such formulations for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compounds according to the present invention may also be administered transdermally, wherein the active agent is incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agent is contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis.

Formulations for rectal delivery of the compounds of the present invention include rectal suppositories, creams, ointments, and liquids. Suppositories may be presented as the active agent in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

The compounds of Formula I above may be formulated in compositions including those suitable for oral, buccal, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing a compound of Formula I into association with a carrier that constitutes one or more accessory ingredients. In general, the compositions are prepared by bringing a compound of the invention into association with a liquid carrier to form a solution or a suspension, or alternatively, bringing a compound of the invention into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

The amount of the compound of Formula I in the formulation will vary depending on the specific compound selected, dosage form, target patient population, and other considerations, and will be readily determined by one skilled in the art. The amount of the compound of Formula I in the formulation will be that amount necessary to deliver a therapeutically effective amount of the compound to a patient in need thereof to achieve at least one of the therapeutic effects associated with the compounds of the invention. In practice, this will vary widely depending upon the particular compound, its activity, the severity of the condition to be treated, the patient population, the stability of the formulation, and the like. Compositions will generally contain anywhere from about 1% by weight to about 99% by weight of a compound of the invention, typically from about 5% to about 70% by weight, and more typically from about 10% to about 50% by weight, and will also depend upon the relative amounts of excipients/additives contained in the composition.

Combinations

In specific embodiments, active agents used in combination with compounds of the present invention comprise one or more compounds generally recognized as useful for treating the conditions discussed herein. For example, in certain embodiments, the present invention provides a method for treating nicotine dependence/addiction.

Thus, in one embodiment, a compound of Formula I is combined with one or more nicotine substitutes for the treatment of nicotine addiction. Nicotine substitutes (also known as "nicotine replacement therapy" or "NRT") may make it easier to abstain from tobacco by partially replacing the nicotine previously obtained from tobacco. Nicotinic replacement therapies that may be combined with compounds of the present invention include, but are not limited to transdermal nicotine patches (e.g., Habitrol®, Nicoderm CQ®, and Nicotrol®), nicotine gum (e.g., Nicorette®), nicotine lozenges (e.g., Commit®), nicotine-containing sublingual tablets (e.g., Nicorette® Microtabs), and nicotine nasal sprays or inhalers.

In certain embodiments, a compound of Formula I may also be combined with one or more nicotinic drugs. One particular class of nicotinic drugs that may be used with compounds of the present invention encompasses α4-β2 nicotinic receptor partial agonists, including varenicline (Chantix®). Another nicotinic drug approved for the treatment of nicotine dependence is bupropion (Zyban®), which is an α3-β4 nicotinic receptor antagonist, and which can be combined with any of the compounds provided herein.

In some embodiments, other compounds that have demonstrated off-label success for smoking cessation may be combined with compounds of Formula I. Other drug therapies that may be prescribed and used in nicotine dependence in combination with the compounds of the present invention include nortriptyline and doxepin, both tricyclic antidepressants. Additionally, fluoxetine (Prozac®) and buspirone (Buspar®) have been used to treat nicotine addiction. Clonidine, an α2-noradrenergic agonist used to treat hypertension, has also shown beneficial effects in nicotine addiction and studies suggest that mecamylamine may also aid in treatment for nicotine addiction. Immunotherapy may also be used in conjunction with compounds of the present invention, as recent studies have demonstrated a prototype vaccine against nicotine that may induce the production of antibodies that bind nicotine in the blood, preventing it from reaching the nicotine receptors.

In some embodiments, compounds of the present invention are used in conjunction with behavioral treatment. For example, psychological treatment (including, but not limited to, psychological counseling, group therapy, and/or behavior therapy), skills training to deal with high-risk situations as well as an exercise regimen may prove effective at treating nicotine dependence when used in combination with treatment using a compound of Formula I.

Combinations of compounds of the present invention with other therapeutic agents are also included in the present invention, wherein the condition to be treated is responsive to the inhibition of monoamine reuptake and/or antagonism of nicotinic acetylcholine receptors.

For example, in some embodiments are provided methods for treating depression comprising administering a combination of a compound of Formula I and one or more known antidepressants. Antidepressants useful according to the invention include, but are not limited to, such classes of compounds as selective serotonin reuptake inhibitors (SSRIs), tricyclics, serotonin norepinephrine reuptake inhibitors (5-HT-NE dual reuptake inhibitors), and norepinephrine and dopamine reuptake inhibitors (NDRIs).

In one embodiment, compounds of Formula I may be combined with one or more compounds that are serotonin reuptake inhibitors. Serotonin reuptake inhibitors increase the extracellular level of the serotonin by inhibiting its reuptake into the presynaptic cell, which increases the level of serotonin available to bind to and stimulate the postsynaptic receptor. A significant percentage of bupropion use currently occurs in combination with one or more antidepressant drugs, most commonly by combining bupropion with one or more SSRIs. Examples of SSRIs include fluoxetine (PROZAC®) paroxetine (PAXIL®), sertraline (ZOLOFT®), citalopram (CELEXA®), escitalopram (LEXAPRO®), nefazodone (SERZONE®) and fluvoxamine (LUVOX®).

In another embodiment, compounds of Formula I may be combined with one or more compounds that at least partially inhibit the function of monoamine oxidase. Monoamine oxidase inhibitors (MAOIs) comprise a class of compounds understood to act by inhibiting the activity of monoamine oxidase, an enzyme generally found in the brain and liver of the human body, which functions to break down monoamine compounds, typically through deamination. There are two isoforms of monoamine oxidase inhibitors, MAO-A and MAO-B. The MAO-A isoform preferentially deaminates monoamines typically occurring as neurotransmitters (e.g., serotonin, melatonin, epinephrine, norepinephrine, and dopamine). Thus, MAOIs have been historically prescribed as antidepressants and for treatment of other social disorders, such as agoraphobia and social anxiety. The MAO-B isoform preferentially deaminates phenylethylamine and trace amines. Dopamine is equally deaminated by both isoforms. MAOIs may by reversible or non-reversible and may be selective for a specific isoform. For example, the MAOI moclobemide (also known as Manerix or Aurorix) is known to be approximately three times more selective for MAO-A than MAO-B.

Any compound generally recognized as being an MAOI may be useful according to the present invention. Non-limiting examples of MAOIs useful in combination with compounds of the present invention for preparing compositions according to the invention include the following: isocarboxazid (MARPLAN®); moclobemide (Aurorix, Manerix, or Moclodura); phenelzine (NARDIL®); tranylcypromine (PARNATE®); selegiline (ELDEPRYL®, EMSAM®, or 1-deprenyl); lazabemide; nialamide; iproniazid (marsilid, iprozid, ipronid, rivivol, or propilniazida); iproclozide; toloxatone; harmala; brofaromine (Consonar); benmoxin (Neuralex); and certain tryptamines, such as 5-MeO-DMT (5-Methoxy-N,N-dimethyltryptamine) or 5-MeO-AMT (5-methoxy-α-methyltryptamine).

According to still another embodiment of the invention, compounds of Formula I may be combined with one or more compounds that are norepinephrine reuptake inhibitors (NRIs). NRIs are also known as noradrenaline reuptake inhibitors (NARIs) and generally function to elevate the level of norepinephrine in the central nervous system (CNS) by inhibiting reuptake of norepinephrine from the synaptic cleft into the presynaptic neuronal terminal. Norepinephrine is a catecholamine and phenylethylamine that functions as a neurotransmitter and is known to affect many conditions. Any compound typically recognized as inhibiting the reuptake of norepinephrine in the central nervous system can be used according to the present invention. Non-limiting examples of NRIs useful according to the invention comprise atomoxetine (STRATTERA®), reboxetine (EDRONAX®, VESTRA®, or NOREBOX®), viloxazine (EMOVIT®, VIVALAN®, VIVARINT®, or VIVILAN®), maprotiline (DEPRILEPT®, LUDIOMIL®, or PSYMION®), bupropion (WELLBUTRIN® or ZYBAN®), and radafaxine.

Further non-limiting examples of specific antidepressants useful according to the invention include tricyclics such as amitriptyline, nortriptyline, and desipramine; serotonin-norepinephrine reuptake inhibitors such as venlafaxine (EFFEXOR®), duloxetine (CYMBALTA®), and milnacipran; tetracyclics such as maprotiline and mirtazapine; and other classes of compounds, including triazolopyridines such as trazodone.

The above compounds and classes of compounds are only examples of the types of active agents that can be used in combination with a compound of the present invention for the treatment of disorders that may be treated according to the present invention and are not intended to be limiting of the invention. Other disorders including other types of drug dependence, mood disorders, sleep disorders, anxiety, obesity, or attention deficit disorders may be treated with combination therapies comprising a compound of Formula I and one or more other treatments. Various further active agents can be combined with one or more compounds of the present invention according to the invention. For example, any drug generally recognized as being an antidepressant, antinarcoleptic, or ADHD treatment can be used in combination with one or more compounds of the present invention. Moreover, it is possible according to the invention to combine two or more additional active agents with a compound of the present invention for the treatment of the noted conditions.

Non-limiting examples of further active agents that can be combined with compounds of the present invention include: mood stabilizers (such as lithium, olanzipine, verapamil, quetiapine, lamotrigine, carbamazepine, valproate, oxcarbazepine, risperidone, aripiprazole, and ziprasidone); antipsychotics (such as haloperidol and other butyrophenones, chlorpromazine, fluphenazine, perphenazine, prochlorperazine, and other phenothiazines, and clozapine); serotonin receptor antagonist (5-HT2 and 5-HT3 antagonists) (such as ondansetron, tropisetron, katenserin, methysergide, cyproheptadine, and pizotifen); serotonin receptor agonists (5-HT1A receptor agonists) (such as buspirone); stimulants [such as caffeine, ADDERALL®, methylphenidate (METADATE®, RITALIN®, or CONCERTA®), pemoline (CYLERT®), or modafinil (PROVIGIL®)]; and gamma-hydroxybutyrate (GHB) (XYREM®). Although the above compounds are described in terms of classes of compounds and specific compounds, it is understood that there is substantial overlap between certain classes of compounds (such as between mood stabilizers, antipsychotics, antidepressants, and serotonin receptor antagonists). Thus, specific compounds exemplifying a specific class of compounds may also properly be identified with one or more further classes of compounds. Accordingly, the above classifications should not be viewed as limiting the scope of the types of compounds useful in combination with compounds of the present invention for treating the conditions described herein.

The compound of Formula I and the one or more other therapeutic agents may be contained within a single composition or alternatively may be administered concurrently or sequentially (consecutively) in any order. For sequential administration, each of the compound of Formula I and the one or more other therapeutic agents can be formulated in its own pharmaceutical composition, each of which is to be administered sequentially, in any order. Alternatively, the compound of Formula I and the one or more other therapeutic agents can be formulated together. The compositions may be formulated for oral, systemic, topical, intravenous, intraparenteral, intravaginal, intraocular, transbuccal, transmucosal, or transdermal administration.

Methods of Use

In a further embodiment, the present invention provides a method for treating or delaying the progression of disorders that are alleviated by inhibiting monoamine reuptake and/or antagonizing nicotinic acetylcholine receptors in a patient, the method comprising administering a therapeutically effective amount of at least one compound of Formula I to the patient. In particular, the present invention relates to the field of treating nicotine dependence in animals, particularly humans and other mammals, and associated effects of these conditions. It also may relate to the treatment of other conditions that may benefit from the inhibition of monoamine reuptake and/or antagonism of nicotinic acetylcholine receptors. It may particularly relate to the treatment of conditions that may benefit from one or more of dopamine, norepinephrine, and serotonin reuptake inhibition and/or from selective antagonism of one or more nAChR subtypes. In some embodiments, the compounds of the present invention are selective for one or more monoamine transporter. In some embodiments, the compounds show selectivity for inhibition of dopamine and norepinephrine uptake. In some embodiments, the compounds demonstrate selectivity for inhibition of dopamine over norepinephrine uptake; in other embodiments, the compounds demonstrate selectivity for inhibition of norepinephrine over dopamine uptake. However, in preferred embodiments, the compounds show greater activity for inhibiting dopamine and norepinephrine reuptake than for inhibiting serotonin reuptake. In preferred embodiments, the compounds show selectivity for one or more nAChR subtypes. In some embodiments, compounds show similar activity at both the $\alpha1\beta2$ and $\alpha1\beta4$* nAChR subtypes. In preferred embodiments, compounds are selective for one or both of the $\alpha4\beta2$ and $\alpha1\beta4$* nAChR subtypes. In particularly preferred embodiments, the compounds are selective for the $\alpha4\beta2$ nAChR subtype. Further, in some preferred embodiments, the compounds may show selectivity for both one or more monoamine transporter and one or more nAChR subtypes.

Addiction has its common meaning, e.g., the condition that exists when an individual persists in the use of a substance despite impairment or distress related to the use of the substance. In preferred embodiments, the compounds of the present invention show a slow onset and long duration of activity. These features make the compounds of the present invention particularly suitable for the treatment of addiction to abused substances, which commonly exhibit a fast onset and/or short duration of activity. Administration of the compounds of the present invention to subjects with addiction to one or more substances may be particularly suited for the treatment of nicotine, cocaine, and methamphetamine addiction.

The compounds of the present invention may also be applicable to treating depression and depressive conditions. Depression has its common meaning, e.g., a common mental disorder that presents with depressed mood, loss of interest or pleasure, feelings of guilt or low self-worth, disturbed sleep or appetite, low energy, and poor concentration or a mental state characterized by a pessimistic sense of inadequacy and a despondent lack of activity. Physical changes, such as insomnia, anorexia, weight loss, and decreased energy and libido can also occur as a result of depression. Depression includes dysthymic disorder or dysthymia, defined as a chronic low-grade depression and major depression as well as other stages or levels of depression. It also includes post-partum depression.

The compounds of the present invention may also be used for other conditions that may be responsive to inhibition of reuptake of one or more monoamines. In some embodiments, the compounds may be used to treat patients for conditions that are responsive to the inhibition of dopamine, norepinephrine, and/or serotonin. For example, in some embodiments, compounds of Formula I may be used to treat patients with bipolar disorder, attention deficit disorder (ADD), attention-deficit/hyperactivity disorder (ADHD), hypoactive sexual desire disorder, antidepressant-induced sexual dysfunction, orgasmic dysfunction, seasonal affective disorder/winter depression, obesity and food addiction, mania, bulimia and other eating disorders, panic disorders, obsessive compulsive disorder, schizophrenia, schizo-affective disorder, Parkinson's disease, narcolepsy, anxiety disorders, insomnia, chronic pain, migraine headaches, and restless legs syndrome.

The method of treatment generally includes administering a therapeutically effective amount of a compound of Formula I, optionally in a pharmaceutical composition including one or more pharmaceutically acceptable carriers. The therapeutically effective amount is preferably sufficient to inhibit the reuptake of one or more monoamines. The therapeutically effective amount is further preferably sufficient to cause some relief to the patient in the symptoms of the disorder for which the patient is being treated.

For example, in one embodiment, a method of treating nicotine addiction is provided. In such methods, a therapeutically effective amount of a compound of the present invention to treat a patient with nicotine addiction may be that amount capable of exerting some effect on the monoamine transporters and/or nicotinic acetylcholine receptors. Nicotine is thought to act in part through the activation of different nAChR subtypes, which may lead to altered neuronal electrical activity and neurotransmitter release.

A therapeutically effective amount of a compound of the present invention to treat a patient with depression may be that amount capable of providing some relief from symptoms such as changes in mood, feelings of intense sadness and despair, mental slowing, loss of concentration, pessimistic worry, agitation, and self-deprecation and/or from physical changes such as insomnia, anorexia and weight loss, and decreased energy and libido. The levels of one or more of dopamine, norepinephrine, and serotonin may be low in subjects with depression and thus, inhibition of the reuptake of any of these monoamines by the appropriate transporter may be effective to adjust the monoamine levels and treat the symptoms of depression. Some reports also indicate that nAChRs may also be implicated in patients with depression; therefore, in some embodiments, compounds according to the present invention may provide treatment for depression by acting as antagonists at one or more of the nAChR subtypes.

The therapeutically effective dosage amount of any specific formulation will vary somewhat from drug to drug, patient to patient, and will depend upon factors such as the condition of the patient and the route of delivery. When administered conjointly with other pharmaceutically active agents, even less of the compound of the invention may be therapeutically effective. Furthermore, the therapeutically effective amount may vary depending on the specific condition to be treated.

The compounds of the invention can be administered once or several times a day, or according to any other intermittent administration schedule. The daily dose can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, or by inhalation.

The compounds of the invention may be used with other types of therapy, including those which are non-drug based. For example, addiction is commonly treated using one or more therapeutics in combination with behavior therapy. Thus, in some embodiments, the methods of the present invention comprise administering to a subject a compound that that is capable of functioning as a monoamine reuptake inhibitor and/or antagonist of nAChRs in conjunction with one or more other types of non-drug-based therapy.

EXPERIMENTAL SECTION

Example 1

Synthesis

Nuclear magnetic resonance ($^1$H NMR and $^{13}$C NMR) spectra were recorded on a 300 MHz instrument (Bruker AVANCE 300) unless otherwise noted. Chemical shift data for the proton resonances were reported in parts per million (δ) relative to internal standard $(CH_3)_4Si$ (δ 0.0). Optical rotations were measured on an AutoPol III polarimeter, purchased from Rudolf Research. Elemental analyses were performed by Atlantic Microlab, Norcross, Ga. Purity of compounds (>95%) was established by elemental analyses. Analytical thin-layer chromatography (TLC) was carried out on plates precoated with silica gel GHLF (250 μM thickness). TLC visualization was accomplished with a UV lamp or in an iodine chamber or via ninhydrin staining. All moisture-sensitive reactions were performed under a positive pressure of nitrogen maintained by a direct line from a nitrogen source. Anhydrous solvents were purchased from Aldrich Chemical Co.

Certain compounds in the Experimental Section are referred to by number. The compound structure for the numbered compounds can be found, for example, in Schemes 1-4, Table 4, or in the specific synthesis examples where compound names are given. Methoxypropiophenone, 3,4-dichloropropiophenone, 3,5-dichloropropiophenone, 1-(pyridin-2-yl)propan-1-one, and 1-(pyridin-3-yl)propan-1-one, were synthesized, but are now commercially available. 3-Chlorobutyrophenone and 3-chloropentaphenone were described in an earlier paper on bupropion analogs (Carroll, F. I.; Blough, B.; Abraham, P.; Mills, A. C.; Holleman, J. A.; Wolckenhauer, S. A.; Decker, A. M.; Landavazo, A.; McElroy, K. T.; Navarro, H. A.; Gatch, M. B.; Foster, M. J., Synthesis and Biological Evaluation of Bupropion Analogues as Potential Pharmacotherapies for Cocaine Addiction. *J. Med Chem.* 2009, 52, (21), 6768-6781), incorporated herein by reference in its entirety.

Synthesis of Compounds of the Present Invention

In one embodiment, various compounds (e.g., 4a-g and 4q-t) were synthesized in a fashion similar to that reported in Fang, Q. K.; Han, Z.; Grover, P.; Kessler, D.; Senanayake, C. H.; Wald, S. A., *Tetrahedron: Asymmetry* 2000, 11, 3659-3663 for optically active 4a starting with an aryl ketone (Scheme 1). Commercially unavailable propiophenones (8) were synthesized by Grignard additions to commercially available aryl nitriles (7). (Z)-tert-Butyldimethylsilylenol ether formation from these propiophenones, (e.g., 8a-k), using t-buthyldimethylsilyl triflate in methylene chloride gave high yields of the (Z)-enol ethers (e.g., 9a-k). The key transformation in this sequence is a chiral Sharpless hydroxylation reaction of these enol ethers, which when using AD-mix-β, provided the (R)-α-hydroxy ketones 10a-k. The products of these reactions were not checked for optical purity, but were found to be optically active so optical induction was successful at some level. Due to possible epimerization throughout the process it was decided to aminate the ketone before establishing optical purity. Initial efforts to reproduce the literature preparation of (2S,3S)-4a by converting (R)-1-(3-chlorophenyl)-2-hydroxypropan-1-one (10a) to the desired product [(2S,3S)-4a] using the literature conditions with 2-amino-2-methyl-1-propanol and 2,6-lutidine failed, or was low yielding. The presence of 2,6-lutidine overwhelmed silica gel chromatography making purification difficult. A modified approach was developed using proton sponge provided (2S,3S)-4a in good yields.

In some embodiments, various compounds of the present invention (e.g., 4n and 4p, as well as 5 and 6 for comparison) were synthesized as racemic mixtures by following the standard synthesis of bupropion analogues as outlined in Kelley, J. L.; Musso, D. L.; Boswell, G. E.; Soroko, F. E.; Cooper, B. R., *J. Med. Chem.* 1996, 39, (2), 347-349, incorporated herein by reference, except substituting 2-amino-2-methyl-1-propanol for t-butylamine, shown in Scheme 2. As illustrated in Scheme 2, the appropriate propiophenones (e.g., 8l-o) were first synthesized by the addition of ethylmagnesium bromide to the nitriles (7), or in the case of the 3-pyridyl analogue was synthesized by lithium halogen exchange starting with 3-bromopyridine (11) and adding proprionitrile. Simple bromination to form the alpha-bromo ketones (e.g., 12a-d) followed by amination with 2-amino-2-methyl-1-propanol provided the desired analogues in good yield. It should be noted that the optically active syntheses of 5 and 6 were attempted using the approach in Scheme 1, but the Sharpless reaction failed to provide the desired product.

In some embodiments, various compounds of the present invention (e.g., 4h-m and 4o) were prepared by a novel convergent synthetic approach for the preparation of 2-substituted morpholinols as outlined in Scheme 3. This new approach utilized a nucleophilic addition of Grignard reagents to (3S)-3,5,5-trimethylmorpholin-2-one (15). Treatment of methyl (R)-(+)-lactate (13) with trifluoromethanesulfonic anhydride and 2,6-lutidine at 0° C., gave methyl (2R)-2-{[(trifluoromethyl)sulfonyl]oxy}propionate (14) in 77% yield. The alkylation of 2-amino-2-methyl-1-propanol with triflate 14 at −40° C. for 2 h and overnight at room temperature, and subsequent cyclization afforded 15 in 63% yield. To test the approach, reaction of lactone 15 with 3-chlorophenylmagnesium bromide resulted in the formation of (2S,3S)-trimethyl-2-(3'-chlorophenyl)morpholin-2-ol [(2S,3S)-4a] in 32% yield (98% ee), 16% overall from (R)-(+)-lactate (13). The addition of the appropriate arylmagnesium bromide to 15 provided the desired compounds (e.g., 4h-m and 4o).

The C-3 stereocenter of these compounds was derived from the lactate, not created by a synthetic transformation such as the Sharpless hydroxylation used in Scheme 1. In some embodiments, this center was then leveraged to create the second C-2 stereocenter. The resulting stereochemistry at C-2 was a result of either facial selectivity during the Grignard addition anti to the C-3 methyl group and/or a thermodynamic equilibrium of the final product to the S,S-configuration since the resulting product can ring open and close. The ring opened form loses its C-2 stereochemistry, forming a ketone. This route was more convergent than the Sharpless hydroxylation route, and was more reliable, requiring far less analytical work.

In some embodiments, N-Methylated compounds (e.g., 4u and 4v) were synthesized from their non-alkylated analogues (e.g., 4a and 4i respectively) by reaction with methyl iodide in the presence of potassium carbonate (Scheme 4).

Note that some of the compounds described herein were prepared and tested for comparison, and do not fall within the genus structure taught by the present application and thus do not fall within the invention.

Synthesis of (2S,3S)-4a Using Optically Active
Sharpless Hydroxylation Chemistry Step 1: (Z)-tert-Butyl-[1-(3-chlorophenyl)prop-1-enyloxy]dimethylsilane (9a)

In a 250-mL flask 3'-chloropropiophenone (8a, 10 g, 0.059 mol) was dissolved in 100 mL in $CH_2Cl_2$ and cooled with an ice water bath. $Et_3N$ (13 mL, 95 mmol) was added to the solution, followed by slow addition of TBDMSOTf (15 mL, 65 mmol). After stirring overnight at room temperature, the reaction mixture was diluted with $CH_2Cl_2$ and washed with $NaHCO_3$. The organic layer was separated, dried ($Na_2SO_4$) and concentrated. The oily residue was purified by column chromatography on neutral alumina using hexanes (a few drops of $Et_3N$ were added) as the eluent to give 16.4 g (98%) of title product as a colorless oil: $^1H$ NMR ($CDCl_3$) δ 7.46-7.44 (m, 1H), 7.35-7.32 (m, 1H), 7.21-7.20 (m, 2H), 5.23 (q, 1H, J=6.9 Hz), 1.73 (d, 3H, J=6.9 Hz), 0.99 (s, 9H), −0.03 (s, 6H). $C_{15}H_{23}ClOSi$.

Step 2: (R)-1-(3-Chlorophenyl)-2-hydroxypropan-1-one ((R)-10a)

A mixture of AD-mix-β (50.6 g) and $CH_3SO_2NH_2$ (3.5 g, 0.037 mol) in tert-butyl alcohol-water (120 mL/120 mL) was cooled at 0° C. and treated with 9a (10 g, 0.036 mol). The reaction mixture was stirred for 16 h at 0° C. Sodium sulfite (36 g) was added and the mixture was stirred for another hour. The mixture was filtered through a Celite pad and washed with ether. The filtrate was transferred to a separation funnel and the lower dark colored layer was discarded. The upper yellowish phase was separated, dried ($Na_2SO_4$), filtered, and concentrated. The crude product was purified by column chromatography on silica gel using hexanes-EtOAc (10:1 to 3:1) as the eluent to give 5.8 g (87%) of title product as light greenish oil: $[\alpha]^{20}_D$ +64.2° (c 1.2, $CHCl_3$); $^1H$ NMR ($CDCl_3$) δ 7.91 (s, 1H), 7.80 (d, 1H, J=7.8 Hz), 7.62-7.57 (m, 1H), 7.46 (t, 1H, J=7.8 Hz), 5.15-5.08 (m, 1H), 3.68-3.65 (m, 1H), 1.45 (d, 3H, J=7.1 Hz). $C_9H_9ClO_2$. Characterization data is similar to that reported in Fang, Q. K. et al., *Tetrahedron: Asymmetry* 2000, 11: 3659-3663.

Step 3: (2S,3S)-2-(3-Chlorophenyl)-3,5,5-trimethylmorpholin-2-ol [(2S,3S)-4a] Hemi-D-tartrate A sample of (R)-10a (2.47 g, 0.0134 mol) was added to a 250 mL flask and dissolved in $CH_2Cl_2$ (40 mL). Proton sponge (3.5 g, 0.016 mol) was added to the reaction flask, and the reaction mixture was cooled to −50° C. Triflic anhydride (2.47 mL, 14.7 mmol) was slowly added to the reaction flask, the temperature was allowed to rise to 0° C. and stirred for an additional hour. The resulting orange slurry was transferred by syringe to another flask containing a solution of 2-amino-2-methyl-1-propanol (2.6 g, 0.029 mol) in $CH_3CN$ (40 mL) at −10° C. After stirring for 4 h at 0° C., the precipitate was removed by filtration and the filtrate was concentrated. The residue was extracted with ether and solid was removed by filtration and discarded. The filtrate was concentrated to an oil. Purification of the residue by chromatography on silica gel using EtOAc with 1% $NH_4OH$ as the eluent gave 1.39 g (41%) of (2S,3S)-4a as a white solid. Characterization data is similar to data reported in Fang, Q. K.; Han, Z.; Grover, P.; Kessler, D.; Senanayake, C. H.; Wald, S. A., *Tetrahedron: Asymmetry* 2000, 11, 3659-3663.

The product freebase (1.2 g, 0.0047 mol) was dissolved in 20 mL of MeOH and treated with a solution of D-tartaric acid (350 mg, 2.30 mmol) in MeOH (3 mL). After stirring for 5 min at room temperature, the reaction mixture was concentrated, the sample dissolved in $CH_2Cl_2$ (30 mL) and MeOH was added until the solution was clear. Next, ether was added slowly until it became cloudy or small crystals started to form. After keeping the mixture at 0° C. for 1 h, the white solid was collected by filtration and recrystallized to give 0.7 g of (2S,3S)-4a.0.5D-tartrate as a white solid (ee 98.4%): mp 128-131° C.; $[\alpha]^{23}_D$ +13.7° (c 0.76, $CH_3OH$); Anal. ($C_{15}H_{21}ClNO_5$.0.5$H_2O$) calcd: C, 53.02; H, 6.53; N, 4.12. found: C, 53.12; H, 6.65; N, 4.00.

Synthesis of (2R,3R)-2-(3-Chlorophenyl)-3,5,5-trimethylmorpholin-2-ol ((2R,3R)-4a)

Following the procedure described for (2S,3S)-4a, a sample of (S)-1-(3-Chlorophenyl)-2-hydroxypropan-1-one ((S)-10a, 4.5 g, 0.024 mol), was dissolved in $CH_2Cl_2$ (75 mL) and treated with Proton sponge (6.3 g) and cooled to −50° C. Next, triflic anhydride (4.5 mL, 32 mmol) was added slowly, and the reaction mixture was stirred at 0° C. for an additional hour. The resulting orange slurry was transferred by syringe to another flask containing a solution of 2-amino-2-methyl-1-propanol, (4.7 g, 0.052 mol) in $CH_3CN$. After purification, 3.3 g (78%) of the (2R,3R)-4a was isolated and converted to 2.7 g of the Hemi-L-tartrate salt (>99% ee): mp 128-131° C.; $[\alpha]^{23}_D$ −13.0° (c 0.79, $CH_3OH$). Characterization data is similar to data reported in Fang, Q. K. et al., *Tetrahedron: Asymmetry* 2000, 11, 3659-3663.

Synthesis of (2S,3S)-2-Phenyl-3,5,5-trimethylmorpholin-2-ol (4b)

Compound 4b was synthesized by a procedure similar to that described for (2S,3S)-4a using (R)-1-phenyl-2-hydroxypropan-1-one (10b, 3.49 g, 0.0233 mol), Proton sponge (5.9 g), triflic anhydride (4.2 mL, 26 mmol), and 2-amino-2-methyl-1-propanol (4.6 g, 0.052 mol) in $CH_2Cl_2$ (50 mL). After purification by chromatography on silica gel, 3.52 g (68%) of the free base 4b was isolated, and converted to 1.19 g of the hemi-D-tartrate salt, which had >99% ee: mp 112-113° C.; $[\alpha]^{20}_D$ +15.8° (c 1.1, $CH_3OH$); $^1H$ NMR (methanol-d$_8$) δ 7.61-7.59 (m, 2H), 7.44-7.36 (m, 3H), 4.32 (s, 1H), 4.24 (d, 1H, J=12.3 Hz), 3.58-3.48 (m, 2H), 1.64 (s, 3H), 1.39 (s, 3H), 1.09 (d, 3H, J=6.6 Hz); $^{13}C$ NMR (methanol-d$_4$) δ 179.1, 142.4, 130.3, 129.6 (2C), 127.9 (2C), 97.3, 75.4, 67.4, 55.47, 55.27, 24.1, 21.3, 14.3; LCMS (ESI) m/z 222.4 (M-tartrate)$^+$; Anal. ($C_{15}H_{22}NO_5$.0.5$H_2O$) calcd: C, 59.00; H, 7.59; N, 4.59. found: C, 58.77; H, 7.46; N, 4.64.

Synthesis of (2S,3S)-2-(3-Fluorophenyl)-3,5,5-trimethylmorpholin-2-ol (4c)

Compound 4c was synthesized by a procedure similar to that described for (2S,3S)-4a using (R)-1-(3-fluorophenyl)-2-hydroxypropan-1-one (10c, 3.94 g, 0.024 mol), Proton sponge (6.0 g), triflic anhydride (4.6 mL, 25.8 mmol), and 2-amino-2-methyl-1-propanol (4.6 g, 0.052 mol) in acetonitrile (50 mL). After purification, 2.2 g (39%) of the free base 4c was isolated and converted to the hemi-D-tartrate salt, which had >99% ee: mp 131-132° C.; $[\alpha]^{20}_D$ +20.4° (c 1.0, $CH_3OH$); $^1H$ NMR (methanol-d$_4$) δ 7.45-7.41 (m, 2H), 7.35-7.31 (m, 1H), 7.11-7.09 (m, 1H), 4.33 (s, 1H), 4.26 (d, 1H, J=12.0 Hz), 3.56-3.45 (m, 2H), 1.59 (s, 3H), 1.34 (s, 3H), 1.06 (d, 3H, J=6.6 Hz); $^{13}$C NMR (methanol-d$_4$) δ 178.1, 165.4, 162.1, 144.8, 130.8, 123.2, 116.3 (d), 114.3 (d), 96.2, 74.5, 67.0, 54.3, 23.6, 20.8, 13.7; LCMS (ESI) m/z 240.0 [(M-tartrate)$^+$, M=C$_{15}$H$_{21}$FNO$_5$]; Anal. (C$_{15}$H$_{21}$FNO$_5$.0.5H$_2$O) calcd: C, 55.72; H, 6.86; N, 4.33. found: C, 55.61; H, 6.89; N, 4.33.

Synthesis of (2S,3S)-2-(3-Bromophenyl)-3,5,5-trimethylmorpholin-2-ol (4d)

Compound 4d was synthesized by a procedure similar to that described for (2S,3S)-4a using (R)-1-(3-bromophenyl)-2-hydroxypropan-1-one (10d, 4.0 g, 0.018 mol), Proton sponge (4.5 g, 0.021 mol), triflic anhydride (3.2 mL, 192 mmol), and 2-amino-2-methyl-1-propanol (3.4 g, 0.038 mol) in acetonitrile (50 mL). After purification, 2.04 g (39%) of the free base 4d was isolated and converted to 1.6 g of the hemi-D-tartrate salt, which had >99% ee: mp 129-130° C.; [α]$^{20}_D$ +9.6° (c 1.0, CH$_3$OH); $^1$H NMR (methanol-d$_4$) δ 7.77-7.76 (m, 1H), 7.63-7.53 (m, 2H), 7.38-7.32 (m, 1H), 4.37 (s, 1H), 4.14 (d, 1H, J=12.0 Hz), 3.58-3.39 (m, 2H), 1.57 (s, 3H), 1.32 (s, 3H), 1.07-1.02 (m, 3H); $^{13}$C NMR (methanol-d$_4$) δ 178.8, 145.1, 133.3, 131.1, 126.9, 123.6, 96.7, 75.2, 67.7, 55.0, 24.4, 21.5, 14.4; LCMS (ESI) m/z 300.6 [(M-tartrate)$^+$, M=C$_{15}$H$_{21}$BrNO$_5$]; Anal. (C$_{15}$H$_{21}$BrNO$_5$.0.25H$_2$O) calcd: C, 47.44; H, 5.71; N, 3.69. found: C, 47.33; H, 5.84; N, 3.63.

Synthesis of (2S,3S)-2-(m-Tolyl)-3,5,5-trimethylmorpholin-2-ol (4e)

Compound 4e was synthesized by a procedure similar to that described for (2S,3S)-4a using (R)-1-(3-methylphenyl)-2-hydroxypropan-1-one (10e, 4.2 g, 0.026 mol), Proton sponge (6.5 g, 0.030 mol), triflic anhydride (4.60 mL, 282 mmol), and 2-amino-2-methyl-1-propanol (5.0 g, 0.056 mol) in acetonitrile (55 mL). After purification, 4.0 g (66%) of the free base 4e was isolated and converted to 3.6 g of the hemi-D-tartrate salt, which had 94% ee: mp 104-105° C.; [α]$^{20}_D$ +11.9° (c 0.85, CH$_3$OH); $^1$H NMR (methanol-d$_4$) δ 7.43-7.38 (m, 2H), 7.28 (t, 1H, J=7.8 Hz), 7.21-7.18 (m, 1H), 4.33 (s, 1H), 4.20 (d, 1H, J=12.0 Hz), 3.52-3.45 (m, 2H), 2.38 (s, 3H), 1.61 (s, 3H), 1.36 (s, 3H), 1.06 (d, 3H, J=6.6 Hz); $^{13}$C NMR (methanol-d$_4$) δ 179.0, 142.3, 139.4, 130.9, 129.5, 128.4, 125.0, 97.2, 75.3, 67.4, 55.2, 24.2, 21.9, 21.4, 14.4; LCMS (ESI) m/z 236.2 [(M-tartrate)$^+$, M=C$_{16}$H$_{24}$NO$_5$]; Anal. (C$_{16}$H$_{24}$NO$_5$.0.75H$_2$O) calcd: C, 59.33; H, 7.94; N, 4.32. found: C, 59.20; H, 7.88; N, 4.34.

Synthesis of (2S,3S)-2-(3-Methoxyphenyl)-3,5,5-trimethylmorpholin-2-ol (4f)

Compound 4f was synthesized by a procedure similar to that described for (2S,3S)-4a using (R)-1-(3-methoxyphenyl)-2-hydroxypropan-1-one (10f, 4.2 g, 0.023 mol), Proton sponge (5.9 g, 0.028 mol), triflic anhydride (4.2 mL, 257 mmol), and 2-amino-2-methyl-1-propanol (4.5 g, 0.051 mol) in CH$_2$Cl$_2$ (50 mL). After purification, 4.16 g (71%) of the free base 4f was isolated and converted to 1.24 g the hemi-D-tartrate salt, which had 91% ee: mp 99-100° C.; [α]$^{20}_D$ +7.9° (c 1.1, CH$_3$OH); $^1$H NMR (methanol-d$_4$) δ 7.32 (t, 1H, J=7.8 Hz), 7.19-7.14 (m, 2H), 6.96-6.92 (m, 1H), 4.33 (s, 1H), 4.18 (d, 1H, J=12.3 Hz), 3.81 (s, 3H), 3.52 (d, 1H, J=12.3 Hz), 3.48-3.45 (m, 1H), 1.59 (s, 3H), 1.34 (s, 3H), 1.06 (d, 3H, J=6.6 Hz). $^{13}$C NMR (methanol-d$_4$) δ 178.8, 161.4, 144.1, 130.7, 120.1, 115.4, 113.8, 97.1, 75.2, 67.6, 56.1, 55.2, 24.4, 21.5, 14.5; LCMS (ESI) m/z 252.3 [(M-tartrate)$^+$, M=C$_{16}$H$_{24}$NO$_6$]; Anal. (C$_{16}$H$_{24}$NO$_6$.0.5H$_2$O) calcd: C, 57.30; H, 7.51; N, 4.18. found: C, 57.33; H, 7.55; N, 4.14.

Synthesis of (2S,3S)-2-(3-Nitrophenyl)-3,5,5-trimethylmorpholin-2-ol (4g)

Compound 4g was synthesized by a procedure similar to that described for (2S,3S)-4a using (R)-1-(3-nitrophenyl)-2-hydroxypropan-1-one (10g, 4.0 g, 0.021 mol), Proton sponge (5.2 g, 0.0246 mol), triflic anhydride (3.7 mL, 0.023 mol), and 2-amino-2-methyl-1-propanol (4.0 g, 0.045 mol) in acetonitrile (45 mL). After purification, 1.0 g (18%) of the free base 4g was isolated and converted to the hemi-D-tartrate salt, which had 94% ee: mp 192-193° C.; [α]$^{20}_D$ +6.5° (c 1.0, CH$_3$OH); $^1$H NMR (methanol-d$_4$) δ 8.47-8.25 (m, 1H), 8.31-8.26 (m, 1H), 8.05-8.01 (m, 1H), 7.73-7.66 (m, 1H), 4.34 (s, 1H), 4.18 (d, 1H, J=12.1 Hz), 3.59 (d, 1H, J=6.6 Hz), 3.50 (q, 1H, J=6.6 Hz), 1.60 (s, 3H), 1.35 (s, 3H), 1.07 (d, 3H, J=6.6 Hz); $^{13}$C NMR (methanol-d$_4$) δ 178.3, 149.9, 145.3, 134.4, 131.0, 125.0, 123.0, 96.8, 75.0, 68.1, 54.8, 24.7, 21.7, 14.6; LCMS (ESI) m/z 267.3 [(M-tartrate)$^+$, M=C$_{15}$H$_{21}$N$_2$O$_7$]; Anal. (C$_{15}$H$_{21}$N$_2$O$_7$.0.25H$_2$O) calcd: C, 52.09; H, 6.27; N, 8.10. found: C, 52.13; H, 6.22; N, 8.06.

Synthesis of (2S,3S)-2-(4-Fluorophenyl)-3,5,5-trimethylmorpholin-2-ol (4h)

A solution of 15 (166 mg, 1.16 mmol) in dry THF (1.2 mL, 1M) under an N$_2$ atmosphere was cooled to −78° C. and treated with 4-fluorophenylmagnesium bromide (1.3 equiv., 1.5 mmol, 1.9 mL, 0.8 M solution in THF). The reaction mixture was stirred at −78° C. for 3 h. A saturated aqueous solution of NH$_4$Cl was added to the reaction vessel, and the mixture was allowed to warm to room temperature. EtOAc (5 mL) was added to the reaction vessel and the organic layer was separated. The aqueous phase was extracted with EtOAc (three times). The combined organic extracts were washed (water, brine), dried (Na$_2$SO$_4$) and concentrated. The residue was purified by column chromatography on silica gel using CH$_2$Cl$_2$ to CH$_2$Cl$_2$-MeOH (90:10) as the eluent to afford 80 mg of 4h as a white solid: [α]$^{22}_D$ +31.2° (c 0.5, CHCl$_3$); $^1$H NMR (CDCl$_3$) δ 7.60-7.55 (m, 2H), δ 7.08-7.00 (m, 2H), 3.83 (d, 1H, J=11.3 Hz), 3.40 (d, 1H, J=11.3 Hz), 3.17 (q, 1H, J=6.4 Hz), 1.38 (s, 3H), 1.08 (s, 3H), 0.78 (d, 3H, J=6.4 Hz); $^{13}$C NMR (CDCl$_3$) δ 128.0, 127.9, 114.87, 114.58, 103.2, 98.4, 96.8, 69.5, 53.5, 27.3, 22.8, 16.4; LCMS (ESI) m/z 240.0 [(M+H)$^+$, M=C$_{13}$H$_{18}$FNO$_2$].

A sample of 4h (56.0 mg, 0.234 mmol) in ether (2 mL) was treated with a solution of fumaric acid (30.0 mg, 0.258 mmol) in MeOH (0.6 mL). The mixture was stirred at room temperature overnight. Filtration and washing of the filter cake with ether, followed by recrystallization of the solid from MeOH-ether gave 45 mg (54%) of 4h.0.5fumarate: mp 178-182° C.; [α]$^{22}_D$ +29° (c 0.6, MeOH); $^1$H NMR (methanol-d$_4$) δ 7.65-7.59 (m, 2H), 7.15-7.08 (m, 2H), 6.66 (s, 1H), 4.15 (d, 1H, J=12.2 Hz), 3.52 (d, 1H, J=12.2 Hz), 3.41-3.33 (m, 1H), 1.56 (s, 3H), 1.32 (s, 3H), 1.03 (d, 3H, J=6.6 Hz); $^{13}$C NMR (methanol-d$_4$) δ 136.7, 129.75, 129.64, 115.92, 115.63, 67.5, 54.8, 54.1, 24.3, 21.3, 14.3; LCMS (ESI) m/z 240.3 [(M-fumaric)$^+$, M=C$_{13}$H$_{18}$FNO$_2$.0.5C$_4$H$_4$O$_4$]; Anal. (C$_{15}$H$_{20}$FNO$_4$.H$_2$O) calcd: C, 57.13; H, 7.03; N, 4.44. found: C, 57.57; H, 6.90; N, 4.46.

Synthesis of (2S,3S)-2-(4-Chlorophenyl)-3,5,5-trimethylmorpholin-2-ol (4i)

A solution of 15 (357 mg, 2.50 mmol) in dry THF (2.5 mL, 1M) under an $N_2$ atmosphere was cooled to −78° C. and treated with 4-chlorophenylmagnesium bromide (2 equiv., 5.00 mmol, 5.00 mL, 1M solution in ether). The reaction mixture was stirred at −78° C. for 2 h. A saturated aqueous solution of $NH_4Cl$ was added to the reaction vessel, and the mixture was allowed to warm to room temperature. EtOAc was added and the organic layer was separated and the aqueous phase was extracted with EtOAc (trice). The combined organic extracts were washed (water, brine), dried ($Na_2SO_4$) and concentrated. The residue was purified by column chromatography on silica gel using $CH_2Cl_2$ to $CH_2Cl_2$-MeOH (90:10) as the eluent to afford 180 mg (29%) of 4i as a white solid: $[\alpha]^{23}_D$ +33° (c 0.4, $CHCl_3$): $^1H$ NMR ($CDCl_3$) δ 7.54 (d, 2H, J=8.5 Hz), 7.32 (d, 2H, J=8.5 Hz), 3.83 (d, 1H, J=11.3 Hz), 3.40 (d, 1H, J=11.3 Hz), 3.18 (q, 1H, J=6.5 Hz), 1.38 (s, 3H), 1.08 (s, 3H), 0.78 (d, 3H, J=6.5 Hz); $^{13}C$ NMR ($CDCl_3$) δ 128.5, 128.1, 127.6, 127.2, 101.6, 95.9, 69.5, 53.4, 49.7, 27.3, 22.8, 16.4; LCMS (ESI) m/z 256.3 [(M+H)$^+$, M=$C_{13}H_{18}ClNO_2$].

A sample of 4i (161 mg, 0.629 mmol) in ether (3 mL) was treated with a solution of fumaric acid (73.0 mg, 0.629 mmol) in MeOH (1.2 mL). The mixture was stirred at room temperature overnight. Filtration and washing of the filter cake with ether, followed by recrystallization from MeOH-ether gave 123 mg (53%) of 4i.0.5fumarate as a white solid; mp 187-190° C.; $[\alpha]^{22}_D$ +22° (c 0.75, MeOH); $^1H$ NMR (methanol-$d_4$) δ 7.58 (d, 2H, J=8.6 Hz), 7.41 (d, 1H, J=8.6 Hz), 6.67 (s, 1H), 4.11 (d, 1H, J=12.0 Hz), 3.51 (d, 1H, J=12.0 Hz), 3.38-3.36 (m, 1H), 1.53 (s, 3H), 1.28 (s, 3H), 1.00 (d, 3H, J=6.6 Hz); $^{13}C$ NMR (methanol-$d_4$) δ 172.9, 141.1, 136.7, 135.8, 129.3, 96.6, 67.4, 54.68, 54.37, 24.1, 21.2, 14.1; LCMS (ESI) m/z 256.6 [(M-fumaric)$^+$, M=$C_{13}H_{18}ClNO_2$.0.5$C_4H_4O_4$]; Anal. ($C_{15}H_{20}ClNO_4$.0.5$H_2O$) calcd: C, 55.81; H, 6.56; N, 4.34. found: C, 55.84; H, 6.58; N, 4.13.

Synthesis of (2S,3S)-3,5,5-Trimethyl-2-(4-methylphenyl)morpholin-2-ol (4j)

A solution of morpholin-2-one 15 (270 mg, 1.88 mmol) in anhydrous THF (1.9 mL) was cooled to −78° C. and treated with p-tolylmagnesium bromide (1.2 equiv., 2.26 mmol, 2.26 mL, 1 M solution in THF) under an $N_2$ atmosphere. After stirring the reaction mixture at −78° C. for 1.5 h, saturated aqueous solution of $NH_4Cl$ (30 mL) was added to the reaction vessel, and the mixture was allowed to warm to room temperature. Ether (30 mL) was added to the reaction flask, the organic layer was separated. The aqueous phase was extracted with ether (twice). The combined organic extracts were washed (water, brine), dried ($Na_2SO_4$) and concentrated. The residue was purified by column chromatography on silica gel using $CH_2Cl_2$ to $CH_2Cl_2$-MeOH (90:10) as the eluent to give 271 mg (41%) of 4j as a yellow foam: $[\alpha]^{22}_D$ +21.2° (c 0.9, $CHCl_3$); $^1H$ NMR ($CDCl_3$) δ 7.47 (d, 2H, J=8.2 Hz), 7.16 (d, 2H, J=8.0 Hz), 3.85 (d, 1H, J=11.3 Hz), 3.40 (d, 1H, J=11.2 Hz), 3.20-3.07 (m, 1H), 2.35 (s, 3H), 1.39 (s, 3H), 1.08 (s, 3H), 0.81 (d, 3H, J=6.5 Hz); $^{13}C$ NMR ($CDCl_3$) δ 129.6, 128.60, 128.49, 125.9, 103.2, 96.2, 69.4, 53.9, 53.4, 49.6, 27.3, 22.8, 16.5; LCMS (ESI) m/z 236.3 [(M+H)$^+$, M=$C_{14}H_{21}NO_2$].

A sample of 4j (240 mg, 0.683 mmol) in ether (3 mL) was treated with a solution of fumaric acid (87.0 mg, 0.751 mmol) in MeOH (2 mL) and stirred at room temperature overnight. Ether was added to the reaction mixture. The solid was recrystallized from MeOH-ether to give 140 mg (67%) of 4j.0.5fumarate as a white solid: mp 178-182° C.; $[\alpha]^{22}_D$ +19° (c 0.6, MeOH); $^1H$ NMR (methanol-$d_4$) δ 7.47 (d, 2H, J=8.2 Hz), 7.21 (d, 2H, J=8.0 Hz), 6.65 (s, 1H), 4.18 (d, 1H, J=12.2 Hz), 3.51 (d, 1H, J=12.2 Hz), 3.46 (q, 1H, J=6.6 Hz), 2.35 (s, 3H), 1.58 (s, 3H), 1.34 (s, 3H), 1.04 (d, 1H, J=6.6 Hz); $^{13}C$ NMR (methanol-$d_4$) δ 139.9, 139.2, 136.9, 129.8, 127.4, 96.8, 67.2, 54.9, 54.6, 24.1, 21.1, 14.1; LCMS (ESI) m/z 236.2 [(M-fumaric)$^+$ $C_{14}H_{21}NO_2$.0.5$C_4H_4O_4$]; Anal. ($C_{16}H_{23}NO_4$.0.25$H_2O$) calcd: C, 64.52; H, 7.95; N, 4.70. found: C, 64.56; H, 7.76; N, 4.65.

Synthesis of (2S,3S)-2-(4-Methoxyphenyl)-3,5,5-trimethylmorpholin-2-ol (4k)

A solution of 15 (434 mg, 3.03 mmol) in anhydrous THF (3 mL, 1M) was cooled to −78° C. and treated with 4-methoxyphenylmagnesium bromide (1.3 equiv., 3.93 mmol, 3.9 mL of 1 M solution in THF). The reaction mixture was stirred at −78° C. and under an $N_2$ atmosphere for 1.5 h. A saturated aqueous solution of $NH_4Cl$ (30 mL) was added to the reaction vessel, and the mixture was allowed to warm to room temperature. The mixture was extracted with ether (three times). The combined ether extracts were washed (water, brine), dried ($Na_2SO_4$) and concentrated. The residue was purified by column chromatography on silica gel using $CH_2Cl_2$ to $CH_2Cl_2$-MeOH—$NH_4OH$ (90:9:1) as the eluent to give 380 mg of a yellow solid.

The sample (379 mg, 0.783 mmol) in ether (5 mL) was treated with HCl (1.00 mmol, 0.250 mL, 4 M solution in dioxane). The mixture was stirred at room temperature overnight. Ether was added to the reaction mixture. The suspension was sonicated, centrifuged, and decanted three times to afford a solid pellet. The solid material was recrystallized from MeOH-ether to give 215 mg (95%) of 4k.HCl as a pale yellow solid: mp 170-172° C.; $[\alpha]^{20}_D$ +19.6° (c 1.0, MeOH). NMR (methanol-$d_4$) δ 7.52 (d, 2H, J=8.9 Hz), 6.95 (d, 2H, J=8.9 Hz), 4.22 (d, 1H, J=12.4 Hz), 3.81 (s, 3H), 3.58-3.45 (m, 2H), 1.62 (s, 3H), 1.39 (s, 3H), 1.10 (d, 3H, J=6.6 Hz); $^{13}C$ NMR (methanol-$d_4$) δ 161.8, 133.5, 132.8, 128.8, 114.6, 96.7, 66.6, 55.80, 55.7, 55.2, 23.4, 20.8, 13.7; LCMS (ESI) m/z 286.4 (M−H)$^+$, M=$C_{14}H_{21}NO_3$.HCl]; Anal. ($C_{14}H_{22}ClNO_3$) calcd: C, 58.43; H, 7.71; N, 4.87. found: C, 58.42; H, 7.83; N, 4.81.

Synthesis of (2S,3S)-2-Biphenyl-4-yl-3,5,5-trimethylmorpholin-2-ol (4l)

A solution of 15 (394 mg, 2.75 mmol) in anhydrous THF (2.75 mL, 1M) was cooled to −78° C. and treated with 4-biphenylmagnesium bromide (1.2 equiv., 3.30 mmol, 6.60 mL, 0.5 M solution in THF) under an $N_2$ atmosphere. After stirring at −78° C. for 1.5 h, the reaction mixture was treated with saturated aqueous solution of $NH_4Cl$ (40 mL) and EtOAc was added (30 mL). The organic layer was separated. The aqueous phase was extracted with EtOAc trice. The combined organic extracts were washed (water, brine), dried ($Na_2SO_4$) and concentrated. Purification of the residue by column chromatography on silica gel using $CH_2Cl_2$ to $CH_2Cl_2$-MeOH (90:10) as the eluent afforded 300 mg (37%) of 4l as a white solid: $[\alpha]^{23}_D$ +15.2° (c 0.3, $CHCl_3$); $^1H$ NMR ($CDCl_3$) δ 7.70-7.33 (m, 9H), 3.88 (d, 1H, J=11.3 Hz), 3.44 (d, 1H, J=11.3 Hz), 3.29-3.25 (m, 1H), 1.42 (s, 3H), 1.10 (s, 3H), 0.86 (d, 3H, J=6.5 Hz); $^{13}C$ NMR ($CDCl_3$) δ 140.9, 129.0, 128.97, 128.74, 128.4, 127.54, 127.30, 127.13, 126.7, 126.5, 96.2, 69.5, 53.4, 51.4, 49.6, 27.4, 22.8, 16.6; LCMS (ESI) m/z 298.4, 280.3 [(M+H)$^+$, M=$C_{19}H_{23}NO_2$].

A sample of 4l (379 mg, 1.27 mmol) in $CH_2Cl_2$ (4 mL) was treated with a solution of fumaric acid (148 mg, 1.27 mmol) in MeOH (4 mL). The mixture was stirred at room temperature overnight. Filtration and washing of the filter cake with ether, followed by recrystallization from MeOH-ether gave 130 mg (25%) of 4l.0.5fumarate as a white solid: mp 197-202° C. $[\alpha]^{22}_D$ +18° (c 1.6, MeOH); $^1$H NMR (methanol-$d_4$) δ 7.70-7.63 (m, 6H), 7.49-7.35 (m, 3H), 6.69 (s, 1H), 4.20 (d, 1H, J=12.1 Hz), 3.55 (d, 1H, J=12.1 Hz), 3.47 (q, 1H, J=6.7 Hz), 1.60 (s, 3H), 1.34 (s, 3H), 1.08 (d, 3H, J=6.6 Hz); $^{13}$C NMR (methanol-$d_4$) δ 142.9, 141.8, 141.4, 136.7, 129.9, 128.6, 128.04, 128.02, 127.7, 96.9, 67.5, 54.8, 54.1, 30.7, 24.4, 21.3, 14.4; LCMS (ESI) m/z 298.6, 280.3 [(M-fumaric)$^+$, M=$C_{19}H_{23}NO_2$.0.5$C_4H_4O_4$]; Anal ($C_{21}H_{25}NO_4$.0.75$H_2O$) calcd: C, 68.36; H, 7.24; N, 3.80. found: C, 68.59; H, 7.22; N, 3.76.

Synthesis of (2S,3S)-2-(3,4-Difluorophenyl)-3,5,5-trimethylmorpholin-2-ol (4m)

A solution of morpholin-2-one 15 (410 mg, 2.86 mmol) in anhydrous THF (2.9 mL, 1M) was cooled to −78° C. and treated with 3,4-difluorophenylmagnesium bromide (1.2 equiv., 3.43 mmol, 6.90 mL, 0.5 M solution in THF) under an $N_2$ atmosphere. After stirring the reaction mixture at −78° C. under an inert atmosphere for 1.5 h, saturated aqueous solution of $NH_4Cl$ was added to the reaction vessel. The reaction mixture was allowed to warm to room temperature and extracted with ether (three times). The combined organic extracts were washed (water, brine), dried ($Na_2SO_4$) and concentrated. Purification of the residue by column chromatography on silica gel using $CH_2Cl_2$ to $CH_2Cl_2$-MeOH—$NH_4OH$ (90:9:1) as the eluent gave 190 mg (25%) of 4m as a yellow solid: $[\alpha]^{22}_D$ +18.2° (c 1.0, CHCl$_3$); $^1$H NMR (CDCl$_3$) δ 7.45-7.39 (m, 1H), 7.34-7.32 (m, 1H), 7.18-7.10 (m, 1H), 3.82 (d, 1H, J=11.3 Hz), 3.40 (d, 1H, J=11.3 Hz), 3.18 (q, 1H, J=6.5 Hz), 1.38 (s, 3H), 1.08 (s, 3H), 0.78 (d, 3H, J=6.5 Hz); $^{13}$C NMR (CDCl$_3$) δ 122.40, 122.31 116.74, 116.51, 115.8, 115.6, 96.5, 69.6, 53.4, 49.8, 27.3, 22.8, 16.5; LCMS (ESI) m/z 258.6, [(M+H)$^+$, M=$C_{13}H_{17}F_2NO_2$].

A sample of 4m (180 mg, 0.699 mmol) in ether (3 mL) was treated with a solution of fumaric acid (80.0 mg, 0.689 mmol) in MeOH (2.5 mL). The mixture was stirred at room temperature overnight. Ether was added to the reaction mixture. The suspension was sonicated, centrifuged, and decanted to afford a solid pellet that was recrystallization from MeOH-ether. The suspension was sonicated, centrifuged, and decanted three times to afford 119 mg (53%) of 4m.0.5 fumarate as a white solid: mp 187-189° C.; $[\alpha]^{22}_D$ +29.6° (c 0.5, MeOH); $^1$H NMR (methanol-$d_4$) δ 7.52-7.41 (m, 2H), 7.38-7.22 (m, 1H), 6.65 (s, 1H), 4.34 (s, 1H), 4.15 (d, 1H, J=12.2 Hz), 3.54 (d, 1H, J=12.2 Hz), 3.46 (q, 1H, J=6.6 Hz), 1.57 (s, 3H), 1.33 (s, 3H), 1.06 (d, 3H, J=6.6 Hz); $^{13}$C NMR (methanol-$d_4$) δ 136.7, 124.4, 118.1, 117.8, 117.1, 116.9, 98.2, 67.5, 54.58, 54.36, 24.1, 21.2, 14.1; LCMS (ESI) m/z 258.6, [(M-fumaric)$^+$ M=$C_{13}H_{17}F_2NO_2$. 0.5$C_4H_4O_4$]; Anal. ($C_{15}H_{19}F_2NO_4$.0.5$H_2O$) calcd: C, 55.55; H, 6.22; N, 4.32. found: C, 55.72; H, 6.07; N, 4.25.

Synthesis of 2-(3,4-Dichlorophenyl)-3,5,5-trimethylmorpholin-2-ol [(±)-4n]

To a solution of 3',4'-dichloropropiophenone (81, 5.02 g, 0.247 mol) in $CH_2Cl_2$ (100 mL) was added ten drops of bromine. After stirring at room temperature under nitrogen for several min, the characteristic red color of bromine disappeared indicating initiation of the reaction. The remainder of the bromine (1.27 mL, 24.7 mmol) was added dropwise and the reaction solution was allowed to stir at room temperature under nitrogen atmosphere for 1.75 h. Analysis by TLC (silica, 2:1 hexane:$CH_2Cl_2$) indicated consumption of starting material. The reaction solution was quenched and brought to a pH of 9 with a saturated aqueous solution of $NaHCO_3$ and concentrated $NH_4OH$. The solution was extracted with $CH_2Cl_2$, dried ($Na_2SO_4$), filtered, concentrated, and dried to give 7.14 g (100%) of 2-bromo-(3',4'-dichlorophenyl)propan-1-one as a white solid. Characterization data is similar with data reported in Anderson, W. K.; Jones, A. N., *J. Med Chem.* 1984, 27, (12), 1559-1565.

2-Bromo-(3',4'-dichlorophenyl)propan-1-one (6.97 g, 0.025 mol) in a minimal amount of $CH_2Cl_2$ was transferred to a sealable reaction tube. Most of the $CH_2Cl_2$ was removed via positive nitrogen flow. 2-Amino-2-methyl-1-propanol (23.6 mL, 247 mmol) was added in one portion, and the tube was sealed and placed in an oil bath heated to 75° C. After stirring at 75° C. overnight, analysis by TLC (silica, 9:1:20 ether-$Et_3N$-hexane) showed only a trace amount of starting material remaining and the reaction was allowed to cool to room temperature. The reaction mixture was quenched and brought to a pH of 10 with a saturated aqueous solution of $NaHCO_3$ and the product was extracted with $CH_2Cl_2$. The organic layer was separated, dried ($Na_2SO_4$), filtered, concentrated, and dried to give 11.29 g of a yellow oil. The residue was purified by column chromatography on silica gel using ether-$Et_3N$-hexane (9:1:50) as eluent to give 3.50 g (49%) of 4n as a white solid: $^1$H NMR (250 MHz, DMSO-$d_6$) δ 7.70-7.67 (m, 1H), 7.47-7.39 (m, 2H), 3.81 (d, 1H), 3.40 (d, 1H), 3.22-3.14 (m, 1H), 1.38 (s, 3H), 1.08 (s, 3H), 0.78 (d, 3H).

A solution of (±)-4n (3.34 g, 0.012 mol) in methanol was treated with fumaric acid (1.34 g, 0.012 mol). The mixture was allowed to stir for 15 min and a white solid precipitated out of solution, which was collected by vacuum filtration to afford 2.23 g (53%) of 4n.0.5 fumarate as a white solid: mp 188-189° C.; $^1$H NMR (250 MHz, DMSO-$d_6$) δ 7.68-7.62 (m, 2H), 7.52-7.48 (m, 1H), 3.77 (d, 1H), 3.36 (d, 1H), 3.13-3.07 (q, 1H), 1.33 (s, 3H), 1.07 (s, 3H), 0.76 (d, 3H); Anal. ($C_{15}H_{19}Cl_2NO_4$) calcd: C, 51.74; H, 5.50; N, 4.02. found: C, 51.48; H, 5.55; N, 3.95.

Synthesis of (2S,3S)-2-(3,5-Difluorophenyl)-3,5,5-trimethylmorpholin-2-ol (4o)

A solution of 15 (448 mg, 3.13 mmol) in anhydrous THF (3 mL, 1M) was cooled to −78° C. and treated with 3,5-dipfluorophenylmagnesium bromide (1.2 equiv., 3.75 mmol, 7.5 mL, 0.5 M solution in THF). The reaction mixture was stirred at −78° C. and under an $N_2$ atmosphere for 1.5 h. Saturated aqueous solution of $NH_4Cl$ was added to the reaction vessel, and the mixture was allowed to warm to room temperature. The reaction mixture was extracted with ether (three times). The combined ether extracts were washed (water, brine), dried ($Na_2SO_4$) and concentrated. Purification of the residue by column chromatography on silica gel using $CH_2Cl_2$ to $CH_2Cl_2$-MeOH—$NH_4OH$ (90:9:1) as the eluent gave 105 mg (13%) of 4o as a yellow solid: $[\alpha]^{22}_D$ +19.5° (c 0.8, CHCl$_3$); $^1$H NMR (CDCl$_3$) δ 7.16-7.10 (m, 2H), 6.82-6.67 (m, 1H), 3.81 (d, 1H, J=12.0 Hz), 3.40 (d, 1H, J=12.0 Hz), 3.18 (q, 1H, J=6.0 Hz), 1.39 (s, 3H), 1.12 (s, 3H), 0.83 (d, 3H, J=6.5 Hz); $^{13}$C NMR (CDCl$_3$) δ 109.63, 109.40, 103.9, 103.5, 103.2, 95.8, 69.2, 53.3, 50.1, 49.6, 26.9, 22.5, 15.2; LCMS (ESI) m/z 258.8 [(M+H)$^+$, M=$C_{13}H_{17}F_2NO_2$].

A sample of 4o (71.0 mg, 0.275 mmol) in $CH_2Cl_2$ (1.5 mL) was treated with HCl (0.386 mmol, 0.100 mL solution 4M in dioxane). The mixture was stirred at room temperature overnight and ether was added to the reaction mixture. The suspension was sonicated, centrifuged, and decanted to afford a solid pellet; this procedure was repeated three times. The solid material was recrystallized from methanol-ether. The suspension was sonicated, centrifuged, decanted and dried to give 60 mg (74%) of 4o.HCl as a pale yellow solid: mp 199-204° C.; $[\alpha]^{22}_D$ +21.5° (c 1.0, MeOH); $^1$H NMR (methanol-$d_4$) δ 7.23-7.18 (m, 2H), 7.03-6.92 (m, 1H), 4.19 (d, 1H, J=12.0 Hz), 3.65-3.54 (m, 2H), 1.62 (s, 3H), 1.39 (s, 3H), 1.12 (d, 3H, J=6.0 Hz); $^{13}$C NMR (methanol-$d_4$) δ 166.1, 162.8, 111.1, 110.9, 105.6, 105.2, 104.9, 66.9, 55.6, 54.5, 23.5, 20.9, 13.7; LCMS (ESI) m/z 258.5 [(M−HCl)$^+$, M=$C_{13}H_{17}F_2NO_2$.HCl]; Anal. ($C_{13}H_{18}ClF_2NO_2$) calcd: C, 53.16; H, 6.18; N, 4.77. found: C, 53.09; H, 6.18; N, 4.71.

Synthesis of 2-(3,5-Dichlorophenyl)-3,5,5-trimethylmorpholin-2-ol [(±)-4p]

To a stirred solution of 3,5-dichloropropiophenone (8m, 3.81 g, 0.0188 mol) in $CH_2Cl_2$ (28 mL) was added bromine (0.986 mL, 19.1 mmol) dropwise. The bromine was immediately consumed upon addition of each drop until the end of addition when it had a consistent brownish color, indicative of excess bromine. The reaction was immediately quenched with saturated aqueous $NaHCO_3$, extracted three times with $CH_2Cl_2$. The organic layer was separated, combined and concentrated under reduced pressure, without drying to afford a yellow oil. The oil was dissolved in anhydrous diethyl ether (50 mL) and 2-amino-2-methyl-1-propanol (6.7 g, 0.075 mol) was added. The reaction mixture was stirred overnight and quenched with saturated aqueous $NaHCO_3$. The aqueous layer was extracted three times with $CH_2Cl_2$, and the organic layers concentrated to afford another yellow oil. Purification by column chromatography on silica gel afforded 2.51 g (46%) of the title compound. The hemi-fumarate salt was prepared by dissolving the free base in methanol and adding 1.0 g of fumaric acid to form the title compound: mp 188-190° C.; $^1$H NMR (DMSO-$d_6$) δ 7.58-7.57 (m, 1H), 7.47 (m, 2H), 6.67 (s, 0.5H), 4.09 (d, 1H, J=11.9 Hz), 3.53 (d, 1H, J=12.0 Hz), 3.41-3.37 (m, 1H), 1.53 (s, 3H), 1.28 (s, 3H), 1.02 (d, 3H, 6.6 Hz); $^{13}$C NMR (DMSO-$d_6$) δ 134.9, 133.6, 127.7, 125.2, 94.7, 67.2, 52.5, 50.1, 25.0, 21.6, 14.6; Anal. ($C_{15}H_{19}Cl_2NO_4$.0.25$H_2O$) calcd: C, 51.08; H, 5.57; N, 3.97. found: C, 51.13; H, 5.64; N, 3.90.

Synthesis of (2S,3S)-2-(Naphthalen-1-yl)-3,5,5-trimethylmorpholin-2-ol (4q)

Compound 4q was synthesized by a procedure similar to that described for (2S,3S)-4a employing (R)-2-hydroxy-1-(naphthalen-1-yl)propan-1-one (10h, 1.15 g, 0.058 mol), Proton sponge (1.5 g, 0.070 mol), triflic anhydride (1.1 mL, 64 mmol), and 2-amino-2-methyl-1-propanol (1.1 g, 0.012 mol) in $CH_3CN$ (45 mL). After purification, 1.35 g (86%) of the free base 4q was isolated and converted to the D-tartrate salt, which was recrystallized from $H_2O$-MeOH-$Et_2O$ solvent system: mp 115-116° C.; $[\alpha]^{20}_D$ −9.5° (c 0.74, $CH_3OH$); $^1$H NMR (methanol-$d_4$) δ 8.89 (d, 1H, J=8.4 Hz), 7.97-7.89 (m, 3H), 7.54-7.50 (m, 3H), 4.33 (s, 1H), 3.70 (d, 1H, J=12.0 Hz), 3.48 (q, 1H, J=7.0 Hx), 1.77 (s, 3H), 1.41 (s, 3H), 0.96 (d, 3H, J=6.6 Hz); $^{13}$C NMR (methanol-$d_4$) δ 136.5, 132.3, 131.9, 130.5, 130.2, 128.1, 127.4, 127.0, 126.1, 99.0, 75.1, 68.1, 67.3, 53.9, 24.8, 22.9, 15.8, 15.2; LCMS (ESI) m/z 272.3 [(M-tartrate)$^+$, M=$C_{19}H_{24}NO_5$]; Anal. ($C_{19}H_{24}NO_5$.0.75$H_2O$) calcd: C, 63.41; H, 7.14; N, 3.89. found: C, 63.63; H, 7.44; N, 3.70.

Synthesis of (2S,3S)-2-(Naphthalen-2-yl)-3,5,5-trimethylmorpholin-2-ol (4r)

Compound 4r was synthesized by a procedure similar to that described for (2S,3S)-4a using (R)-2-hydroxy-1-(naphthalen-2-yl)propan-1-one (10i, 2.5 g, 0.013 mol), Proton sponge (3.24 g, 0.0151 mol), triflic anhydride (2.4 mL, 137 mmol), and 2-amino-2-methyl-1-propanol (2.4 g, 0.027 mol) in acetonitrile (40 mL). After purification, 2.2 g (65%) of the free base 4r was isolated and converted to the hemi-D-tartrate salt: mp 179-180° C.; $[\alpha]^{20}_D$ ×1.5° (c 0.55, $CH_3OH$); $^1$H NMR (methanol-$d_4$) δ 8.13-8.12 (m, 1H), 7.95-7.88 (m, 3H), 7.75-7.71 (m, 1H), 7.57-7.50 (m, 2H), 4.33 (s, 1H), 4.25 (d, 1H, J=11.9 Hz), 3.66-3.57 (m, 2H), 1.65 (s, 3H), 1.37 (s, 3H), 1.09 (d, 3H, J=6.6 Hz); $^{13}$C NMR (methanol-$d_4$) δ 178.7, 139.9, 135.3, 134.6, 129.8, 129.33, 129.00, 128.0, 127.8, 127.4, 125.4, 97.4, 75.2, 67.7, 55.1, 24.5, 21.6, 14.6; LCMS (ESI) m/z 272.5 [(M-tartrate)$^+$, M=$C_{19}H_{24}NO_5$]; Anal. ($C_{19}H_{24}NO_5$.0.5$H_2O$) calcd: C, 65.88; H, 6.98; N, 4.04. found: C, 65.75; H, 7.03; N, 4.06.

Synthesis of (2S,3S)-2-(3-Chlorophenyl)-3-ethyl-5,5-dimethylmorpholin-2-ol (4s)

Compound 4s was synthesized by a procedure similar to that described for (2S,3S)-4a using (R)-1-(3-chlorophenyl)-2-hydroxybutan-1-one (10j, 1.13 g, 0.0568 mol), Proton sponge (1.43 g, 0.0667 mol), triflic anhydride (1.0 g, 0.063 mol), and 2-amino-2-methyl-1-propanol (1.09 g, 0.0122 mol) in $CH_2Cl_2$ (13 mL). After purification, the free base 4r was converted to 0.230 g of its D-tartrate salt: mp 160-161° C.; $[\alpha]^{20}_D$ +5.6° (c 0.8, $CH_3OH$); $^1$H NMR (methanol-$d_4$) δ 7.49-7.46 (m, 1H), 7.41-7.35 (m, 3H), 4.37-4.34 (m, 1H), 4.30-4.24 (m, 1H), 3.81-3.62 (m, 2H), 1.57 (s, 3H), 1.47-1.36 (m, 2H), 1.33 (s, 3H), 0.81-0.71 (m, 3H); $^{13}$C NMR (methanol-$d_4$) δ 178.5, 145.2, 135.6, 131.2, 130.3, 128.2, 126.5, 97.1, 75.0, 67.8, 61.1, 55.0; LCMS (ESI) m/z 270.4 [(M-tartrate)$^+$, M=$C_{16}H_{23}ClNO_5$); Anal. ($C_{16}H_{23}ClNO_5$.0.25$H_2O$) calcd: C, 55.01; H, 6.78; N, 4.01. found: C, 54.99; H, 6.85; N, 4.08.

Synthesis of (2S,3S)-2-(3-Chlorophenyl)-5,5-dimethyl-3-propyl-morpholin-2-ol (4t)

Compound 4t was synthesized by a procedure similar to that described for (2S,3S)-4a using (R)-1-(3-chlorophenyl)-2-hydroxypent-1-one (10k, 1.5 g, 0.0704 mol), Proton sponge (1.8 g, 0.0840 mol), triflic anhydride (1.29 g, 0.081 mol), and 2-amino-2-methyl-1-propanol (1.42 g, 0.0159 mol) in $CH_2Cl_2$ (7 mL). After purification, 790 mg (40%) of the free base 4t was isolated and converted to the hemi-D-tartrate salt, which had 99% ee: mp 151-152° C., $[\alpha]^{20}_D$ −10.1° (c 0.77, $CH_3OH$); $^1$H NMR (methanol-$d_4$) δ 7.50-7.47 (m, 1H), 7.43-7.36 (m, 3H), 4.38 (s, 1H), 4.32 (d, 1H, J=10.0 Hz), 3.81-3.66 (m, 1H), 1.58 (s, 3H), 1.49-1.38 (m, 2H), 1.35 (s, 3H), 1.34-1.27 (m, 1H), 1.02-0.92 (m, 1H), 0.77 (t, 3H, J=7.0 Hz); $^{13}$C NMR (methanol-$d_4$) δ 176.1, 142.9, 133.3, 128.9, 128.0, 125.9, 124.2, 94.8, 72.7, 65.4, 57.0, 52.7, 29.9, 22.0, 19.3, 18.2, 12.1; Anal. ($C_{17}H_{25}ClNO_5$) calcd: C, 56.90; H, 7.02; N, 3.90. found: C, 56.46; H, 7.01; N, 3.79.

Synthesis of (2S,3S)-2-(3-Chlorophenyl)-3,4,5,5-tetramethylmorpholin-2-ol (4u)

A sample of (2S,3S)-2-(3-Chlorophenyl)-3,5,5-trimethylmorpholin-2-ol (4i, 107 mg, 0.42 mmol) in DMF (2.0 mL) was treated with $K_2CO_3$ (174 mg, 1.26 mmol). After stirring the reaction mixture at room temperature under an inert atmosphere for 1.5 h, $CH_3I$ (19.0 µL, 0.3 mmol) was added to the reaction flask and the reaction mixture was stirred at 70° C. for 24 h. The reaction mixture was cooled to 0° C. water added, followed by extraction with ether (three times). The combined organic extracts were washed (water, brine), dried ($Na_2SO_4$) and concentrated to a pale yellow oil. Purification of the residue by column chromatography gave a 72 mg (63%) of 4u as a white solid. The compound 4u was converted to the corresponding di-p-tolyl-L-tartrate salt: mp 128-129° C.; $[\alpha]^{20}_D$ −50.0° (c 0.83, $CH_3OH$); $^1H$ NMR (DMSO-$d_6$) δ 7.85 (d, 4H, J=7.8 Hz), 7.50-7.40 (m, 4H), 7.32 (d, 4H, J=7.8 Hz), 5.6 (s, 2H), 4.07 (d, 1H, J=12.4 Hz), 3.50-3.40 (m, 1H), 2.56 (s, 3H), 2.36 (s, 6H), 1.40 (s, 3H), 1.21 (s, 3H), 0.90 (d, 3H, J=6.2 Hz); $^{13}C$ NMR (DMSO-$d_6$) δ 168.2, 164.9, 143.9, 132.7, 129.9, 129.3 (d), 128.6, 126.67, 126.31, 125.3, 96.4, 72.2, 66.2, 60.4, 59.2, 33.3, 21.1, 15.9, 11.5; Anal. ($C_{34}H_{38}ClNO_{10}·2H_2O$) calcd: C, 59.00; H, 6.12; N, 2.02. found: C, 58.89; H, 6.01; N, 2.00.

Synthesis of (2S,3S)-2-(4-Chlorophenyl)-3,4,5,5-tetramethylmorpholin-2-ol (4v)

A sample of (4i) (144 mg, 0.563 mmol) in anhydrous THF (1.9 mL) was treated with $K_2CO_3$ (4 folds, 311 mg, 2.25 mmol). After stirring the reaction mixture at room temperature under inert atmosphere for 1 h, $CH_3I$ (1.3 equiv., 46.0 µL, 0.731 mmol) was added to the reaction flask. The reaction mixture was stirred at room temperature for 24 h, cooled to 0° C. and water added, followed by extraction with ether (three times). The combined organic extracts were washed (water, brine), dried ($Na_2SO_4$) and concentrated to a pale yellow oil. Purification of the residue by column chromatography on silica gel and $CH_2Cl_2$-MeOH—$NH_4OH$ (90:9:1) as the eluent gave 93.0 mg (61%) of a white solid: mp=75-78° C.; $[\alpha]^{22}_D$ +28.0° (c 1.0, $CHCl_3$); $^1H$ NMR δ 7.58-7.53 (m, 2H), 7.34-7.31 (m, 2H), 4.52-4.49 (br, 1H), 3.90 (d, 1H, J=11.6 Hz), 3.32 (d, 1H, J=11.6 Hz), 2.85 (q, 1H, J=6.5 Hz), 2.20 (s, 3H), 1.19 (s, 3H), 1.07 (s, 3H), 0.76 (d, 3H, J=6.5 Hz); $^{13}C$ NMR δ 133.9, 128.59, 128.36, 128.05, 127.7, 97.5, 70.4, 59.3, 53.8, 32.3, 25.5, 14.4, 13.1; MS (ESI) m/z 270.4 [(M+H)$^+$ M=$C_{14}H_{20}ClNO_2$].

A sample of 4v (90 mg, 0.33 mmol) in ether (1.5 mL) was treated with a solution of fumaric acid (38 mg, 0.33 mmol) in MeOH (1 mL). The mixture was stirred at room temperature overnight. Ether was added to the reaction mixture. The suspension was sonicated, centrifuged, and decanted to afford a solid pellet; this procedure was repeated three times. Recrystallization from MeOH/ether afforded the title product as white solid 101 mg (77%): mp=167-169° C.; $[\alpha]^{22}_D$ +44.3° (c 1.0, MeOH); $^1H$ NMR (methanol-$d_4$) δ 7.60 (d, 2H, J=8.6 Hz), 7.43 (d, 2H, J=8.6 Hz), 6.68 (s, 2H), 4.35 (d, 1H, J=12.8 Hz), 3.64-3.54 (m, 2H), 2.79 (s, 3H), 1.60 (s, 3H), 1.41 (s, 3H), 1.14 (d, 3H, J=6.5 Hz); $^{13}C$ NMR (methanol-$d_4$) δ 171.4, 140.9, 136.3, 129.4, 98.1, 67.6, 63.4, 62.5, 34.4, 21.6, 20.8, 16.9, 12.3; MS (ESI) m/z 270.4 [(M-fumaric)$^+$, M=$C_{14}H_{20}ClNO_2·C_4H_4O_4$]; Anal. ($C_{18}H_{24}ClNO_6·0.5H_2O$) calcd: C, 54.75; H, 6.38; N, 3.55. found: C, 54.53; H, 6.27; N, 3.58.

Synthesis of 3,5,5-Trimethyl-2-(pyridin-3-yl)morpholin-2-ol (5)

A sample of 1-(pyridin-3-yl)propan-1-one (8o, 685 mg, 5.00 mmol) was dissolved in $CCl_4$ (20 mL). Bromine (0.26 mL, 5 mmol) was added to the reaction flask, and the reaction mixture was gently refluxed for 1 h. The solvent was decanted. The deep red solid at the bottom of flask was washed with ether, dried, suspended in $CH_3CN$ (40 mL), and treated with 2-amino-2-methyl-1-propanol (0.89 g, 0.01 mol). The reaction mixture was stirred for 8 h. The precipitate was removed by filtration and the filtrate was extracted with EtOAc. The organic layer was washed with aqueous $NaHCO_3$, dried ($Na_2SO_4$) and concentrated to a deep red oil residue. The oily residue was purified by column chromatography on silica gel and $CH_2Cl_2$-MeOH (20:1 to 5:1) with 1% $NH_4OH$ to give 56 mg free base that was converted to 5.tartrate as a yellow solid: mp 115-116° C.; $^1H$ NMR ($CDCl_3$) δ 8.85-8.83 (m, 1H), 8.54 (dd, 1H, J=4.7, 1.7 Hz), 7.91 (tt, 1H, J=8.0, 2.0 Hz), 7.31-7.25 (m, 1H), 3.85-3.82 (m, 1H), 3.42 (d, 1H, J=11.2 Hz), 3.21 (q, 1H, J=6.5 Hz), 1.40 (s, 3H), 1.10 (s, 3H), 0.81 (d, 3H, J=6.5 Hz); $^{13}C$ NMR ($CDCl_3$) δ 149.4, 148.1, 137.2, 134.1, 122.8, 95.4, 69.4, 53.55, 49.8, 27.4, 22.8, 16.4; LCMS (ESI) m/z 223.3 [(M-tartrate)$^+$, M=$C_{16}H_{24}N_2O_8$]; Anal. ($C_{16}H_{24}N_2O_8·0.75H_2O$) calcd: C, 48.90; H, 6.66; N, 7.26. found: C, 49.92; H, 6.51; N, 6.87.

Synthesis of 3,5,5-Trimethyl-2-(pyridin-2-yl)morpholin-2-ol (6)

1-(Pyridin-2-yl)propan-1-one (8n, 1.71 g, 0.013 mol) was dissolved in $CCl_4$ (50 mL). Bromine (0.66 mL, 12.7 mmol) was added and gently refluxed for 1 h. The solvent was decanted. The orange solid at the bottom of flask was washed with ether, vacuum dried, and then suspend in $CH_3CN$ (40 mL), followed by the addition of 2-amino-2-methyl-1-propanol (2.30 g, 0.0254 mol). The reaction mixture was stirred for 24 h. The precipitate was separated by filtration and was extracted with EtOAc. The organic layer was washed with aqueous $NaHCO_3$ and dried ($Na_2SO_4$) and concentrated to give a orange oil. The residue was purified by column chromatography on silica gel using, $CH_2Cl_2$-MeOH (50:1 to 20:1) with 1% $NH_4OH$ to give 0.94 g (33%) of free base that was converted to the corresponding tartrate salt: $^1H$ NMR ($CDCl_3$) δ 8.55-8.51 (m, 1H), 7.84-7.59 (m, 1H), 7.63-7.57 (m, 1H), 7.34-7.26 (m, 1H), 6.00 (s, 1H), 3.97-3.91 (m, 1H), 3.47-3.37 (m, 2H), 1.42 (s, 3H), 1.10 (s, 3H), 0.74 (d, 3H, J=6.5 Hz); $^{13}C$ NMR ($CDCl_3$) δ 158.6, 147.2, 137.5, 123.6, 120.5, 94.2, 70.0, 52.1, 48.9, 27.1, 22.9, 16.2; LCMS (ESI) m/z 223.4 [(M-tartrate)$^+$, M=$C_{16}H_{24}N_2O_8$]; Anal. ($C_{16}H_{24}N_2O_8·0.5H_2O$) calcd: C, 50.39; H, 6.61; N, 7.35. found: C, 50.44; H, 6.80; N, 7.09.

Synthesis of 1-Naphthalen-1-ylpropan-1-one (8 q)

A sample of 1-cyanonaphthylene (7a, 5.0 g, 0.0327 mol) in dry diethyl ether (200 mL) was treated with ethyl magnesium bromide (49.2 mol, 16.4 mL 3 M solution in ether) under nitrogen atmosphere at room temperature. The solution was stirred overnight at 25° C. and then cooled to 0° C. The reaction was quenched slowly with 1 N aqueous HCl and allowed to warm to room temperature over 1 h with stirring. The aqueous layer was extracted with ether. The combined organic layers were washed with aqueous NaHCO$_3$, water and brine, and dried (Na$_2$SO$_4$). The organic layers were concentrated and the resulting yellow oil was purified by column chromatography on silica gel using hexane-EtOAc (20:1) to (10:1) as the eluent afforded 3.55 g (60%) of the title product: $^1$H NMR (CDCl$_3$) δ 8.59-8.52 (m, 1H), 8.00-7.94 (m, 1H), 7.90-7.81 (m, 2H), 7.62-7.45 (m, 3H), 3.08 (q, 2H, J=7.3 Hz), 1.29 (t, 3H, J=7.3 Hz). C$_{13}$H$_{12}$O.

Synthesis of 1-Naphthalen-2-ylpropan-1-one (8r)

Compound 8r was synthesized by a procedure similar to that described for 8q using identical amounts, except commercially available 2-cyanonaphthylene (7b) was used in place of 1-cyanonaphthylene. Purification by column chromatography on silica gel using hexane-EtOAc (20:1) to (10:1) afforded 4 g (66%) of the title product as a white solid: $^1$H NMR (CDCl$_3$) δ 8.48 (s, 1H), 8.05 (d, 1H, J=7.5 Hz), 8.00-7.94 (m, 1H), 7.93-7.85 (m, 2H), 7.64-7.51 (m, 2H). 3.15 (q, 2H, J=7.2 Hz), 1.29 (t, 3H, J=7.2 Hz); $^{13}$C NMR (CDCl$_3$) δ 129.9, 128.8 (d), 128.2, 127.1, 124.3, 32.3, 8.8. C$_{13}$H$_{12}$O.

Synthesis of (Z)-tert-Butyl(1-phenylprop-1-enyloxy)dimethylsilane (9b)

Compound 9b was synthesized by a procedure similar to 9a using commercially available propiophenone (8b, 5.0 g, 0.037 mol), TBDMSOTf (9.4 mL, 41.0 mmol), and of Et$_3$N (8.3 mL) in CH$_2$Cl$_2$ (50 mL). After purification, 7.32 g (79%) of 9b was isolated as colorless oil: $^1$H NMR (CDCl$_3$) δ 7.50-7.40 (m, 2H), 7.35-7.22 (m, 3H), 5.23 (q, 1H, J=6.9 Hz), 1.77 (d, 3H, J=6.9 Hz), 1.03 (s, 9H), −0.04 (s, 6H); $^{13}$C NMR (CDCl$_3$) δ 150.4, 140.0, 128.0, 127.4, 125.9, 105.9, 25.9, 18.5, 11.9, −3.9; C$_{15}$H$_{24}$OSi.

Synthesis of (Z)-tert-Butyl(1-(3-fluorophenyl)prop-1-enyloxy)dimethylsilane (9c)

Compound 9c was synthesized by a procedure similar to that described for 9a using commercially available 3-fluoropropiophenone (8c, 5.0 g, 0.033 mol), TBDMSOTf (8.3 mL, 36.1 mmol), and Et$_3$N (7.3 mL) in CH$_2$Cl$_2$ (50 mL). After purification, 8.1 g (93%) of 9c was isolated as colorless oil: $^1$H NMR (CDCl$_3$) δ 7.38-7.10 (m, 2H), 7.00-6.87 (m, 1H), 5.26 (q, 1H, J=6.9 Hz), 1.75 (d, 3H, J=6.9 Hz), 1.00 (s, 9H), −0.02 (s, 6H); $^{13}$C NMR (CDCl$_3$) δ 164.5, 161.2, 149.2, 142.4, 129.4, 121.4, 114.3, 114.0, 112.8, 112.5, 107.1, 105.9, 26.0, 18.5, 11.9, ×3.9. C$_{15}$H$_{23}$FOSi.

Synthesis of (Z)-tert-Butyl(1-(3-bromophenyl)prop-1-enyloxy)dimethylsilane (9d)

Compound 9d was synthesized by a procedure similar to that described for 9a using commercially available 3-bromopropiophenone (8d, 1.0 g, 0.0047 mol), TBDMSOTf (1.4 mL, 5.1 mmol), and Et$_3$N (1.1 mL) in CH$_2$Cl$_2$ (10 mL). After workup, 1.15 g (75%) of crude 9d was isolated as colorless oil with a Z-E ratio of 94:6: $^1$H NMR (CDCl$_3$) δ 7.64-7.58 (m, 1H), 7.41-7.34 (m, 2H), 7.17 (t, 1H, J=8.04 Hz), 5.25 (q, 1H, J=6.9 Hz), 1.75 (d, 3H, J=6.9 Hz), 1.02 (s, 9H), −0.03 (s, 6H); $^{13}$C NMR (CDCl$_3$) δ 148.8, 141.9, 130.2, 129.5, 128.7, 124.1, 122.1, 25.8, 18.3, 11.8, −4.0. C$_{15}$H$_{23}$BrOSi.

Synthesis of (Z)-tert-Butyl(1-(m-tolyl)prop-1-enyloxy)dimethylsilane (9e)

Compound 9e was synthesized by a procedure similar to that described for 9a using commercially available 3-methylpropiophenone (8e, 5.0 g, 0.033 mol), TBDMSOTf (8.5 mL, 36.1 mmol), and Et$_3$N (7.5 mL) in CH$_2$Cl$_2$ (50 mL). After purification by column chromatography on silica gel, 7.45 g (84%) of 9e was isolated as colorless oil: $^1$H NMR (CDCl$_3$) δ 7.31-7.24 (m, 2H), 7.23-7.17 (m, 1H), 7.10-7.05 (m, 1H), 5.22 (q, 1H, J=6.9 Hz), 2.37 (s, 3H), 1.76 (d, 3H, J=6, 9 Hz), 1.03 (s, 9H), −0.03 (s, 6H); $^{13}$C NMR (CDCl$_3$) δ 150.7, 140.1, 137.7, 128.4, 127.9, 126.8, 123.2, 105.9, 26.3, 21.8, 18.7, 12.1, −3.6. C$_{16}$H$_{26}$OSi.

Synthesis of (Z)-tert-Butyl-(1-(3-methoxyphenyl)prop-1-enyloxy)dimethylsilane (9f)

Compound 9f was synthesized by a procedure similar to that described for 9a using 3-methoxypropiophenone (8f, 6.00 g, 0.0366 mol), TBDMSOTf (9.2 mL, 40.2 mmol), and Et$_3$N (8.1 mL) in CH$_2$Cl$_2$ (60 mL). After purification on alumina, 8.14 g (80%) of 9f was isolated as colorless oil: $^1$H NMR (CDCl$_3$) δ 7.24-7.16 (m, 1H), 7.07-6.98 (m, 2H), 6.84-6.76 (m, 1H), 5.23 (q, 1H, J=6.9 Hz), 3.81 (s, 3H), 1.75 (d, 3H, J=6.9 Hz), 1.01 (s, 9H), −0.01 (s, 6H); $^{13}$C NMR (CDCl$_3$) δ 159.4, 150.1, 141.5, 129.0, 118.4, 113.3, 111.2, 106.1, 55.3, 26.0, 18.5, 11.9, −3.9. C$_{16}$H$_{26}$O$_2$Si.

Synthesis of (Z)-tert-Butyl-(1-(3-nitrophenyl)prop-1-enyloxy)dimethylsilane (9g)

Compound 9g was synthesized by a procedure similar to that described for 9a using commercially available 3-nitropropiophenone (8g, 5.0 g, 0.028 mol), TBDMSOTf (7.1 mL, 30.7 mmol), and Et$_3$N (6.2 mL) in CH$_2$Cl$_2$ (50 mL). After purification on alumina, 8.0 g (98%) of 9g was isolated as colorless oil: $^1$H NMR (CDCl$_3$) δ 8.34-8.30 (m, 1H), 8.12-8.06 (m, 1H), 7.80-7.75 (m, 1H), 7.52-7.42 (m, 1H), 5.40 (q, 1H, J=6.9 Hz), 1.78 (d, 3H, J=6.9 Hz), 1.02 (s, 9H), −0.02 (s, 6H); $^{13}$C NMR (CDCl$_3$) δ 148.8, 141.6, 131.3, 129.0, 122.1, 120.5, 108.6, 106.8, 25.9, 18.4, 12.0, −3.8. C$_{15}$H$_{23}$NO$_3$Si.

Synthesis of (Z)-tert-Butyldimethyl-(1-(naphthalen-1-yl)prop-1-enyloxy)silane (9q)

Compound 9q was synthesized by a procedure similar to that described for 9a using 1-naphthalen-1-ylpropan-1-one (8h, 3.5 g, 0.019 mol), TBDMSOTf (4.8 mL, 0.021 mol), and Et$_3$N (4.3 mL) in CH$_2$Cl$_2$ (26 mL). After purification, 4.58 g (81%) of title product was isolated as colorless oil: $^1$H NMR (CDCl$_3$) δ 8.27-8.24 (m, 1H), 7.83-7.75 (m, 2H), 7.48-7.38 (m, 4H), 5.04 (q, 1H, J=6.0 Hz), 1.83 (d, 3H, J=6.0 Hz), 0.87 (s, 9H), −0.29 (s, 6H); $^{13}$C NMR (CDCl$_3$) δ 150.0, 138.3, 133.6, 131.6, 128.1, 128.0, 126.8, 126.2, 125.7, 125.1, 108.4, 26.3, 25.7, 18.2, −4.6. C$_{19}$H$_{26}$OSi.

Synthesis of (Z)-tert-Butyldimethyl-(1-(naphthalen-2-yl)prop-1-enyloxy)silane (9r)

Compound 9r was synthesized by a procedure similar to that described for 9a using 1-naphthalen-2-ylpropan-1-one (8i, 4.0 g, 0.0217 mol, TBDMSOTf (5.5 mL, 23.9 mmol), and Et$_3$N (4.9 mL) in CH$_2$Cl$_2$ (26 mL). After purification, 4.7 g (73%) of the title product was isolated as colorless oil: $^1$H NMR (CDCl$_3$) δ 7.86-7.74 (m, 1H), 7.86-7.74 (m, 3H), 7.59 (dd, 1H, J=8.6, 1.7 Hz), 7.51-7.41 (m, 2H), 5.38 (q, 1H, J=6.9 Hz), 1.81 (d, 3H, J=6.9 Hz), 1.04 (s, 9H), 0.02 (s, 6H); $^{13}$C NMR (CDCl$_3$) δ 150.5, 137.5, 133.5, 133.2, 128.5, 127.9, 127.8, 126.4, 126.0, 107.0, 105.9, 26.3, 26.1, 18.8, −3.6. C$_{19}$H$_{26}$OSi.

Synthesis of (Z)-tert-Butyl(1-(3-chlorophenyl)but-1-enyloxy)dimethylsilane (9s)

Compound 9s was synthesized by a procedure similar to that described for 9a using 3-chlorobutyrophenone (8j, 3.1 g, 0.0169 mol), TBDMSOTf (4.3 mL, 18.6 mmol), and Et$_3$N (3.8 mL) in CH$_2$Cl$_2$ (30 mL). After purification, 3.7 g (74%) of the title product was isolated as colorless oil: $^1$H NMR (CDCl$_3$) δ 7.48-7.44 (m, 1H), 7.38-7.32 (m, 1H), 7.31-7.29 (m, 2H), 5.16 (t, 1H, J=7.1 Hz), 2.30-2.19 (m, 2H), 1.09-1.03 (m, 3H), 1.01 (s, 9H), −0.04 (s, 6H); $^{13}$C NMR (CDCl$_3$) δ 147.5, 141.7, 133.9, 129.2, 127.3, 125.9, 123.8, 114.9, 25.8, 19.5, 14.1, 0.0, −4.1. C$_{16}$H$_{25}$ClOSi.

Synthesis of (Z)-tert-Butyl(1-(3-chlorophenyl)pent-1-enyloxy)dimethylsilane (9t)

Compound 9t was synthesized by a procedure similar to that described for 9a using 3-chloropentaphenone (8k, 2.7 g, 0.014 mol), TBDMSOTf (3.5 mL, 15 mmol), and Et$_3$N (3.1 mL) in CH$_2$Cl$_2$ (25 mL). After purification, 4.18 g (96%) of the title product was isolated as colorless oil: $^1$H NMR (CDCl$_3$) δ 7.47-7.44 (m, 1H), 7.38-7.32 (m, 1H), 7.30-7.28 (m, 1H), 7.25-7.22 (m, 1H), 5.18 (t, 1H, J=7.2 Hz), 2.20 (q, 2H, J=7.5 Hz), 1.54-1.38 (m, 2H), 1.02 (s, 9H), 1.00-0.90 (m, 3H), −0.05 (s, 6H); $^{13}$C NMR (CDCl$_3$) δ 148.0, 141.8, 133.9, 129.2, 127.6, 125.9, 123.9, 113.0, 28.3, 25.8, 22.8, 14.0, 0.0, −4.01. C$_{17}$H$_{27}$ClOSi.

Synthesis of (S)-1-(3-Chlorophenyl)-2-hydroxypropan-1-one [(S)-10a]

Compound (S)-10a was synthesized by a procedure similar to that described for (R)-10a using (Z)-tert-butyl(1-(3-chlorophenyl)prop-1-enyloxy)dimethylsilane (9a, 8.8 g, 0.031 mol), AD-mix-α (43.5 g), and CH$_3$SO$_2$NH$_2$ (3a, 3 g, 0.032 mol) in tert-butyl alcohol-water (120 mL:120 mL). The reaction mixture was quenched with sodium sulfite (31.1 g). After purification, 4.51 g (78%) of the (S)-10a was isolated. Characterization data is similar with data reported in Fang, Q. K.; Han, Z.; Grover, P.; Kessler, D.; Senanayake, C. H.; Wald, S. A., *Tetrahedron: Asymmetry* 2000, 11, 3659-3663.

Synthesis of (R)-1-Phenyl-2-hydroxypropan-1-one (10b)

Compound 10b was synthesized by a procedure similar to that described for (R)-10a using (Z)-tert-butyl(1-phenprop-1-enyloxy)dimethylsilane (9b, 7.2 g, 0.029 mol), AD-mix-β (40.7 g), and CH$_3$SO$_2$NH$_2$ (2.8 g, 0.0294 mol) in tert-butyl alcohol-water (110 mL:110 mL). The reaction was quenched with sodium sulfite (29.1 g). After purification, 2.49 g (80%) of the title product was isolated: [α]$^{20}_D$ +84.9° (c 1.6, CHCl$_3$); $^1$H NMR (CDCl$_3$) δ 7.96-7.90 (m, 2H), 7.66-7.58 (m, 1H), 7.54-7.47 (m, 2H), 5.23-5.12 (m, 1H), 3.84 (d, 1H, J=6.3 Hz), 1.45 (d, 3H, J=7.05 Hz); $^{13}$C NMR (CDCl$_3$) δ 202.4, 134.0, 133.4, 128.9, 128.7, 69.3, 22.3. C$_9$H$_{10}$O$_2$.

Synthesis of (R)-1-(3-Fluorophenyl)-2-hydroxypropan-1-one (10c)

Compound 10c was synthesized by a procedure similar to that described for (R)-10a using (Z)-tert-butyl(1-(3-fluorophenyl)prop-1-enyloxy)dimethylsilane, (9c, 8.0 g, 0.030 mol), AD-mix-3 (42.1 g), and CH$_3$SO$_2$NH$_2$ (2.90 g, 0.0301 mol) in tert-butyl alcohol-water (120 mL:120 mL). The reaction was quenched with sodium sulfite (30.1 g). After purification, 4.4 g (87%) of the desired product 10c was isolated: [α]$^{20}_D$ +58.1° (c 3.2, CHCl$_3$); $^1$H NMR (CDCl$_3$) δ 7.74-7.59 (m, 2H), 7.54-7.45 (m, 1H), 7.37-7.28 (m, 1H), 5.19-5.07 (m, 1H), 1.76 (d, 1H, J=6.3 Hz), 1.46 (d, 3H, J=6.9 Hz); $^{13}$C NMR (CDCl$_3$) δ 201.6, 164.9, 131.0, (d), 124.7, 121.3 (d), 115.8 (d), 69.9, 22.4. C$_9$H$_9$FO$_2$.

Synthesis of (R)-1-(3-Bromophenyl)-2-hydroxypropan-1-one (10d)

Compound 10d was synthesized by a procedure similar to that described for (R)-10a using (Z)-tert-butyl(1-(3-bromophenyl)prop-1-enyloxy)dimethylsilane, (9d, 1.15 g, 0.0035 mol), AD-mix-β (4.9 g), and CH$_3$SO$_2$NH$_2$ (334 mg, 3.5 mmol) in tert-butyl alcohol-water (17.5 mL:17.5 mL). The reaction was quenched with sodium sulfite (3.5 g). After purification by column chromatography on silica gel, 0.700 g (88%) of the desired product was isolated: [α]$^{20}_D$ +61.1° (c 1.3, CHCl$_3$); $^1$H NMR (CDCl$_3$) δ 8.09-8.04 (m, 1H), 7.87-7.81 (m, 1H), 7.78-7.72 (m, 1H), 7.39 (t, 1H, J=8.0 Hz), 5.18-5.05 (m, 1H), 3.66 (d, 1H, J=6.4 Hz), 1.45 (d, 3H, J=7.2 Hz); $^{13}$C NMR (CDCl$_3$) δ 201.2, 136.8, 135.2, 131.6, 130.4, 127.1, 123.3, 69.5, 22.1. C$_9$H$_9$BrO$_2$.

Synthesis of (R)-1-(m-Tolyl)-2-hydroxypropan-1-one (10e)

Compound 10e was synthesized by a procedure similar to that described for (R)-10a using (Z)-tert-butyl(1-(3-methylphenyl)prop-1-enyloxy)dimethylsilane, (9e, 7.4 g, 0.028 mol), AD-mix-β (39.5 g), and CH$_3$SO$_2$NH$_2$ (2.73 g, 0.029 mol) in tert-butyl alcohol-water (110 mL:110 mL). The reaction was quenched with sodium sulfite (28.3 g). After purification, 4.2 g (85%) of the desired 10e was isolated: [α]$^{20}_D$ +83.9° (c 2.0, CHCl$_3$); $^1$H NMR (CDCl$_3$) δ 7.78-7.67 (m, 2H), 7.46-7.33 (m, 2H), 5.20-5.09 (m, 1H), 3.86 (d, 1H, J=6.3 Hz), 2.42 (s, 3H), 1.44 (d, 3H, J=7.0 Hz); $^{13}$C NMR (CDCl$_3$) δ 202.6, 138.8, 134.8, 133.5, 129.1, 128.7, 125.9, 69.4, 22.3, 21.4. C$_{10}$H$_{12}$O$_2$.

Synthesis of (R)-1-(3-Methoxyphenyl)-2-hydroxypropan-1-one (10f)

Compound 10f was synthesized by a procedure similar to that described for (R)-10a using (Z)-tert-butyl(1-(3-methoxyphenyl)prop-1-enyloxy)dimethylsilane, (9f, 8.1 g, 0.029 mol), AD-mix-β (40.7 g), and CH$_3$SO$_2$NH$_2$ (2.8 g, 0.0294 mol) in tert-butyl alcohol-water (110 mL:110 mL). The reaction was quenched with sodium sulfite (29.1 g). After purification, 4.2 g (80%) of the desired 10f was isolated: [α]$^{20}_D$ +71.1° (c 1.1, CHCl$_3$); $^1$H NMR (CDCl$_3$) δ 7.51-7.45 (m, 2H), 7.44-7.37 (m, 1H), 7.19-7.13 (m, 1H), 5.19-5.09 (m, 1H), 3.87 (s, 3H), 3.76 (d, 1H, J=6.5 Hz), 1.45 (d, 3H, J=7.1 Hz); $^{13}$C NMR (CDCl$_3$) δ 202.3, 160.0, 134.7, 129.9, 121.1, 120.3, 113.1, 69.4, 55.5, 22.4. C$_{10}$H$_{12}$O$_3$.

Synthesis of (R)-1-(3-Nitrophenyl)-2-hydroxypropan-1-one (10g)

Compound 10g was synthesized by a procedure similar to that described for (R)-10a using (Z)-tert-butyl(1-(3-nitrophenyl)prop-1-enyloxy)dimethylsilane, (9g, 8.0 g, 0.027 mol), AD-mix-β (38 g), and CH$_3$SO$_2$NH$_2$ (2.64 g, 0.0277 mol) in tert-butyl alcohol-water (110 mL:110 mL). The reaction was quenched with sodium sulfite (27.4 g). After purification by column chromatography on silica gel, 4.0 g (75%) of the desired product was isolated: $[\alpha]^{20}_D$ +63.8° (c 1.3, CHCl$_3$); $^1$H NMR (CDCl$_3$) δ 8.80-8.74 (m, 1H), 8.52-8.44 (m, 1H), 8.31-8.24 (m, 1H), 7.83-7.68 (m, 1H), 5.27-5.13 (m, 1H), 3.59 (d, 1H, J=6.5 Hz), 1.49 (d, 3H, J=7.08 Hz); $^{13}$C NMR (CDCl$_3$) δ 200.4, 148.6, 134.9, 134.1, 130.2, 128.1, 121.6, 69.8, 21.9; C$_9$H$_9$NO$_4$.

Synthesis of (R)-2-Hydroxy-1-(naphthalen-1-yl)propan-1-one (10h)

Compound 10h was synthesized by a procedure similar to that described for (R)-10a using (Z)-tert-butyl(1-(naphthalen-1-yl)prop-1-enyloxy)dimethylsilane, (9h, 4.58 g, 0.015 mol), AD-mix-β (21.4 g), and CH$_3$SO$_2$NH$_2$ (1.5 g, 0.0158 mol) in tert-butyl alcohol-water (60 mL:60 mL). The reaction was quenched with sodium sulfite (15.3 g). After purification by column chromatography on silica gel, 1.15 g (38%) of the title product was isolated plus 2.1 g of starting olefin was recovered, raising the effective yield to 70%: $[\alpha]^{20}_D$ +140.2° (c 3.2, CHCl$_3$); $^1$H NMR (CDCl$_3$) δ 8.51-8.46 (m, 1H), 8.04 (d, 1H, J=8.3 Hz), 7.93-7.87 (m, 1H), 7.80-7.75 (m, 1H), 7.66-7.48 (m, 3H), 5.30-5.17 (m, 1H), 3.96 (d, 1H, J=5.8 Hz), 1.36 (d, 3H, J=7.1 Hz); $^{13}$C NMR (CDCl$_3$) δ 205.7, 134.1, 133.5, 132.5, 130.7, 128.7, 128.4, 127.7, 126.9, 125.5, 124.4, 71.2, 21.3; LCMS (ESI) m/z 201.2 [(M+H)$^+$, M=C$_{13}$H$_{12}$O$_2$].

Synthesis of (R)-2-Hydroxy-1-(naphthalen-2-yl)propan-1-one (10i)

Compound 10i was synthesized by a procedure similar to that described for (R)-10a using (Z)-tert-butyl(1-(naphthalen-2-yl)prop-1-enyloxy)dimethylsilane, (9i, 4.7 g, 0.016 mol), AD-mix-β (22.0 g), and CH$_3$SO$_2$NH$_2$ (1.55 g, 0.016 mol) in tert-butyl alcohol-water (60 mL:60 mL). The reaction was quenched with sodium sulfite (15.7 g). After purification by column chromatography on silica gel, 2.5 g (80%) of the desired product was isolated: $[\alpha]^{20}_D$ +115° (c 0.7, CHCl$_3$); $^1$H NMR (CDCl$_3$) δ 8.44 (s, 1H), 8.01-7.86-8.00 (m, 4H), 7.69-7.54 (m, 2H), 5.37-5.27 (m, 1H), 3.86 (d, 1H, J=6.5 Hz), 1.52 (d, 3H, J=7.0 Hz); $^{13}$C NMR (CDCl$_3$) δ 202.3, 136.0, 132.4, 130.7, 130.5, 129.7, 129.0, 128.8, 127.9, 127.1, 124.0, 69.4, 22.5; C$_{13}$H$_{12}$O$_2$.

Synthesis of (R)-1-(3-Chlorophenyl)-2-hydroxybutan-1-one (10j)

Compound 10j was synthesized by a procedure similar to that described for (R)-10a using (Z)-tert-butyl(1-(3-chlorophenyl)but-1-enyloxy)dimethylsilane (9j, 3.7 g, 0.013 mol), AD-mix-β (17.5 g), and CH$_3$SO$_2$NH$_2$ (1.2 g, 0.0126 mol) in tert-butyl alcohol-water (45 mL:45 mL). The reaction was quenched with sodium sulfite (12.5 g). After purification by column chromatography on silica gel, 2.2 g (79%) of the title product was isolated: $[\alpha]^{20}_D$ +31.4° (c 1.0, CHCl$_3$); $^1$H NMR (CDCl$_3$) δ 7.91-7.88 (m, 1H), 7.81-7.75 (m, 1H), 7.62-7.56 (m, 1H), 7.45 (t, 1H, J=7.8 Hz), 5.06-4.98 (m, 1H), 3.60 (d, 1H, J=6.5 Hz), 2.04-1.87 (m, 1H), 1.70-1.51 (m, 1H), 0.94 (t, 3H, J=7.4 Hz); $^{13}$C NMR (CDCl$_3$) δ 201.4, 135.8, 135.7, 134.2, 130.6, 128.9, 126.9, 74.5, 29.1, 9.2. C$_{10}$H$_{11}$ClO$_2$.

Synthesis of (R)-1-(3-Chlorophenyl)-2-hydroxypentan-1-one (10k)

Compound 10k was synthesized by a procedure similar to that described for (R)-10a using (Z)-tert-butyl(1-(3-chlorophenyl)pent-1-enyloxy)dimethylsilane (9k, 4.1 g, 0.013 mol), AD-mix-β (18.5 g), and CH$_3$SO$_2$NH$_2$ (1.3 g, 0.014 mol) in tert-butyl alcohol-water (50 mL:50 mL). The reaction was quenched with sodium sulfite (13.2 g). After purification, 2.4 g (77%) of the desired product was isolated: $[\alpha]^{20}_D$ +33.3° (c 1.1, CHCl$_3$); $^1$H NMR (CDCl$_3$) δ 7.91-7.87 (m, 1H), 7.80-7.75 (m, 1H), 7.63-7.17 (m, 1H), 7.45 (t, 1H, J=7.6 Hz), 5.08-5.00 (m, 1H), 3.58 (d, 1H, J=6.5 Hz), 1.89-1.75 (m, 1H), 1.61-1.35 (m, 3H), 0.93 (t, 3H, J=7.2 Hz); $^{13}$C NMR (CDCl$_3$) δ 201.1, 135.4, 133.8, 130.2, 128.6, 126.5, 73.2, 37.8, 18.2, 13.8. C$_{11}$H$_{13}$ClO$_2$.

Synthesis of Methyl (2R)-2-[(trifluoromethyl)sulfonyl]oxypropionate) (14)

Following a procedure reported in Damaj, M. I.; Fei-Yin, M.; Dukat, M.; Glassco, W.; Glennon, R. A.; Martin, B. R., *J. Pharmacol. Exp. Ther.* 1998, 284, 1058-1065 with modification, a solution of methyl-(R)-lactate (13) (5.20 g, 0.05 mol) in anhydrous CH$_2$Cl$_2$ (200 mL, 0.25 M) was cooled to 0° C. and was treated with trifluromethane sulfonic anhydride (8.8 mL, 52.5 mmol) and 2,6-lutidine (6.10 mL, 52.5 mmol) under an N$_2$ atmosphere. After stirring for 20 min at 0° C., the reaction mixture was concentrated to a pink oil residue. Column chromatography on silica gel using CH$_2$Cl$_2$ as the eluent afforded 9.15 g (77%) of 14 as a light pink oil with characterization data as previously reported:[31] $[\alpha]^{25}_D$ +40.5° (c 1.0, CHCl$_3$); $^1$H NMR (CDCl$_3$) δ 5.27 (q, 1H, J=6.9 Hz), 3.85 (s, 3H), 1.71 (d, 3H, J=6.9 Hz); $^{13}$C NMR (CDCl$_3$) δ 167.8, 79.9, 53.3, 18.0; LCMS (ESI) m/z 240.1 [(M+4H)$^+$, M=C$_5$H$_7$F$_3$O$_5$S].

Synthesis of (3S)-3,5,5-Trimethylmorpholin-2-one (15)

A solution of triflate 14 (5.00 g, 0.021 mol) in anhydrous CH$_2$Cl$_2$ (80 mL) under an N$_2$ atmosphere, was cooled to -40° C. and was treated with a solution of 2-amino-2-methyl-1-propanol (2.5 folds, 4.68 g, 0.0525 mol) in anhydrous CH$_2$Cl$_2$ (10 mL). After stirring for 2 h at -40° C., the reaction mixture was warmed slowly to 0° C. then to room temperature and stirred overnight. The reaction mixture was treated with saturated aqueous NaHCO$_3$ solution (100 mL). The organic phase was washed (water, brine), separated, and dried (Na$_2$SO$_4$). The aqueous layer was extracted with EtOAc (twice). The organic layer was separated, washed (water, brine) and dried (Na$_2$SO$_4$). The organic extracts were combined and concentrated to give a yellow oil. Column chromatography on silica gel using hexanes-EtOAc (1:2) to EtOAc gave 1.88 g (63%) of 15 as a light yellow oil: $[\alpha]^{23}_D$ -75° (c 1.0, CHCl$_3$); $^1$H NMR (CDCl$_3$) δ 4.11 (s, 2H), 3.71 (q, 1H, J=6.8), 1.39 (d, 3H, J=6.8 Hz), 1.26 (s, 3H), 1.18 (s, 3H); $^{13}$C NMR (CDCl$_3$) δ 229.2, 77.6, 49.5, 49.3, 27.2, 24.2, 18.4; LCMS (APCI) m/z 144.3 [(M+H)$^+$, M=C$_7$H$_{13}$NO$_2$]; Anal. (C$_7$H13NO$_2$) calcd: C, 58.72; H, 9.15; N, 9.78. found: C, 58.60; H, 9.35; N, 9.79. Note: $^1$H NMR data is similar with the data reported in the literature for the racemic compound (Koch, T. H.; Olesen, J. A.; DeNiro, J., *J. Am. Chem. Soc.* 1975, 97, (25), 7285-7288).

Example 2

Biological Studies a) In Vitro Studies

Cell Lines and Culture:

Human embryonic kidney (HEK-293) cells stably expressing human DAT, NET or SERT were maintained as previously described in Eshleman, A. J.; Carmolli, M.; Cumbay, M.; Martens, C. R.; Neve, K. A.; Janowsky, A., *J. Pharmacol. Exp. Ther.* 1999, 289, (2), 877-885. Use was made of several human cell lines that naturally or heterologously express specific, functional, human nAChR subtypes. Cells of the TE671/RD line naturally expresses muscle-type nAChR ($\alpha1\beta1\gamma\delta$- or $\alpha1^*$-nAChR), and SH-SY5Y neuroblastoma cells naturally expresses autonomic $\alpha3\beta4^*$-nAChRs (containing $\alpha3$, $\beta4$, probably $\alpha5$, and sometimes $\beta2$ subunits). Different clones of SH-EP1 epithelial cell lines have been engineered to heterologously express either $\alpha4\beta2$-nAChR, which are thought to be the most abundant, high affinity nicotine-binding nAChR in mammalian brain, or $\alpha4\beta4$-nAChR, another possible brain nAChR subtype (SH-EP1-h$\alpha4\beta2$ or $\alpha4\beta4$ cells, respectively). These cells were maintained as low passage number (1-26 from our frozen stocks) cultures to ensure stable expression of native or heterologously-expressed nAChR as previously described (see Lukas, R. J.; Fryer, J. D.; Eaton, J. B.; L., G. C., Some methods for studies of nicotinic acetylcholine receptor pharmacology, in *Nicotinic receptors and the Nervous System*, Levine, E. D., Ed. CRC Press: Boca Raton, 2002; pp 3-27, incorporated herein by reference in its entirety). Cells were passaged once weekly by splitting just-confluent cultures 1/300 (TE671/RD), 1/5 (SH-SY5Y), or 1/20 (transfected SH-EP1) in serum-supplemented medium to maintain log-phase growth.

Transporter Assays:

The (2S,3S)-4a analogues 4b-4v and comparison compounds 5 and 6 were evaluated for their ability to inhibit uptake of [$^3$H]dopamine ([$^3$H]DA), [$^3$H]serotonin ([$^3$H]5HT), and [$^3$H]norepinephrine ([$^3$H]NE) into HEK293 cells stably expressing human DA transporters [(h)DAT], 5HT transporters [(h)SERT], or NE transporters [h(NET)] using methods similar to those previously reported. See, for example, Damaj, M. I.; Carroll, F. I.; Eaton, J. B.; Navarro, H. A.; Blough, B. E.; Mirza, S.; Lukas, R. J.; Martin, B. R., *Mol. Pharmacol.* 2004, 66, (3), 675-682 and Eshleman, A. J.; Carmolli, M.; Cumbay, M.; Martens, C. R.; Neve, K. A.; Janowsky, A., *J. Pharmacol. Exp. Ther.* 1999, 289, (2), 877-885, both incorporated by reference herein in their entireties. The results are given in Table 4.

Compound 2 (bupropion) inhibits dopamine reuptake ($IC_{50}$=660 nM), which would increase synaptic levels of dopamine and presumed reward. Compound (2S,3S)-4a ($IC_{50}$=630 nM), but not (2R,3R)-4a ($IC_{50}$>10 μM), is as effective as 2 in inhibiting DA uptake inhibition. Compound 2 also inhibits norepinephrine reuptake ($IC_{50}$=1850 nM), which increases synaptic levels of norepinephrine. Interestingly, (2S,3S)-4a ($IC_{50}$=241 nM), but not (2R,3R)-4a ($IC_{50}$=9900 nM), is 7.7-times more potent than 2 in inhibiting NE uptake. Neither 2 nor its hydroxymetabolites are active ($IC_{50}$>10 μM) as inhibitors of serotonin (5HT) uptake.

Among the new hydroxybupropion analogues tested, the propyl extended chain form 4t and the (±)-3',4'-dichlorophenyl derivative (±)-4n form of (2S,3S)-4a with $IC_{50}$ values of 30 and 70 nM, respectively, the ethyl extended chain form 4s ($IC_{50}$=204 nM), the 4-chlorophenyl analogue 4i ($IC_{50}$=285 nM), and the 2-napthyl derivative 4r ($IC_{50}$=453 nM) have higher potency than (2S,3S)-4a ($IC_{50}$=630 nM) as inhibitors of DA uptake.

In terms of activity for NE uptake inhibition, the ethyl and propyl extended chain forms, 4s and 4t ($IC_{50}$ values of 43 nM and 31 nM, respectively), the (±)-3'-,4'-dichlorophenyl derivative (±)-4n ($IC_{50}$=114 nM) and the 3',5'-difluoro analogue 4o ($IC_{50}$=151 nM) are more potent than (2S,3S)-4a ($IC_{50}$=241 nM).

The only analogues that had sub-micromolar $IC_{50}$ values for inhibition of 5HT uptake were the (±)-3',4'-dichlorophenyl analogue (±)-4n ($IC_{50}$=360 nM) and the 2-napthyl analogue 4r ($IC_{50}$=334 nM). (2S,3S)-4a, (2R,3R)-4a and 16 of the analogues were inactive at the SERT. The remaining analogues had $IC_{50}$ values greater than 1560 nM.

Compound 2 has ~3-fold selectivity for inhibition at DA over NE uptake and is inactive at inhibition of 5HT uptake. Neither (2R,3R)-4a nor (2S,3S)-4a shows activity for 5HT uptake. Compound (2R,3R)-4a's poor activity overall precludes comments about its transporter selectivity. On the other hand, (2S,3S)-4a has the opposite DA/NE inhibition of uptake selectivity relative to 2, exhibiting ~3-fold selectivity for inhibition of uptake of NE over DA. Only the 2-napthyl analogue 4r shows selectivity for the SERT ($IC_{50}$=334 nM) compared to 453 and 1570 nM for DA and NE uptake inhibition. Analogues 4b-4g, 4l-4m, 4o-4q, 4s, and 4u-4v share with (2S,3S)-4a selectivity for inhibition of NE over DA uptake with selectivity for inhibition of NE over DA uptake being highest for the 3'-methoxyphenyl analogue 4f, the ethyl extended analogue 4s and N-methyl-4'-chorophenyl analogue 4v (5-fold each), the 3',5'-difluoro analogue 4o and N-methyl analogue 4u (7-8-fold) and the 3'-nitrophenyl 4g (10-fold) and the naphthyl analogue 4q (24-fold). However, relative to (2S,3S)-4a, only 4s and 4o have a combination of higher potency in NE uptake inhibition and selectivity for NE over DA uptake inhibition. The propyl-extended chain analogue, 4t, has much higher potency than (2S,3S)- or (2R,3R)-4a at each of the monoamine transporter targets, but it is essentially equipotent for NE and DA uptake inhibition ($IC_{50}$=31 and 30 nM). The only analogues tested with selectivity for inhibition of DA over NE uptake [discounting the small preference for DA over NE and 5HT inhibition shown by (±)-3',4'-dichlorophenyl analogue (±)-4n] are the 4'-chlorophenyl analogue 4i or 4'-methylphenyl analogues 4j and 2-napthyl analogue (4r) (3-5-fold). However, by contrast to 4r, the structurally related 1-napthyl analogue (4q) has 24-fold selectivity for inhibition of NE over DA uptake. Thus, alkyl extension as well as phenyl substitution can impact inhibitory potency and selectivity of the hydroxybupropion analogues for monoamine transporters.

nAChR Functional Assays:

Compound (2S,3S)-4a and analogues 4b-4v and 5 and 6 also were evaluated for their ability to antagonize functional responses of $\alpha3\beta4^*$-, $\alpha4\beta2$-, $\alpha4\beta4$-, and $\alpha1^*$-nAChR using previously reported methods (see Damaj, M. I.; Carroll, F. I.; Eaton, J. B.; Navarro, H. A.; Blough, B. E.; Mirza, S.; Lukas, R. J.; Martin, B. R., *Mol. Pharmacol.* 2004, 66, (3), 675-682), modified as described below. Effects of hydroxybupropion analogues 4b-4v and 5 and 6 on function of diverse, human nAChR subtypes naturally or heterologously expressed by human cell lines were assessed using $^{86}Rb^+$ efflux assays that are specific only for nAChR function in the cells used.

Cells were harvested at confluence from 100-mm plates by mild trypsinization (Irvine Scientific, Santa Ana, Calif.) and trituration or (for SH-SY5Y cells) by trituration alone before being suspended in complete medium and evenly seeded at a density of 1.25-2 confluent 100-mm plates per 24-well plate (Falcon; ~100-125 µg of total cell protein per well in a 500 µL volume). After cells had adhered (generally overnight, but no sooner than 4 h later), the medium was removed and replaced with 250 µL per well of complete medium supplemented with ~350,000 cpm of $^{86}Rb^+$ (PerkinElmer Life and Analytical Sciences, Boston, Mass.) and counted at 40% efficiency using Cerenkov counting (Tri-Carb 1900 liquid scintillation analyzer, 59% efficiency; PerkinElmer Life Sciences).

After at least 4 h and typically overnight, $^{86}Rb^+$ efflux was measured using the "flip-plate" technique. See Lukas, R. J.; Fryer, J. D.; Eaton, J. B.; L., G. C., Some methods for studies of nicotinic acetylcholine receptor pharmacology, in *Nicotinic receptors and the Nervous System*, Levine, E. D., Ed. CRC Press: Boca Raton, 2002; pp 3-27, incorporated herein by reference in its entirety). Briefly, after aspiration of the bulk of $^{86}Rb^+$ loading medium from each well of the "cell plate," each well containing cells was rinsed 3× with 2 mL of fresh $^{86}Rb^+$ efflux buffer (130 mM NaCl, 5.4 mM KCl, 2 mM CaCl$_2$, 5 mM glucose, 50 mM HEPES, pH 7.4) to remove extracellular $^{86}Rb^+$. Following removal of residual rinse buffer by aspiration, the flip-plate technique was used again to simultaneously introduce 1.5 mL of fresh efflux buffer containing drugs of choice at indicated final concentrations from a 24-well "efflux/drug plate" into the wells of the cell plate. After a 5 min incubation, the solution was "flipped" back into the efflux/drug plate, and any remaining buffer in the cell plate was removed by aspiration. Cells remaining in the cell plate were lysed and suspended by addition of 1.5 mL of 0.1 M NaOH, 0.1% sodium dodecyl sulfate to each well. Suspensions in each well were then subjected to Cerenkov counting (Wallac Micobeta Trilux 1450; 25% efficiency) after placement of inserts (Wallac 1450-109) into each well to minimize cross-talk between wells.

For quality control and normalization purposes, the sum of $^{86}Rb^+$ in cell plates and efflux/drug plates was defined to confirm material balance (i.e., that the sum of $^{86}Rb^+$ released into the efflux/drug plates and $^{86}Rb^+$ remaining in the cell plate were the same for each well). This assured that $^{86}Rb^+$ efflux was the same whether measured in absolute terms or as a percentage of loaded $^{86}Rb^+$. Similarly, the sum of $^{86}Rb^+$ in cell plates and efflux/drug plates also determined the efficiency of $^{86}Rb^+$ loading (the percentage of applied $^{86}Rb^+$ actually loaded into cells).

Control, total $^{86}Rb^+$ efflux was assessed in the presence of only a fully efficacious concentration of carbamylcholine (1 mM for SH-EP1-hα4β2, SH-EP1-hα4β4 cells or TE671/RD cells; 3 mM for SH-SY5Y cells). Control, non-specific $^{86}Rb^+$ efflux was measured either in the presence of the fully efficacious concentration of carbamylcholine plus 100 µM mecamylamine, which gave full block of agonist-induced and spontaneous nAChR-mediated ion flux, or in the presence of efflux buffer alone. Either determination of non-specific efflux was equivalent. Specific efflux was then taken as the difference in control samples between total and non-specific $^{86}Rb^+$ efflux. Any intrinsic agonist activity of test drugs was ascertained using samples containing test drug only at different concentrations and was normalized, after subtraction of non-specific efflux, to specific efflux in test drug-free, control samples. Antagonism of carbamylcholine-evoked $^{86}Rb^+$ efflux was assessed in samples containing the full agonist at a concentration where it stimulates 80-90% of maximal function (i.e., its EC$_{80}$-EC$_{90}$ value) when exposed alone to a given nAChR subtype (i.e., 460 µM for TE671/RD cells, 2 mM for SH-SY5Y cells; 200 µM for SH-EP1-hα4β2 or -α4β4 cells) and test drugs at the concentrations shown. After subtraction of non-specific efflux, results were normalized to specific ion flux in control samples. For studies of mechanism of antagonism, concentration-response curves were obtained using samples containing the full agonist, carbamylcholine, at the indicated concentrations alone or in the presence of a concentration of the test ligand close to its IC$_{50}$ value for inhibition of nAChR function. In other studies, cells were pre-exposed to analogues for 1 h (over the last hour of $^{86}Rb^+$ loading) or 1 day (with $^{86}Rb^+$ loading occurring during the final 4 h of drug pretreatment) before effects on nAChR function were assessed after analogue was removed (during extracellular $^{86}Rb^+$ removal) or in the continued presence of drug.

Ion flux assay results were fit using Prism (GraphPad) to the Hill equation, $F=F_{max}/(1+(X/Z)^n)$, where F is the test sample specific ion flux as a percentage of control, $F_{max}$ is specific ion flux in the absence of test drug (i.e., for control samples), X is the test ligand concentration, Z is the EC$_{50}$ (n>0 for agonists) or IC$_{50}$ (n<0 for antagonists), and n is the Hill coefficient. All concentration-ion flux response curves were simple and fit well allowing maximum and minimum ion flux values to be determined by curve fitting, but in cases where antagonists had weak functional potency, minimum ion flux was set at 0% of control. Note that because agonist concentrations used for test ligand antagonism assessments were EC$_{80}$-EC$_{90}$ values, not all of the data, even at the lowest concentrations of test antagonist, approaches 100% of specific efflux as separately determined in sister samples exposed to fully efficacious concentrations of agonist. Results are given in Table 4 below.

Relative to 2 (IC$_{50}$=7.9 nM), (2R,3R)-4a has comparable activity at α1*-nAChR (IC$_{50}$=7.6 nM), but (2R,3R)-4a is weaker in its interactions at α4β2- and α4β4-nAChR, although it retains 2's selectivity for action at α3β4*-nAChR. As was previously noted, (2S,3S)-4a has an altered nAChR functional inhibitory profile relative to 2, showing higher potency at α4β2-nAChR (IC$_{50}$=3.3 µM compared to 12 µM for 2) and higher selectivity for α4β2- over other nAChR (~3-fold).

Relative to (2R,3R)-4a and (2S,3S)-4a (IC$_{50}$ values of 6.5 and 11 µM, respectively), the 3'-deschlorophenyl-analogue 4b, and the 3'-methylphenyl and 4'-methylphenyl-analogues 4e and 4j have comparable inhibitory potencies at α3β4*-nAChR (IC$_{50}$=8.5-8.9 µM). By contrast, there is slightly higher potency at α3β4*-nAChR for the 3'-bromophenyl 4d, 3'-chlorophenyl-4-(N-methyl) 4u, ethyl and propyl chain extended analogues 4s and 4t, 4'-chloro 4i, 3',5'-dichlorophenyl 4p, 1-naphthyl 4q, and 4'-chloro-4-(N-methyl) 4v analogues (IC$_{50}$=3.2-6.5 µM). Having slightly higher antagonist potencies at α3β4*-nAChR are the (±)-3',4'-dichlorophenyl analogue, (±)-4n and the 2-naphthyl analogue 4r (IC$_{50}$ values of 2.6 and 2.0 µM, respectively, but the only analogue with higher potency than 2 (1.8 µM IC$_{50}$) at α3β4*-nAChR is the biphenyl analogue 4l (IC$_{50}$=1.3 µM). For these analogues, IC$_{50}$ values for inhibition of α1*-nAChR function are higher (>33 µM for 4b, 4e, 4u, and 4v) or are in the range (5.9-19 µM for 4d, 4i-4j, 4l, (±)-4n, 4p-4t) of IC$_{50}$ values for inhibition of α1*-nAChR by (2S,3S)-4a or (2R,3R)-4a (28 or 7.6 µM, respectively).

In absolute terms, the 3'-bromophenyl- (4d), 3'-fluorophenyl- (4c), biphenyl 4l, and ethyl extended chain analogue 4s have higher inhibitory potency at α4β2-nAChR than (2S, 3S)-4a (IC$_{50}$ values of 0.55, 1.3, 1.8 and 2.9 relative to 3.3 µM, respectively).

Of the analogues tested, 4i-4l, (±)-4n, 4p-4q, 4t, and 4v and the 2-napthyl derivative 4r have selectivity as does 2 for α3β4*-nAChR over the other nAChR subtypes (but never more than 4-fold, except for 4v having ~9-fold selectivity). (2R,3R)-4a is barely selective for α3β4*-nAChR over α1*-nAChR, but about 5-fold selective for α3β4*- over α4β2-nAChR. Of all the analogues tested, 4b-4e, 4g-4h, 4o and 4s have selectivity for α4β2-nAChR over other nAChR subtypes. Compounds 4f, 4m and 4u are about equipotent at α4β2- and α3β4*-nAChR. From another perspective, only the racemic 3',4'-dicholoro (±)-4n (~8-fold) and 4'-chloro-4-(N-methyl) 4v (~9-fold) have higher selectivity for α3β4*- over α4β2-nAChR than (2R,3R)-4a (~5-fold) or 2 (~6.7-fold). The 3'-fluorophenyl 4c (~12-fold), 3'-bromophenyl 4d (~6-fold), and 3'-nitrophenyl 4g (~3-fold) analogues have selectivity for α4β2-nAChR over other nAChR subtypes better than or comparable to that for (2S,3S)-4a (~3-fold).

None of the analogues has activity as agonist at α1*-, α3β4*-, α4β2-, or α4β4-nAChR, because $^{86}Rb^+$ efflux in the presence of these ligands alone at concentrations from ~5 nM to 100 μM (data not shown here) was indistinguishable from responses in cells exposed only to efflux buffer.

We compared inhibitory potencies across transporters and nAChR relative to (2S,3S)-4a, which has ~3-fold selectivity for inhibition of NE over DA uptake inhibition and ~14-fold selectivity for inhibition of NE uptake inhibition over α4β2-nAChR function. Interestingly, there is a change to absolute selectivity for inhibition of α4β2-nAChR over NE uptake inhibition (~1.7-fold) or over DA uptake inhibition (~6-fold) (and ~3.6-fold selectivity for inhibition of NE over DA uptake) for 3'-bromophenyl 4d. There is an even more striking increase in selectivity for inhibition of α4β2-nAChR function for biphenyl analogue 4l (>5-fold over DA uptake inhibition and 6-fold over NE uptake inhibition), which, however, is slightly selective for inhibition of α3β4*-nAChR over α4β2-nAChR.

Selectivity for inhibition of NE uptake inhibition over α4β2-nAChR function also is reduced for analogues 4c (~1.7-fold), 4h (~3-fold), 4f (~3.3-fold), 4g and 4r (~4-fold), 4e (~5.3-fold), and 4b (~12-fold), and for analogue 4p (~4.5-fold). Conversely, there is an increase in selectivity for inhibition of NE uptake over α4β2-nAChR function for 4t (~240-fold), (±)-4n (~175-fold), 4v (80-fold), 4s (~67-fold), and 4o (42-fold), although selectivity for inhibition of NE uptake over inhibition of α3β4*- instead of α4<2-nAChR function is less for 4t, (±)-4n, and 4v (~154-, 23-, and 9-fold, respectively; recall that 4t has comparable activity for DA and NE uptake inhibition). Although its selectivity for inhibition of DA over NE uptake is marginal, (±)-4n has ~37-fold selectivity for inhibition of DA uptake over α3β4*-nAChR and >285-fold selectivity for inhibition of DA uptake over α4β2-nAChR. For 4r and 4p, selectivity for inhibition of NE uptake over α3β4*-nAChR function is marginal (1.3- and 1.6-fold, respectively), but biphenyl 4l has 7.9-fold selectivity for inhibition of α3β4*-nAChR over inhibition of NE uptake, surpassing selectivity seen for (2R,3R)-4a (~1.5-fold).

TABLE 4

Inhibition of monoamine uptake and nAChR function for hydroxybupropion analogs

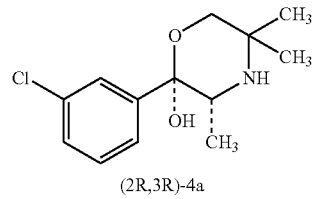 [SMILES: C[C@H]1NC(C)(C)CO[C@]1(O)c1cccc(Cl)c1]

(2R,3R)-4a

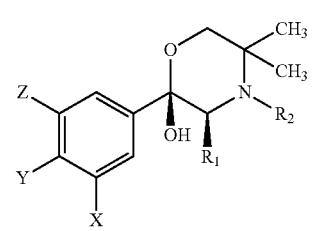

4

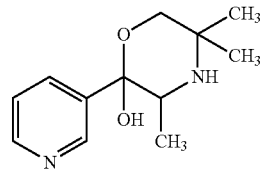 [SMILES: CC1NC(C)(C)COC1(O)c1cccnc1]

5

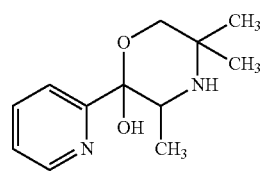 [SMILES: CC1NC(C)(C)COC1(O)c1ccccn1]

6

TABLE 4-continued

| Cmpd[c] | R₁ | R₂ | X | Y | Z | monoamine uptake inhibition[a] IC50 (nM) | | |
|---|---|---|---|---|---|---|---|---|
| | | | | | | [³H]DA | [³H]NE | [³H]5HT |
| 2 | — | — | | | | 660 ± 178 | 1850 ± 300 | IA |
| (2R,3R)-4a | CH₃ | H | Cl | H | H | IA | 9900 ± 1400 | IA |
| (2S,3S)-4a | CH₃ | H | Cl | H | H | 630 ± 50 | 241 ± 60 | IA |
| 4b | CH₃ | H | H | H | H | 1065 ± 30 | 550 ± 90 | IA |
| 4c | CH₃ | H | F | H | H | 1380 ± 360 | 740 ± 150 | IA |
| 4d | CH₃ | H | Br | H | H | 3340 ± 680 | 920 ± 300 | IA |
| 4e | CH₃ | H | CH₃ | H | H | 2600 ± 400 | 1130 ± 20 | IA |
| 4f | CH₃ | H | CH₃O | H | H | 16,000 ± 2000 | 3000 ± 900 | IA |
| 4g | CH₃ | H | NO₂ | H | H | 12,000 ± 4000 | 1210 ± 340 | IA |
| 4h | CH₃ | H | H | F | H | 4200 ± 700 | 3800 ± 600 | IA |
| 4i | CH₃ | H | H | Cl | H | 285 ± 70 | 830 ± 90 | 4600 ± 900 |
| 4j | CH₃ | H | H | CH₃ | H | 832 ± 260 | 1680 ± 330 | IA |
| 4k | CH₃ | H | H | CH₃O | H | IA | IA | IA |
| 4l | CH₃ | H | H | C₆H₅ | H | IA | 10,300 ± 1500 | IA |
| 4m | CH₃ | H | F | F | H | 2140 ± 180 | 740 ± 110 | IA |
| 4n[c] | CH₃ | H | Cl | Cl | H | 70 ± 20 | 114 ± 30 | 360 ± 40 |
| 4o | CH₃ | H | F | H | F | 1020 ± 190 | 151 ± 43 | IA |
| 4p[c] | CH₃ | H | Cl | H | Cl | 8250 ± 720 | 2440 ± 730 | IA |
| 4q | CH₃ | H | 1-napthyl | | | 10,000 ± 4000 | 411 ± 53 | 1565 ± 40 |
| 4r | CH₃ | H | 2-napthyl | | | 453 ± 4 | 1570 ± 430 | 334 ± 42 |
| 4s | C₂H₅ | H | Cl | H | H | 204 ± 23 | 43.4 ± 72 | 2500 ± 540 |
| 4t | C₃H₇ | H | Cl | H | H | 30 ± 4 | 31 ± 10 | 4130 ± 770 |
| 4u | CH₃ | CH₃ | Cl | H | H | 3400 ± 600 | 415 ± 9 | IA |
| 4v | CH₃ | CH₃ | H | Cl | H | 2870 ± 820 | 527 ± 104 | 6480 ± 1280 |
| 5[c] | | | | | | IA | IA | IA |
| 6[c] | | | | | | IA | 7950 ± 1800 | IA |

| Cmpd[c] | R₁ | R₂ | X | Y | Z | nAChR inhibition[b] IC₅₀ (μM) | | | |
|---|---|---|---|---|---|---|---|---|---|
| | | | | | | α3β4* | α4β2 | α4β4 | α1*β1 |
| 2 | | | | | | 1.8 (1.15) | 12 (1.15) | 12 (1.07) | 7.9 (1.12) |
| (2R,3R)-4a | CH₃ | H | Cl | H | H | 6.5 (1.20) | 31 (1.12) | 41 (1.07) | 7.6 (1.12) |
| (2S,3S)-4a | CH₃ | H | Cl | H | H | 11 (1.48) | 3.3 (1.07) | 30 (1.10) | 28 (1.45) |
| 4b | CH₃ | H | H | H | H | 8.9 (1.23) | 6.4 (1.23) | 92 (1.29) | IA |
| 4c | CH₃ | H | F | H | H | 15 (1.12) | 1.3 (1.17) | IA | IA |
| 4d | CH₃ | H | Br | H | H | 3.2 (1.12) | 0.55 (1.23) | 30 (1.07) | 18 (1.07) |
| 4e | CH₃ | H | CH₃ | H | H | 8.6 (1.12) | 6.0 (1.20) | 64 (1.20) | 33 (1.07) |
| 4f | CH₃ | H | CH₃O | H | H | 11 (1.07) | 10 (1.26) | IA | 49 (1.07) |
| 4g | CH₃ | H | NO₂ | H | H | 14 (1.10) | 4.8 (1.26) | 80 (1.10) | 96 (1.10) |
| 4h | CH₃ | H | H | F | H | 20 (1.15) | 12 (1.15) | IA | 69 (1.17) |
| 4i | CH₃ | H | H | Cl | H | 5.1 (1.07) | 9.2 (1.17) | 33 (0.05) | 19 (1.15) |
| 4j | CH₃ | H | H | CH₃ | H | 8.6 (1.07) | 12 (1.12) | 62 (1.10) | 20 (1.15) |
| 4k | CH₃ | H | H | CH₃O | H | 11 (1.10) | 27 (1.23) | 72 (1.12) | 25 (1.10) |
| 4l | CH₃ | H | H | C₆H₅ | H | 1.3 (1.12) | 1.8 (1.12) | 8.1 (1.07) | 5.9 (1.15) |
| 4m | CH₃ | H | F | F | H | 11.9 (1.15) | 12 (1.07) | IA | 36 (1.2) |
| 4n[c] | CH₃ | H | Cl | Cl | H | 2.6 (1.10) | 20 (1.07) | 14 (1.17) | 7.2 (1.12) |
| 4o | CH₃ | H | F | H | F | 11 (1.15) | 6.3 (1.51) | 62 (1.07) | 23 (1.12) |
| 4p[c] | CH₃ | H | Cl | H | Cl | 3.9 (1.07) | 11 (1.05) | 18 (1.17) | 7.2 (1.07) |
| 4q | CH₃ | H | 1-napthyl | | | 5.2 (1.15) | 9.0 (1.07) | 13 (1.10) | 6.6 (1.10) |
| 4r | CH₃ | H | 2-napthyl | | | 2.0 (1.05) | 6.5 (1.07) | 11 (1.10) | 11 (1.12) |

TABLE 4-continued

| | | | | | | | | |
|---|---|---|---|---|---|---|---|---|
| 4s | C$_2$H$_5$ | H | Cl | H | H | 4.3 (1.12) | 2.9 (1.10) | 16 (1.05) | 14 (1.10) |
| 4t | C$_3$H$_7$ | H | Cl | H | H | 4.8 (1.10) | 7.5 (1.05) | 18 (1.07) | 10 (1.07) |
| 4u | CH$_3$ | CH$_3$ | Cl | H | H | 6.5 (1.05) | 7.1 (1.07) | 43 (1.20) | 57 (1.05) |
| 4v | CH$_3$ | CH$_3$ | H | Cl | H | 4.6 (1.15) | 42 (1.17) | 91 (1.12) | 43 (1.05) |
| 5$^c$ | | | | | | IA | IA | IA | IA |
| 6$^c$ | | | | | | | | | |

$^a$Values for mean ± standard error of three independent experiments, each conducted with triplicate determination.
$^b$Mean micromolar IC$_{50}$ values (to two significant digits) for bupropion and the indicated analogs from three independent experiments for inhibition of functional responses to an EC$_{80}$-EC$_{90}$ concentration of carbamylcholine mediated by nAChR subtypes composed of the indicated subunits (where * indicates that additional subunits are or may be additional assembly partners with the subunits specified; see Methods and Materials). Numbers in parentheses indicate S.E.M. as a multiplication/division factor of the mean micromolar IC$_{50}$ values shown [i.e., the value 1.8 (1.15) reflects a mean IC$_{50}$ value of 1.8 µM with an S.E.M. range of 1.8 × 1.15 µM to 1.8/1.15 µM or 1.6-2.1 µM]. The value 11 (1.48) reflects a mean IC$_{50}$ value of 11 µM with an S.E.M. range of 11 × 1.40 µM to 11/1.48 µM or 7.4-16 µM. IA: IC$_{50}$ > 100 µM.
$^c$Compounds 4b-4m, and 4o-4v are all (2S, 3S)-isomers. Compounds 4n, 4p, 5, and 6 are racemic materials.

$^{86}$Rb$^+$ efflux assays also were used to assess whether ligands had activity as antagonists at human nAChR. Representative concentration-response curves for selected ligands (2S,3S)-4a, 4d, 4c, and 4g (FIG. 1) and (2R,3R)-4a, 4s, 4u, and 4t (FIG. 2) illustrate nAChR in vitro inhibitory profiles (see also Table 4).

FIG. 1 shows specific $^{86}$Rb$^+$ efflux (ordinate; percentage of control) determined for functional, human muscle-type α1β1γδ-nAChR (●), ganglionic α3β4*-nAChR (○), α4β2-nAChR (▲) or α4β4-nAChR (▽) naturally or heterologously expressed in human cell lines in the presence of a receptor subtype-specific, EC$_{80}$-EC$_{90}$ concentration of the full agonist, carbamylcholine, either alone or in the presence of the indicated concentrations (abscissa, log molar) of (2S,3S)-hydroxybupropion [(2S,3S)-4a] or its analogues (compounds 4d, 4c, and 4g) as indicated. Mean micromolar IC$_{50}$ values and SEM as a multiplication/division factor of the mean micromolar IC$_{50}$ value are provided in Table 4. FIG. 2 shows Specific $^{86}$Rb$^+$ efflux (ordinate; percentage of control) determined for functional, human muscle-type α1β1γδ-nAChR (●), ganglionic α3β4*-nAChR (○), α4β2-nAChR (▲) or α4β4-nAChR (▽) naturally or heterologously expressed in human cell lines in the presence of a receptor subtype-specific, EC$_{80}$-EC$_{90}$ concentration of the full agonist, carbamylcholine, either alone or in the presence of the indicated concentrations (abscissa, log molar) of (2R,3R)-hydroxybupropion [(2R,3R)-4a] or analogues (compounds 4s, 4u, and 4t) as indicated. Mean micromolar IC$_{50}$ values and SEM as a multiplication/division factor of the mean micromolar IC$_{50}$ value are provided in Table 4.

Not shown here are other studies demonstrating that antagonism in all cases was mediated non-competitively, in that agonist concentration-ion flux response curves in the presence of ~IC$_{50}$ concentrations of analogues showed diminished efficacy of agonist relative to response curves obtained in the absence of analogues and that agonist apparent EC$_{50}$ values were unaffected by the presence of analogs.

b) In Vivo Studies

Compound (2S,3S)-4a analogues 4b-4v and 5 and 6 also were evaluated for their ability to antagonize behavioral responses to acute nicotine administration as previously described in Damaj, M. I.; Carroll, F. I.; Eaton, J. B.; Navarro, H. A.; Blough, B. E.; Mirza, S.; Lukas, R. J.; Martin, B. R., *Mol. Pharmacol.* 2004, 66, (3), 675-682. The tests are described below and results are given in Table 5.

Behavior:

All animal experiments were conducted in accordance with the NIH Guide for the Care and Use of Laboratory Animals and Institutional Animal Care and Use Committee guidelines.

Animals:

Male Institute of Cancer Research (ICR) mice (weighing 20-25 g) obtained from Harlan (Indianapolis, Ind.) were used throughout the study. Animals were housed in an Association for Assessment and Accreditation of Laboratory Animal Care-approved facility, were placed in groups of six, and had free access to food and water. Studies were approved by the Institutional Animal Care and Use Committee of Virginia Commonwealth University.

Tail-Flick Test:

Antinociception for pain mediated at the spinal level was assessed by the tail-flick method of D'Amour, F. E.; Smith, D. L., *J. Pharmacol. Exp. Ther.* 1941, 72, 74-79, incorporated herein by reference in its entirety. In brief, mice were lightly restrained while a radiant heat source was shone onto the upper portion of the tail. To minimize tissue damage, a maximum latency of 10 s was imposed. Latency to remove the tail from the heat source was recorded for each animal. A control response (2-4 s) was determined for each mouse before treatment, and a test latency was determined after drug administration (nicotine as an analgesic 5 min after subcutaneous administration at 2.5 mg/kg; nicotine administration 15 min after exposure to saline of bupropion analogue to assess the latter drug's ability to block nicotine-mediated antinociception). Antinociceptive response was calculated as the percentage of maximum possible effect (% MPE), where % MPE=[(test control)/(10 control)]×100.

Hot-Plate Test:

Mice were placed into a 10-cm wide glass cylinder on a hot plate (Thermojust Apparatus) maintained at 55° C. for assessment of pain responses mediated at supraspinal levels. To minimize tissue damage, a maximum exposure to the hot plate 40 s was imposed. Measures of control latencies (time until the animal jumped or licked its paws; typically 8-12 s) were done twice for stimuli applied at least 10 min apart for each mouse. Antinociceptive responses after test drug administrations were determined and calculated as the % MPE, where % MPE=[(test latency in s−control latency in s)/(40 s−control latency in s)×100]. Groups of 8 to 12 animals were used for each drug condition. Antagonism studies were carried in mice pretreated with either saline or bupropion metabolites 15 min before nicotine administration. The animals were then tested 5 min after administration of a subcutaneous dose of 2.5 mg/kg nicotine.

Locomotor Activity:

Mice were placed into individual Omnitech photocell activity cages (28×16.5 cm; Omnitech Electronics, Columbus, Ohio) 5 min after subcutaneous administration of either 0.9% saline or nicotine (1.5 mg/kg). Interruptions of the photocell beams (two banks of eight cells each) were then recorded for the next 10 min. Data were expressed as the number of photocell interruptions. Antagonism studies were carried out by pretreating the mice with either saline or bupropion metabolites 15 min before nicotine administration.

Body Temperature:

Rectal temperature was measured by a thermistor probe (inserted 24 mm) and digital thermometer (YSI Inc., Yellow Springs, Ohio). Readings were taken just before and 30 min after subcutaneous injection of either saline or 2.5 mg/kg nicotine. The difference in rectal temperature before and after treatment was calculated for each mouse. The ambient temperature of the laboratory varied from 21 to 24° C. from day to day. Antagonism studies were carried out by pretreating the mice with either saline or bupropion metabolites 15 min before nicotine administration. The animals were then tested 30 min after administration of a subcutaneous dose of 2.5 mg/kg nicotine.

Results:

Compound 2 blocks nicotine-induced increases in locomotor activity with an $AD_{50}$ value of 4.9 mg/kg, while (2S,3S)-4a has a lower $AD_{50}$ value of 0.9 mg/kg in the same assay, but none of the analogues is better than (2S,3S)-4a, although 4d and 4p (2.6 and 1.9 mg/kg $AD_{50}$, respectively) have slightly higher potency than 2.

The ability of (2S,3S)-4a to block the nicotine-induced decrease in body temperature is lower than that for 2 $AD_{50}$=1.5 and 9.2 mg/kg, respectively. Compound 4d ($AD_{50}$=1.7 mg/kg) also rivals (2S,3S)-4a in this assay, analogues 4c, 4e, 4g, 4h, and 4s have intermediate potencies (2.3-7 mg/kg $AD_{50}$ values).

In the hot-plate assay, 2 blocks nicotine-induced, supraspinally-mediated analgesia with an $AD_{50}$ value of 15 mg/kg. Compound (2S,3S)-4a is 15-fold more potent ($AD_{50}$ value of 1 mg/kg), but blockade of nicotine-induced hot-plate analgesia is no better for any of the new analogues tested. However, 4c, 4d, 4e, and 4s (3.7-8.6 mg/kg $AD_{50}$ values) are more potent than 2.

Nicotine-induced analgesia in the tail flick assay, which assesses spinal processes involved in nicotine antinociception,[27] is blocked by 2 with an $AD_{50}$ of 1.2 mg/kg. Compound (2S,3S)-4a with an $AD_{50}$=0.2 mg/kg has a 6-fold increase in effectiveness in this assay. Fifteen of the new analogues have even higher potency. $AD_{50}$ values (in mg/kg) are 0.004 for 4j, 4s, and 4t; ~0.006 for 4m and 4o; 0.012-0.013 for 4c and 4h; 0.016 for 4u; 0.019 for 4i and 4k; 0.021 for 4l; between 0.034 and 0.054 for 4q, 4r, and 4e; and 0.16 for 4d.

Thus, in four assays of the ability of analogues to block acute actions of nicotine, 3'-bromophenyl analogue 4d was more effective than 2 in each and rivaled effects of (2S,3S)-4a in tail-flick and hypothermia assessments. The 3'-fluorophenyl analogue 4c, 3'-methylphenyl analogue 4e, and ethyl extended chain analogue 4s exceeded 2's potency in three assays and had higher potency than (2S,3S)-4a in the tail-flick assay. Compounds 4c, 4d, and 4s also are remarkable for their higher inhibitory effectiveness at α4β2-nAChR than (2S,3S)-4a. Eleven of the other ligands had better effectiveness than 2 in one of the acute assays, with potency in the tail-flick assay correlating with $IC_{50}$ values <10 μM for inhibition of α4β2-nAChR function for 4c-4e, 4l, 4o, and 4q-4u, but not for 4h-4k, 4m and 4v, which were potent in the tail-flick assay but not as α4β2-nAChR antagonists, or for 4b, 4f and 4g, which lacked effectiveness relative to (2S,3S)-4a in the tail-flick assay but have sub-10 μM $IC_{50}$ values at α4β2-nAChR. Lacking potency in tail-flick or inhibition of α4β2-nAChR function, but having activity as antagonists of α3β4*-nAChR, are 4n and 4p. Increased in vitro inhibition of DA and NE uptake did not necessarily correlate with increased in vivo inhibitory potency in nicotine-sensitive assays if there also was no increase in effectiveness at α4β2-nAChR or selectivity for that target (e.g., 4n). On the other hand, the ligands with the highest inhibitory potency for NE uptake inhibition (and highest or higher effectiveness than (2S,3S)-4a at DA uptake inhibition) were among the most potent inhibitors of nicotine-induced analgesia in the tail-flick assay (4s and 4t). Improvement over (2S,3S)-4a in the ability to block nicotine-induced analgesia in the tail-flick assay as seen for 4j, 4m, and 4o has no obvious basis as judged from in vitro assays.

TABLE 5

Pharmacological evaluation of hydroxybupropion analogs as non-competitive nicotinic antagonists[a]

| Compound[b] | $AD_{50}$ (mg/kg) | | | |
|---|---|---|---|---|
| | Tail-flick[c] | Hot-plate[c] | Locomotion[c] | Hypothermia[c] |
| 2 | 1.2 (1-1.8) | 15 (6-19) | 4.9 (0.9-46) | 9.2 (4-23) |
| (2S,3S)-4a | 0.2 (0.1-1.1) | 1.0 (0.5-4.5) | 0.9 (0.38-3.7) | 1.5 (0.95-2.6) |
| (2R,3R)-4a | 2.5 (1.7-3.5) | 10.3 (8.9-15) | IA | IA |
| 4b | IA | IA | IA | IA |
| 4c | 0.012 (0.002-0.16) | 8.6 (0.7-10.5) | IA | 4.4 (1.3-14.5) |
| 4d | 0.16 (0.05-0.6) | 4.3 (1.8-9.8) | 2.6 (0.7-10.1) | 1.7 (0.5-6.8) |
| 4e | 0.054 (0.04-0.066) | 7.6 (2-29) | IA | 2.3 (0.4-11) |
| 4f | 5.85 (3.8-8.8) | IA | IA | IA |
| 4g | 4.9 (1.6-15) | IA | IA | 4.7 (3.5-6.2) |
| 4h | 0.013 (0.005-0.03) | IA | IA | 5.67 (2.5-12.8) |
| 4i | 0.019 (0.063-0.1) | IA | IA | IA |
| 4j | 0.004 (0.002-0.012) | IA | IA | IA |
| 4k | 0.019 (0.06-0.064) | IA | IA | IA |
| 4l | 0.021 (0.005-0.1) | IA | IA | IA |
| 4m | 0.006 (0.004-0.01) | IA | IA | IA |
| 4n | 8.8 (4.3-18) | IA | IA | IA |
| 4o | 0.0056 (0.004-0.009) | IA | IA | IA |
| 4p | IA | IA | 1.9 | IA |
| 4q | 0.034 (0.001-0.1) | IA | IA | IA |
| 4r | 0.04 (0.001-0.6) | IA | IA | IA |
| 4s | 0.004 (0.001-0.03) | 3.7 (0.8-17) | 10.3 (1.4-75) | 7 (4.5-10.8) |
| 4t | 0.004 (0.001-0.03) | IA | 4.7 | IA |
| 4u | 0.016 (0.004-0.06) | IA | IA | IA |

TABLE 5-continued

Pharmacological evaluation of hydroxybupropion analogs as non-competitive nicotinic antagonists[a]

| Compound[b] | Tail-flick[c] | AD$_{50}$ (mg/kg) | | |
|---|---|---|---|---|
| | | Hot-plate[c] | Locomotion[c] | Hypothermia[c] |
| 4v | 0.32 (0.04-2.5) | IA | IA | IA |
| 5 | n/a | n/a | n/a | n/a |
| 6 | n/a | n/a | n/a | n/a |

[a]Results were expressed as AD$_{50}$ (mg/kg) ± confidence limits (CL) or % effect at the highest dose tested. Dose-response curves were determined using a minimum of four different doses of test compound, and at least eight mice were used per dose group.
[b]Compounds 4b-4m, and 4o-4v are all (2S,3S)-isomers. Compounds 4n, 4p, 5, and 6 are racemic materials.
[c]n/a: not assayed; IA: AD$_{50}$ > 15 mg/kg; NFT = no further testing.

c) Overview of Biological Studies

Analogues were generated with higher inhibitory potency than 2 (bupropion) or either of its hydroxymetabolite isomers (2R,3R)-4a and (2S,3S)-4a for DA uptake inhibition (4i, 4n, 4r, 4s, and 4t), NE uptake inhibition [(±)-4n, 4o, 4s, and 4t], or 5HT uptake inhibition [(±)-4n and 4r], of for functional inhibition of α3β4*-nAChR (4l) or α4β2-nAChR (4c, 4d, 4l and 4s). Selectivity for inhibition of DA uptake over nAChR functional blockade or NE uptake inhibition like that of 2 was achieved for 4r (except that this ligand is a slightly selective inhibitor of 5HT over DA uptake). Selectivity for inhibition of DA uptake over nAChR or NE uptake inhibition better than that of 2 was achieved with retention of reasonable potency at DAT for 4i. As predicted based on our previous studies of hydroxymetabolites, many of the compounds evaluated have selectivity for inhibition of NE over DA uptake. This was improved relative to (2S,3S)-4a for 4f-4g, 4s, 4v, 4o, 4u and 4q, but only 4s and 4o have improved potency at NE uptake inhibition. Compounds (±)-4n, 4t, and 4s are more selective than (2S,3S)-4a for inhibition of NE uptake inhibition over nAChR function. Only (±)-4n and 4v have increased selectivity for α3β4*-nAChR over other nAChR subtypes relative to 2 or (2R,3R)-4a. Compounds 4l and 4k have improved selectivity for α3β4*-nAChR functional inhibition over DA and NE uptake inhibition relative to that of (2R,3R)-4a. Compound 4d has absolute selectivity for inhibition of α4β2-nAChRs over inhibition of α3β4*-nAChR as well as over NE, 5HT or DA uptake inhibition, and 4l's similar potency at α4β2- and α3β4*-nAChR also means that it is selective for inhibition of α4β2-nAChRs over monoamine transporters. Selectivity for α4β2-nAChR over α3β4*- and other nAChR subtypes was increased for 4c and 4d relative to that for 2 and (2S,3S)-4a. Selectivity for inhibition of NE uptake inhibition over α4β2-nAChRs was reduced relative to that of (2S,3S)-4a for 4b, 4c, 4e, 4f, 4g, 4p, and 4r, with 4d actually being absolutely selective for inhibition of α4β2-nAChRs function over other nAChR subtypes and over inhibition of DA and NE uptake.

From a chemical structure perspective, changes in the 3'-chlorophenyl group in (2S,3S)-4a to 3'-bromophenyl 4d or 3'-fluorophenyl 4c afforded ligands with improved affinity and selectivity for α4β2-nAChRs. Selectivity for monoamine transporter uptake over α4β2-nAChRs functional block was decreased while selectivity for α4β2-nAChRs over other nAChR subtypes was preserved by other changes in the phenyl substitution (nitro 4g, methyl 4e) or lack of chloro group (4b) but not for 3'-methoxyphenyl substitution (4f). The dichlorophenyl analogues (±)-4n and 4p have increased selectivity for α3β4*-nAChR over other nAChR subtypes. In addition, the (±)-3',4'-dichlorophenyl analogue [(±)-4n] also has a marked increase in affinity for inhibition of DA uptake. Replacement of the 3-methyl group on the morpholinol ring with an ethyl or propyl group (4s and 4t) affords ligands with notable improvements in selectivity for inhibition of NE uptake over nAChR and increases in potencies for inhibition of DA and NE uptake. Changing the 3-chlorophenyl ring to a pyridine ring leads to ligands 5 and 6, which are without activity. Naphthyl analogues 4q and 4r have modestly altered activities compared to (2S,3S)-4a. Interestingly, moving the 3-substituent of the phenyl group of (2S,3S)-4a and 4e to the 4' position affords ligands (4i-4j) that are selective for DA over NE uptake and nAChR functional inhibition and for inhibition of α3β4*- over α4β2-nAChRs. However, the biphenyl analogue (4l) has almost no activity at monoamine transporters yet is very potent as an inhibitor of α4β2 and α3β4*-nAChR. Moving the 3'-substituent of the phenyl group of the N-methyl analogue 4u to the 4' position (4v) has little effect on inhibition or DA or NE uptake but increases selectivity for functional blockage of α3β4*- over α4β2-nAChRs from negligible to ~9-fold.

In silico predictions that all of the compounds synthesized would have drug-like character and activity in the central nervous system were consistent with the results of behavioral studies. We obtained several analogues with higher potency than (2S,3S)-4a or 2 as antagonists of nicotine-mediated antinociception in the tail-flick assay. The ethyl and propyl extended chain ligands 4s and 4t with high affinity for inhibition of DA and NE uptake, 3'-fluoro and 3'-bromo phenyl substituted analogues 4c and 4d with high affinity and good selectivity for α4β2-nAChRs, and to a lesser extent the 3'-methylphenyl analogue 4e also with good activity at α4β2-nAChRs, also had better potency in the tail-flick assay than 2 or (2S,3S)-4a. The naphthyl analogues 4q and 4r with selectivity for inhibition of NE over DA uptake and for inhibition of DA over NE uptake, respectively, but having comparable effects on nAChR function, had ~5-fold higher activity in the tail-flick assay than (2S,3S)-4a. However, the other in vivo assays mostly did not reveal striking inhibition by analogues of acute nicotine action. Moreover, the tail-flick assay could reflect CNS actions of ligands at higher level than the presumed spinal level of nicotine-mediated antinociception in the test.

Extensions of the $R_1$ methyl group in (2S,3S)-4a to an ethyl or propyl group (4s and 4t) preferentially improve activities for inhibition of DA and NE uptake. The naphthyl analogues (4q and 4r) afford ligands with better potency for 5HT uptake inhibition, and changing the 3'-chlorophenyl moiety of (2S,3S)-4a to a 3'-fluoro or 3'-bromophenyl group leads to ligands with better activity at α4β2-nAChRs (4c and 4d).

Even for assays that are done soon after delivery, the chemical modifications that selectively increase in vitro activity at transporters or at α4β2-nAChR afford ligands with potential as nicotine antagonists in vivo. That is, increased activity at either α4β2-nAChRs or for inhibition of DA or NE uptake (or for one ligand, at 5HT uptake inhibition) correlates well with improvement in ligand antagonist potency in the tail-flick assay. Thus, the behavioral results suggest that effects of nicotine dependence and/or depression could be countered by ligands acting at DAT, NET, or α4β2-nAChR or any combination of the three.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A compound according to the structure:

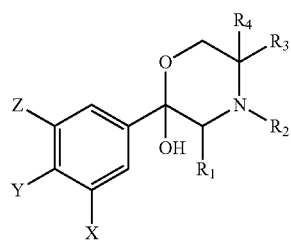

wherein:
- $R_1$ is optionally substituted C1-10 alkyl;
- $R_2$ is H or optionally substituted C1-10 alkyl;
- $R_3$ and $R_4$ are each independently selected from optionally substituted C1-10 alkyl;
- X is selected from optionally substituted C1-10 alkyl; optionally substituted C1-10 alkoxy; optionally substituted C2-10 alkenyl; optionally substituted C2-10 alkynyl; optionally substituted C6-C12 aryl; alkaryl; arylalkyl; aryloxy; optionally substituted heteroaryl; optionally substituted heterocycle; halo other than chloro; hydroxyl; halogenated alkyl; an amino group of formula $NH_2$, $NR_{12}H$, or $NR_{12}R_{13}$; alkylamino; arylamino; acyl; CN; $NO_2$; $N_3$; $CH_2OH$; $CONH_2$; $CONR_{12}R_{13}$; $CO_2R_{12}$; $CH_2OR_{12}$; $NHCOR_{12}$; $NHCO_2R_{12}$; C1-3 alkylthio; sulfate; sulfonic acid; sulfonate ester; phosphonic acid; phosphate; phosphonate; mono-, di-, or triphosphate ester; trityl or monomethoxytrityl; $R_{12}SO$; $R_{12}SO_2$; $CF_3S$; $CF_3SO_2$; and trialkylsilyl; or wherein X and Y form a fused aryl ring together with the phenyl ring to which X, Y, and Z are attached;
- Y and Z are each independently selected from H; optionally substituted C1-10 alkyl; optionally substituted C1-10 alkoxy; optionally substituted C2-10 alkenyl; optionally substituted C2-10 alkynyl; optionally substituted C6-C12 aryl; alkaryl; arylalkyl; aryloxy; optionally substituted heteroaryl; optionally substituted heterocycle; halo; hydroxyl; halogenated alkyl; an amino group of formula $NH_2$, $NR_{12}H$, or $NR_{12}R_{13}$; alkylamino; arylamino; acyl; CN; $NO_2$; $N_3$; $CH_2OH$; $CONH_2$; $CONR_{12}R_{13}$; $CO_2R_{12}$; $CH_2OR_{12}$; $NHCOR_{12}$; $NHCO_2R_{12}$; C1-3 alkylthio; sulfate; sulfonic acid; sulfonate ester; phosphonic acid; phosphate; phosphonate; mono-, di-, or triphosphate ester; trityl or monomethoxytrityl; $R_{12}SO$; $R_{12}SO_2$; $CF_3S$; $CF_3SO_2$; trialkylsilyl; and diphenylmethylsilyl; or wherein Y and Z form a fused aryl ring together with the phenyl ring to which X, Y, and Z are attached; and
- $R_{12}$ and $R_{13}$ are each independently selected from H or optionally substituted C1-10 alkyl;
with the proviso that: (a) X is a halo substituent other than chloro; (b) two or more of X, Y, and Z are halo substituents; (c) one or more of X, Y, and Z are optionally substituted C6-C12 aryl; (d) X and Y or Y and Z form a fused aryl ring together with the phenyl ring to which X, Y, and Z are attached; (e) $R_1$ is an optionally substituted C2-C10 alkyl; or any combination of two or more of (a) through (e);

or a pharmaceutically acceptable ester, amide, salt, solvate, prodrug, or stereoisomer thereof.

2. The compound according to claim 1, having the structure:

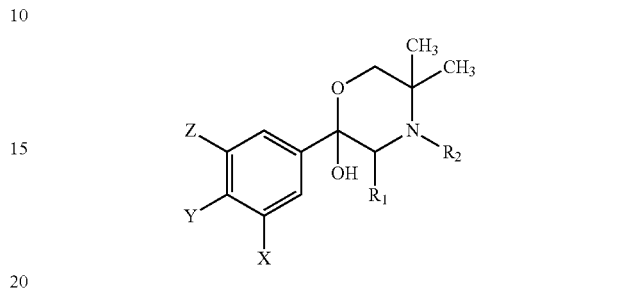

or a pharmaceutically acceptable ester, amide, salt, solvate, prodrug, or stereoisomer thereof.

3. The compound according to claim 1, having the structure:

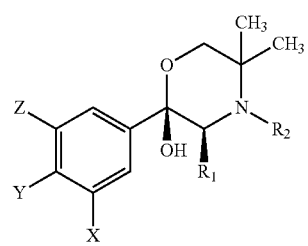

or a pharmaceutically acceptable ester, amide, salt, solvate, prodrug, or stereoisomer thereof.

4. The compound according to claim 1, wherein $R_1$ is selected from the group consisting of $CH_3$, $CH_2CH_3$, and $C_3H_7$.

5. The compound according to claim 2, wherein $R_1$ is selected from the group consisting of $CH_3$, $CH_2CH_3$, and $C_3H_7$.

6. The compound according to claim 3, wherein $R_1$ is selected from the group consisting of $CH_3$, $CH_2CH_3$, and $C_3H_7$.

7. The compound according to claim 1, wherein X is selected from the group consisting of Br, F, optionally substituted C1-10 alkoxy, and $NO_2$.

8. The compound according to claim 2, wherein X is independently selected from the group consisting of Br, F, optionally substituted C1-10 alkoxy, and $NO_2$.

9. The compound according to claim 3, wherein X is independently selected from the group consisting of Br, F, optionally substituted C1-10 alkoxy, and $NO_2$.

10. The compound according to claim 1, wherein X and Y or Y and Z form a fused aryl ring together with the phenyl ring to which X, Y, and Z are attached.

11. The compound according to claim 2, wherein X and Y or Y and Z form a fused aryl ring together with the phenyl ring to which X, Y, and Z are attached.

12. The compound according to claim 3, wherein X and Y or Y and Z form a fused aryl ring together with the phenyl ring to which X, Y, and Z are attached.

13. The compound according to claim 1, selected from the group consisting of:

2-(3,4,5-Trifluorophenyl)-3,5,5-trimethylmorpholin-2-ol;
2-(3,4-Dibromophenyl)-3,5,5-trimethylmorpholin-2-ol;
2-(3,5-Dibromophenyl)-3,5,5-trimethylmorpholin-2-ol;
2-(3,4,5-Tribromophenyl)-3,5,5-trimethylmorpholin-2-ol;
2-(3-Fluoro-4-methylphenyl)-3,5,5-trimethylmorpholin-2-ol;
2-(3-Fluoro-5-methylphenyl)-3,5,5-trimethylmorpholin-2-ol;
2-(3-Fluoro-4,5-dimethylphenyl)-3,5,5-trimethylmorpholin-2-ol;
2-(4-Methyl-3,5-difluorophenyl)-3,5,5-trimethylmorpholin-2-ol;
2-(3-Methyl-4,5-difluorophenyl)-3,5,5-trimethylmorpholin-2-ol;
2-(3-Bromo-4-methylphenyl)-3,5,5-trimethylmorpholin-2-ol;
2-(3-Bromo-5-methylphenyl)-3,5,5-trimethylmorpholin-2-ol;
2-(3-Bromo-4,5-dimethylphenyl)-3,5,5-trimethylmorpholin-2-ol;
2-(4-Methyl-3,5-dibromophenyl)-3,5,5-trimethylmorpholin-2-ol;
2-(3-Methyl-4,5-dibromophenyl)-3,5,5-trimethylmorpholin-2-ol;
2-(3-Fluoro-4-ethylphenyl)-3,5,5-trimethylmorpholin-2-ol;
2-(3-Fluoro-5-ethylphenyl)-3,5,5-trimethylmorpholin-2-ol;
2-(3-Fluoro-4,5-diethylphenyl)-3,5,5-trimethylmorpholin-2-ol;
2-(4-Ethyl-3,5-difluorophenyl)-3,5,5-trimethylmorpholin-2-ol;
2-(3-Ethyl-4,5-difluorophenyl)-3,5,5-trimethylmorpholin-2-ol;
2-(3-Bromo-4-ethylphenyl)-3,5,5-trimethylmorpholin-2-ol;
2-(3-Bromo-5-ethylphenyl)-3,5,5-trimethylmorpholin-2-ol;
2-(3-Bromo-4,5-diethylphenyl)-3,5,5-trimethylmorpholin-2-ol;
2-(4-Ethyl-3,5-dibromophenyl)-3,5,5-trimethylmorpholin-2-ol;
2-(3-Ethyl-4,5-dibromophenyl)-3,5,5-trimethylmorpholin-2-ol;
2-(3-Fluoro-4-propylphenyl)-3,5,5-trimethylmorpholin-2-ol;
2-(3-Fluoro-5-propylphenyl)-3,5,5-trimethylmorpholin-2-ol;
2-(3-Fluoro-4,5-dipropylphenyl)-3,5,5-trimethylmorpholin-2-ol;
2-(4-Propyl-3,5-difluorophenyl)-3,5,5-trimethylmorpholin-2-ol;
2-(3-Propyl-4,5-difluorophenyl)-3,5,5-trimethylmorpholin-2-ol;
2-(3-Bromo-4-propylphenyl)-3,5,5-trimethylmorpholin-2-ol;
2-(3-Bromo-5-propylphenyl)-3,5,5-trimethylmorpholin-2-ol;
2-(3-Bromo-4,5-dipropylphenyl)-3,5,5-trimethylmorpholin-2-ol;
2-(4-Propyl-3,5-dibromophenyl)-3,5,5-trimethylmorpholin-2-ol;
2-(3-Propyl-4,5-dibromophenyl)-3,5,5-trimethylmorpholin-2-ol;
2-(Naphthalen-2-yl)-3,5,5-trimethylmorpholin-2-ol;
2-(4-Chloronaphthalen-2-yl)-3,5,5-trimethylmorpholin-2-ol;
2-(4-Floronaphthalen-2-yl)-3,5,5-trimethylmorpholin-2-ol;
2-(4-Bromonaphthalen-2-yl)-3,5,5-trimethylmorpholin-2-ol;
2-(4-Methylnaphthalen-2-yl)-3,5,5-trimethylmorpholin-2-ol;
2-(4-Ethylnaphthalen-2-yl)-3,5,5-trimethylmorpholin-2-ol;
2-(4-Propylnaphthalen-2-yl)-3,5,5-trimethylmorpholin-2-ol;
2-(4-Methoxynaphthalen-2-yl)-3,5,5-trimethylmorpholin-2-ol;
2-(4-Nitronaphthalen-2-yl)-3,5,5-trimethylmorpholin-2-ol;
and pharmaceutically acceptable esters, amides, salts, solvates, prodrugs, and stereoisomers thereof.

14. The compound according to claim 1, selected from the group consisting of:

2-(3-Bromophenyl)-3,5,5-trimethylmorpholin-2-ol;
2-(3-Fluorophenyl)-3,5,5-trimethylmorpholin-2-ol;
2-(3,5-Difluorophenyl)-3,5,5-trimethylmorpholin-2-ol;
and pharmaceutically acceptable esters, amides, salts, solvates, prodrugs, and stereoisomers thereof.

15. The compound according to claim 1, wherein the compound comprises an enantiomeric excess of at least 95% of the (2S-3S) enantiomer.

16. The compound according to claim 2, wherein the compound comprises an enantiomeric excess of at least 95% of the (2S-3S) enantiomer.

17. A pharmaceutical composition comprising a compound according to claim 1 and one or more pharmaceutically acceptable carriers.

18. A method for treating or delaying the progression of disorders that are alleviated by inhibiting monoamine reuptake in a patient or antagonizing the nicotinic acetylcholine receptors, the method comprising administering a therapeutically effective amount of at least one compound according to claim 1.

19. The method of claim 18, wherein the disorder is selected from the group consisting of addiction, depression, obesity, bipolar disorder, attention deficit disorder (ADD), attention deficit/hyperactivity disorder (ADHD), hypoactive sexual desire disorder, antidepressant-induced sexual dysfunction, orgasmic dysfunction, seasonal affective disorder/winter depression, mania, bulimia and other eating disorders, panic disorders, obsessive compulsive disorder, schizophrenia, schizo-affective disorder, Parkinson's disease, narcolepsy, anxiety disorders, insomnia, chronic pain, migraine headaches, and restless legs syndrome.

20. The method of claim 19, wherein the addiction comprises nicotine addiction.

* * * * *